US008614186B2

(12) United States Patent
Kufe et al.

(10) Patent No.: US 8,614,186 B2
(45) Date of Patent: *Dec. 24, 2013

(54) INHIBITION OF INFLAMMATION USING ANTAGONISTS OF MUC1

(75) Inventors: Donald W. Kufe, Wellesley, MA (US); Surender Kharbanda, Natick, MA (US)

(73) Assignees: Dana-Farber Cancer Institute, Inc., Boston, MA (US); Genus Oncology, LLC., Chicago, IL (US)

( * ) Notice: Subject to any disclaimer, the term of this patent is extended or adjusted under 35 U.S.C. 154(b) by 135 days.

This patent is subject to a terminal disclaimer.

(21) Appl. No.: 12/789,127

(22) Filed: May 27, 2010

(65) Prior Publication Data
US 2011/0015138 A1    Jan. 20, 2011

Related U.S. Application Data

(60) Provisional application No. 61/181,530, filed on May 27, 2009, provisional application No. 61/253,730, filed on Oct. 21, 2009, provisional application No. 61/303,997, filed on Feb. 12, 2010.

(51) Int. Cl.
A61K 38/00    (2006.01)
A61P 29/00    (2006.01)

(52) U.S. Cl.
USPC ........................................................ 514/12.2

(58) Field of Classification Search
None
See application file for complete search history.

(56) References Cited

U.S. PATENT DOCUMENTS

| 5,595,756 | A | 1/1997 | Bally et al. | |
| 5,912,232 | A | 6/1999 | Talmadge | |
| 6,548,643 | B1 | 4/2003 | McKenzie et al. | 530/395 |
| 7,118,862 | B2 | 10/2006 | Kufe et al. | 435/7.23 |
| 7,247,297 | B2 | 7/2007 | Weichselbaum et al. | 424/93.2 |
| 7,556,935 | B2 | 7/2009 | Kufe et al. | 435/15 |
| 2002/0044943 | A1 | 4/2002 | Longenecker et al. | |
| 2002/0086829 | A1 | 7/2002 | Gefter | 514/10.1 |
| 2005/0042209 | A1 | 2/2005 | Kufe et al. | 514/44 |
| 2005/0053606 | A1 | 3/2005 | Kufe et al. | 424/155.1 |
| 2005/0089957 | A1* | 4/2005 | Goddard et al. | 435/69.1 |
| 2005/0271650 | A1 | 12/2005 | Freimark et al. | |
| 2005/0282744 | A1 | 12/2005 | Hollingsworth et al. | 530/300 |
| 2006/0293234 | A1 | 12/2006 | Schroeder | 514/2 |
| 2007/0071675 | A1 | 3/2007 | Wu et al. | 424/1.49 |
| 2007/0105767 | A1 | 5/2007 | Kharbanda et al. | 514/8 |
| 2007/0202134 | A1 | 8/2007 | Kufe et al. | 536/24.5 |
| 2007/0207209 | A1 | 9/2007 | Murphy et al. | |
| 2008/0286264 | A1 | 11/2008 | Kufe | 435/7.23 |
| 2009/0047307 | A1 | 2/2009 | Harrop et al. | |
| 2009/0087437 | A1 | 4/2009 | Kufe | 435/4 |
| 2009/0092600 | A1 | 4/2009 | Kufe | 435/7.1 |
| 2009/0098054 | A1 | 4/2009 | Kufe | 435/7.1 |
| 2009/0136520 | A1 | 5/2009 | Kufe | 435/7.23 |
| 2009/0232812 | A1 | 9/2009 | Kufe et al. | 424/155.1 |
| 2010/0125055 | A1* | 5/2010 | Kufe et al. | 514/13 |
| 2011/0251246 | A1* | 10/2011 | Kufe et al. | 514/365 |
| 2012/0045502 | A1* | 2/2012 | Kufe et al. | 424/450 |
| 2012/0172312 | A1* | 7/2012 | Kufe et al. | 514/19.3 |

FOREIGN PATENT DOCUMENTS

| EP | 1538164 A1 * | 8/2005 |
| WO | WO 00/34468 | 6/2000 |
| WO | WO 01/18035 | 3/2001 |
| WO | WO 01/57068 | 8/2001 |
| WO | WO 2005/101021 | 10/2005 |
| WO | WO 2008/121767 | 10/2008 |

OTHER PUBLICATIONS

Hruby. Designing peptide receptor agonists and antagonists. Nature Reviews. Drug Discovery. Nov. 2002. vol. 1., pp. 847-858.*
Abe and Kufe, "Structural analysis of the DF3 human breast carcinoma-associated protein," Cancer Res., 49(11):2834-2839, 1989.
Ahmad et al.,"MUC I oncoprotein activates the IkappaB kinase beta complex and constitutive NF-kappaB signalling," Nat. Cell Biol., 9:1419-1427, 2007.
Ahmad et al.,"MUC1-C oncoprotein functions as a direct activator of the nuclear factor-κβ p65 transcription factor," Cancer Research, 69: 7013-21, 2009.
Ahmad et al., "Triterpenoid CDDO-Me blocks the NF-kappaB pathway by direct inhibition of IKKbeta on Cys-179," J. Biol. Chem., 281:35764-9, 2006.
Anderson et al., "Multiple myeloma: New insights and therapeutic approaches," Hematology, 1:147-165, 2000.
Arkin et al., "Structural aspects of oligomerization taking place between the transmembrane a-helices of bitopic membrane proteins," Biochimica et Biophysica Acta, 1565:347-363, 2002.
Baldus et al., "MUC1 and nuclear beta-catenin are coexpressed at the invasion front of colorectal carcinomas and are both correlated with tumor prognosis," Clin. Cancer Res., 10(8):2790-2796, 2004.
Beatty et al., "Cutting edge: Transgenic expression of human MUC1 in IL-10 –/– Mice accelerates inflammatory bowel disease and progression to colon cancer," J. Immunol.., 179:735-739, 2007.
Begum et al., "Muc 1 based breast cancer vaccines: role of post translational modifications," J. Ayub. Med. Coll. Abbottabad., 20(4):130-133, 2008.
Bitler et al., "Intracellular MUC1 peptides inhibit cancer progression," Clin. Canc. Res., 15 (1): 100-109, 2009.
Fischer, "Cellular uptake mechanisms and potential therapeutic utility of peptidic cell delivery vectors: Progress 2001-2006," Medicinal Research Reviews, 27 (6): 755-795, 2007.
Hodel et al., "The three-dimensional structure of the autoproteolytic, nuclear pore-targeting domain of the human nucleoporin Nup98," Mol. Cell, 10(2):347-58, 2002.

(Continued)

Primary Examiner — Marcela M Cordero Garcia
(74) Attorney, Agent, or Firm — Parker Highlander PLLC

(57) ABSTRACT

The invention provides for peptides from the MUC1 cytoplasmic domain and methods of use therefor. These peptides can inhibit MUC1 oligomerization, inhibit the interaction of MUC1 with NF-κB or a STAT, and block inflammatory response mediated by NF-κB or STAT signaling.

27 Claims, 26 Drawing Sheets

(56) References Cited

OTHER PUBLICATIONS

Hu et al., "MUC1 cytoplasmic tail: a potential therapeutic target for ovarian cancer," *Future Drugs*, 6(8):1261-1271, 2006.

Huang et al., "MUC1 cytoplasmic domain coactivates Wnt target gene transcription and confers transformation," *Cancer Biol. Ther.*, 2 (6): 702-706, 2003.

Huang et al., "MUC1 oncoprotein blocks glycogen synthase kinase 3beta-mediated phosphorylation and degradation of beta-catenin," *Cancer Res.*, 65:10413-10422, 2005.

Joshi et al., "MUC1 oncoprotein is a druggable target in human prostate cancer cells," *Mol. Cancer Ther.*, 8 (11): 3056-3065, 2009.

Kau et al., "Nuclear transport and cancer: from mechanism to intervention," *Nat. Rev. Cancer*, 4(2):106-17, 2004.

Kawano et al.,"MUC1 oncoprotein promotes growth and survival of human multiple myeloma cells," *International Journal of Oncology*, 33:153-159, 2008.

Khodarev et al., "Cooperativity of the MUC1 oncoprotein and STAT1 pathway in poor prognosis human breast cancer," *Oncogene*, 2009.

Kinlough et al., "Recycling of MUC1 is dependent on its palmitoylation," *The Journal of Biological Chemistry*, 281(17):12112-12122, 2006.

Kufe et al., "Differential reactivity of a novel monoclonal antibody (DF3) with human malignant versus benign breast tumors," *Hybridoma*, 3 (3):223-232, 1984.

Kufe, "Functional targeting of the MUC1 oncogene in human cancers," *Cancer Biology & Therapy*, 8 (13): 1197-1203, 2009.

Kufe, "Human MUC1 oncoprotein is of functional importance fo the development of prostate cancer," Award No. W81XWH-08-1-0093, Annual Report, prepared for U.S. Army Medical Research and Materiel Command, Mar. 2009.

Kufe, "Mucins in cancer: function, prognosis and therapy," *Nat. Rev. Cancer*, 9 (12): 874-885, 2009.

Kufe, "Targeting the human MUC1 oncoprotein: a tale of two proteins," *Cancer Biol. Ther.*, 7 (1): 81-84, 2008.

Leng et al., "Nuclear import of the MUC1-C oncoprotein is mediated by nucleoporin Nup62," *The Journal of Biological Chemistry*, 282 (27): 19321-19330, 2007.

Levitin et al., "The MUC1 SEA module is a self-cleaving domain," *J. Biol. Chem.*, 280:33374-33386, 2005.

Li and Cozzi, "MUC1 is a promising therapeutic target for prostate cancer therapy," *Current Cancer Drugs Targets*, 7:259-271, 2007.

Li et al., "DF3/MUC1 Signaling in Multiple Myeloma Cells Is Regulated by Interleukin-7," *Cancer Biol. Ther.*, 2:187-193, 2003.

Li et al., "Heregulin targets gamma-catenin to the nucleolus by a mechanism dependent on the DF3/MUC1 oncoprotein," *Mol. Cancer Res.*, 1 (10):765-775, 2003.

Li et al., "Human DF3/MUC1 carcinoma-associated protein functions as an oncogene," *Oncogene*, 22 (38): 6107-6110, 2003.

Li et al., "Interaction of glycogen synthase kinase 3beta with the DF3/MUC1 carcinoma-associated antigen and beta-catenin," *Mol. Cell Biol.*, 18:7216-7224, 1998.

Li et al., "The c-Src tyrosine kinase regulates signaling of the human DF3/MUC1 carcinoma-associated antigen with GSK3 beta and beta-catenin," *J. Biol. Chem.*, 276(9):6061-6064, 2001.

Li et al., "The epidermal growth factor receptor regulates interaction of the human DF3/MUC1 carcinoma antigen with c-Src and beta-catenin," *J. Biol. Chem.*, 276:35239-35242, 2001.

Ligtenberg et al., "Cell-associated episialin is a complex containing two proteins derived from a common precursor," *J. Biol. Chem.*, 267 (9), 6171-6177, 1992.

Macao, "Autoproteolysis coupled to protein folding in the SEA domain of the membrane-bound MUC1 mucin," *Nat. Struct. Mol. Biol.*, 13 (1), 71-76, 2006.

PCT International Search Report and Written Opinion, issued in International application No. PCT/US2009/061051, dated Nov. 26, 2010.

PCT International Search Report and Written Opinion, issued in International patent Application No. PCT/US10/36436, dated Oct. 19, 2010.

Peczuh et al., "Peptide and protein recognition by designed molecules," *Chem. Rev.*, 100:2479-2494, 2000.

Raina et al., "Direct targeting of the mucin 1 oncoprotein blocks survival and tumorigenicity of human breast carcinoma cells," *Cancer Res.*, 69 (12): 5133-5141, 2009.

Raina et al., "MUC1 oncoprotein blocks nuclear targeting of c-Abl in the apoptotic response to DNA damage," *EMBO J.*, 25:3774-3783, 2006.

Raina et al., "The MUC1 oncoprotein activates the anti-apoptotic phosphoinositide 3-kinase/Akt and Bcl-xL pathways in rat 3Y1 fibroblasts," *J. Biol. Chem.*, 279 (20):20607-20612, 2004.

Ramasamy et al., "The MUC1 and galectin-3 oncoproteins function in a microRNA-dependent regulatory loop," *Mol. Cell*, 27 (6):992-1004, 2007.

Ren et al., "Human MUC1 carcinoma-associated protein confers resistance to genotoxic anticancer agents," *Cancer Cell*, 5 (2):163-175, 2004.

Ren et al.,"MUC1 oncoprotein functions in activation of fibroblast growth factor receptor signaling," *Mol. Cancer Res.*, 4 (11): 873-883, 2006.

Ren et al., "MUC1 oncoprotein is targeted to mitochondria by heregulin-induced activation of c-Src and the molecular chaperone HSP90," *Oncogene*, 25 (1):20-31, 2006.

Ren et al., "Protein kinase C delta regulates function of the DF3/MUC1 carcinoma antigen in beta-catenin signaling," *J. Biol. Chem.*, 277 (20):17616-17622, 2002.

Schroeder et al., "MUC1 overexpression results in mammary gland tumorigenesis and prolonged alveolar differentiation," *Oncogene*, 23 (34):5739-5747, 2004.

Schroeder et al., "Transgenic MUC1 interacts with epidermal growth factor receptor and correlates with mitogen-activated protein kinase activation in the mouse mammary gland," *J. Biol. Chem.*, 276(16):13057-13064 2001.

Truscott et al., "A J-protein is an essential subunit of the presequence translocase-associated protein import motor of mitochondria," *J. Cell Biol.*, 163(4):707-713, 2003.

Tsutsumida et al., "RNA interference suppression of MUC1 reduced the growth rate and metastatic phenotype of human pancreatic cancer cells," *Clin. Cancer Res.*, 120(10):2976-2987, 2006.

Vermeer et al., "Segregation of receptor and ligand regulates activation of epithelial growth factor receptor," *Nature*, 422(6929):322-6, 2003.

Wei et al., "Human MUC1 oncoprotein regulates p53-responsive gene transcription in the genotoxic stress response," *Cancer Cell*, 7 (2):167-178, 2005.

Wei et al., "MUC1 oncoprotein stabilizes and activates estrogen receptor alpha," *Mol. Cell.*, 21 (2): 295-305, 2006.

Weis, "Regulating access to the genome: nucleocytoplasmic transport throughout the cell cycle," *Cell*, 112(4):441-51, 2003.

Wen et al., "Nuclear association of the cytoplasmic tail of MUC1 and beta-catenin," *J. Biol. Chem.*, 278 (39):38029-38039, 2003.

Yamamoto et al., "Interaction of the DF3/MUC1 breast carcinoma-associated antigen and beta-catenin in cell adhesion," *J. Biol. Chem.*, 272 (19):12492-12494, 1997.

Yin et al., "Human MUC1 carcinoma antigen regulates intracellular oxidant levels and the apoptotic response to oxidative stress," *J. Biol. Chem.*, 278 (37):35458-35464, 2003b.

Yin et al., "MUC1 oncoprotein activates the FOXO3a transcription factor in a survival response to oxidative stress," *J. Biol. Chem.*, 279 (44):45721-45727, 2004.

Yin et al., "MUC1 oncoprotein promotes autophagy in a survival response to glucose deprivation," *Int. J. Oncol.*, 34 (6): 1691-1699, 2009.

Yin et al., "Mucin 1 oncoprotein blocks hypoxia-inducible factor 1alpha activation in a survival response to hypoxia," *J. Biol. Chem.*, 282 (1):257-266, 2007.

Young et al., "Molecular chaperones Hsp90 and Hsp70 deliver preproteins to the mitochondrial import receptor Tom70," *Cell.* 112 (1): 41-50, 2003.

Raina et al., "Dependence on the MUC1-C oncoprotein in non-small cell lung cancer cells," Mol. Cancer Ther., 10(5):806-816, May 2011. E-published Mar. 18, 2011. DOI:10.1158/1535-7163.mct-10-1050.

(56) References Cited

OTHER PUBLICATIONS

Yin et al., "MUC1-C oncoprotein suppresses reactive oxygen species-induced terminal differentiation of acute myelogenous leukemia cells," Blood., 117(18):4863-4870, May 5, 2011. E-published Mar. 21, 2011. DOI:10.1182/blood-2010-296632.

Zhou et al., "MUC1 oncoprotein is a target for small molecule inhibitors," Molecular Pharmacology, Published online before print Feb. 23, 2011, DOI: 10.1124/mol.110.070797.

Aurerbach et al., "Angiogenesis assays: Problems and pitfalls," *Cancer and Metastasis Reviews*, 19:167-172, 2000.

Gura, "Systems for identifying new drugs are often faulty," *Science*, 278:1041-1042, 1997.

Jain, "Barriers to drug delivery in solid tumors," *Scientific American*, 58-65, 1994.

Office Communication issued in European patent application No. 09740811.6, dated Jun. 22, 2012.

Office Communication issued in U.S. Appl. No. 12/580,865, dated Dec. 27, 2011.

Office Communication issued in U.S. Appl. No. 12/580,865, dated May 24, 2012.

Office Communication issued in U.S. Appl. No. 12/580,865, dated Nov. 2, 2012.

Response to Office Communication issued in U.S. Appl. No. 12/580,865, dated Feb. 23, 2012.

Response to Office Communication issued in U.S. Appl. No. 12/580,865, dated Sep. 24, 2012.

Response to Office Communication issued in U.S. Appl. No. 12/580,865, dated Feb. 4, 2013.

Sporn and Suh, "Chemoprevention of cancer," *Carciogenesis*, 21:525-530, 2000.

Spicer et al., "Molecular cloning and analysis of the mouse homologue of the tumor-associated mucin, MUCI, reveals conservation of potential 0-glycosylation sites, transmembrane, and cytoplasmic domains, and a loss of minisatellite—like polymorphism," *J. Biol. Chem.*, 266(23): 15099-15109, 1991.

Supplementary European Search Report issued in European Patent Application No. 10781227.3, dated Dec. 3, 2012.

English Translation of Office Communication issued in corresponding Chinese Patent Application 200980149998.9, dated Mar. 4, 2013.

English Translation of Ling et al. "MUCI C-terminal Heterodimer and Its Tumorgenicity," *Progress in Biochemistry and Biophysics*, 34(4): 375-381, 2007.

Ling et al." MUCI C-terminal Heterodimer and Its Tumorgenicity," *Progress in Biochemistry and Biophysics*, 34(4): 375-381, 2007.

\* cited by examiner

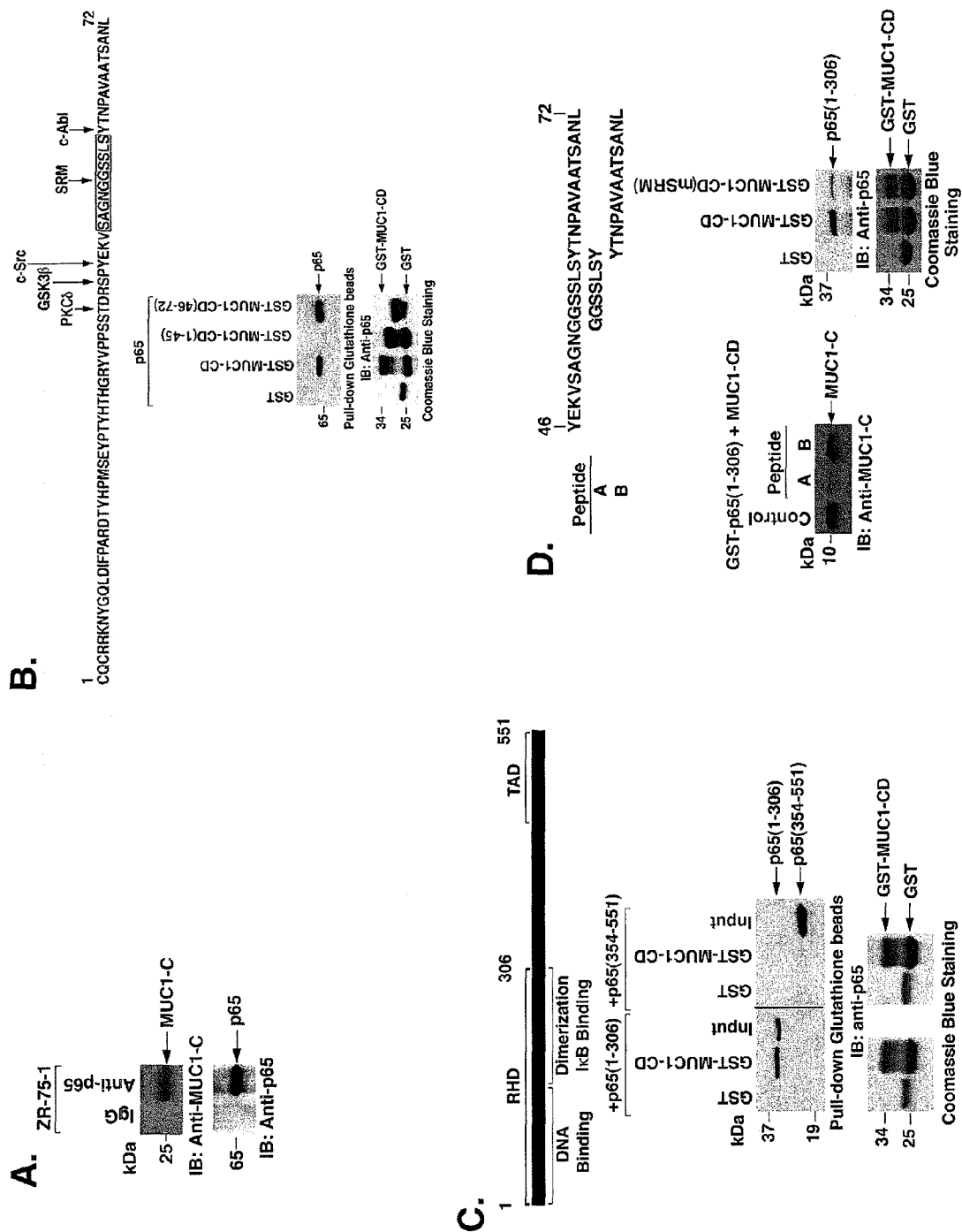
FIG 1A-D

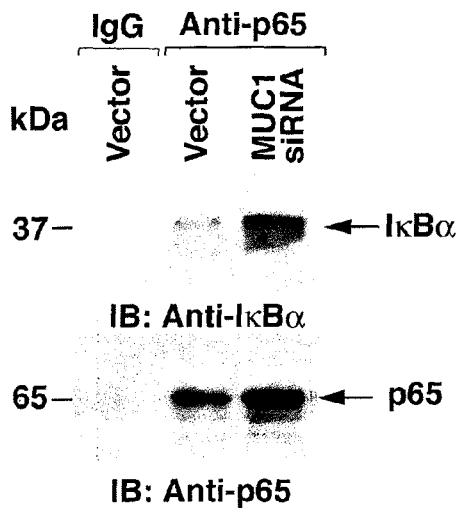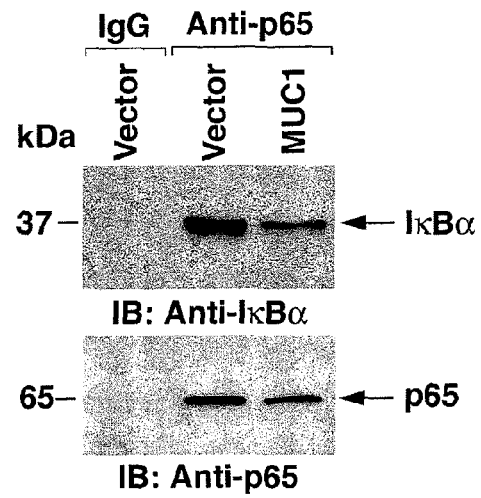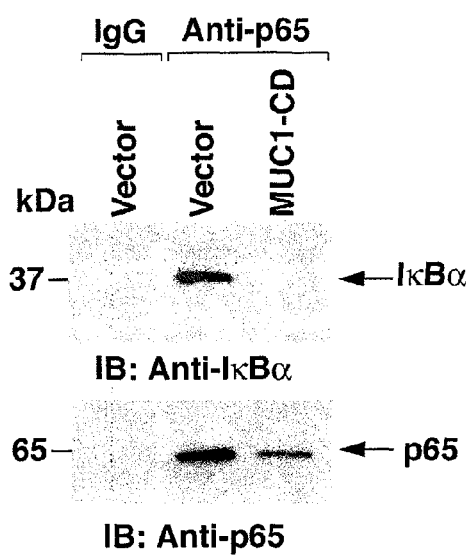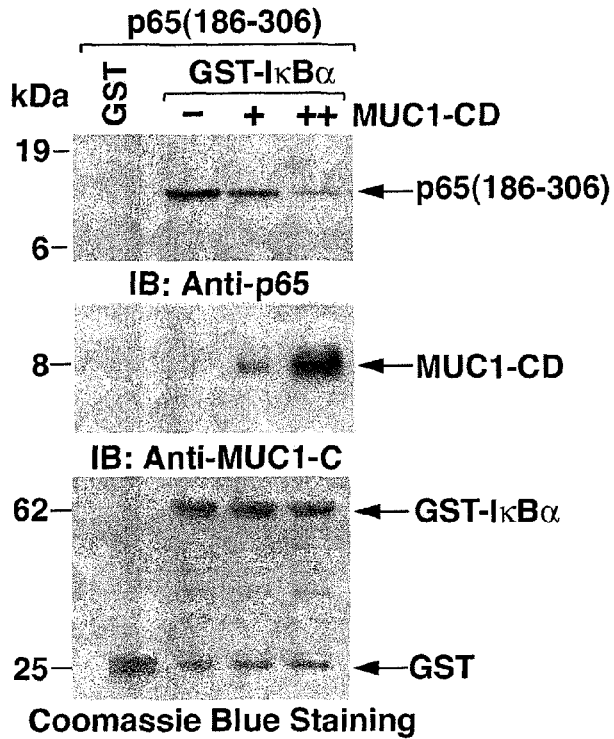
FIG. 2A-D

A. ZR-75-1
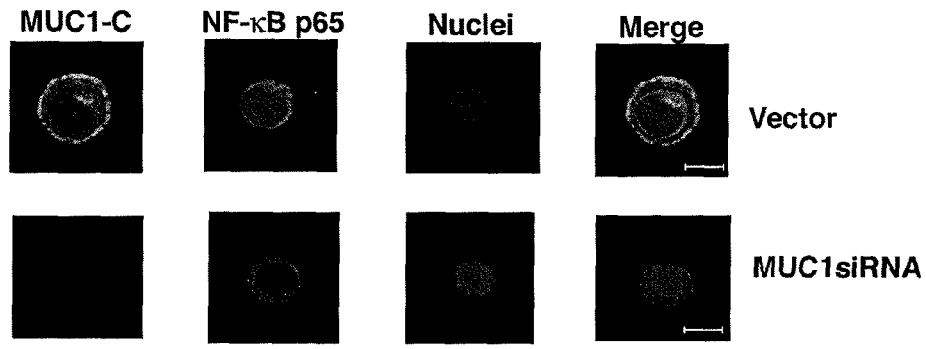
B. ZR-75-1
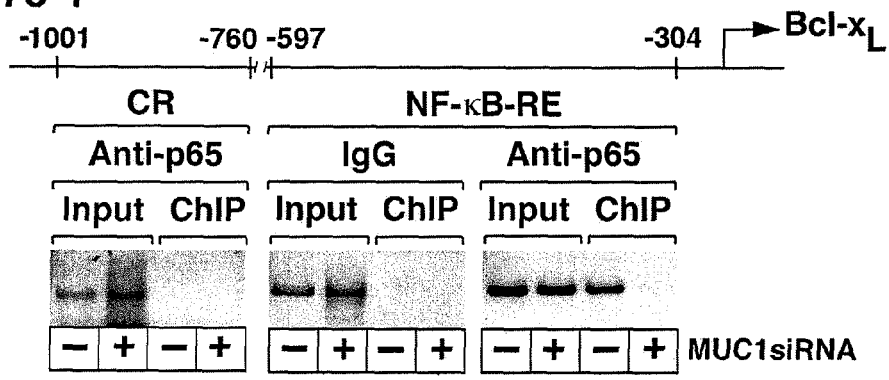
C. HeLa
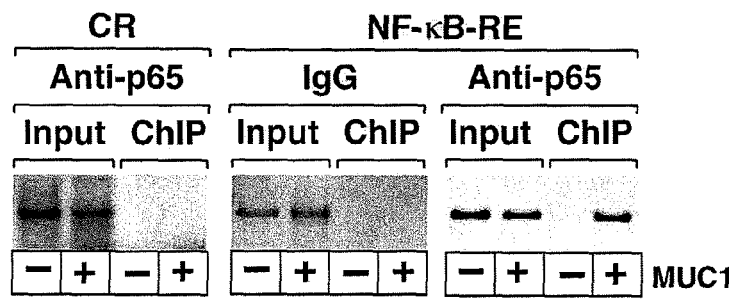
D. ZR-75-1
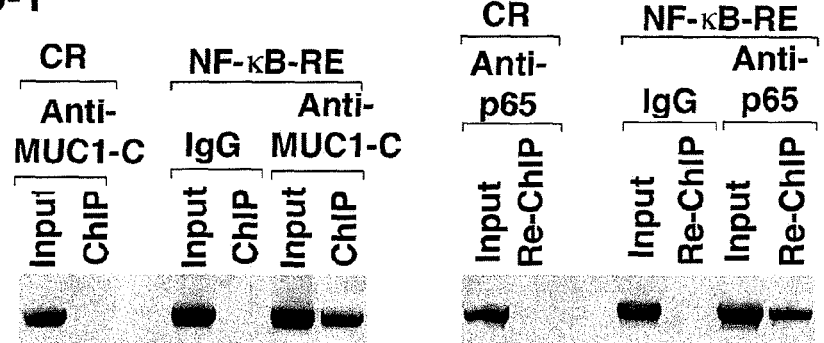
FIG. 3A-D

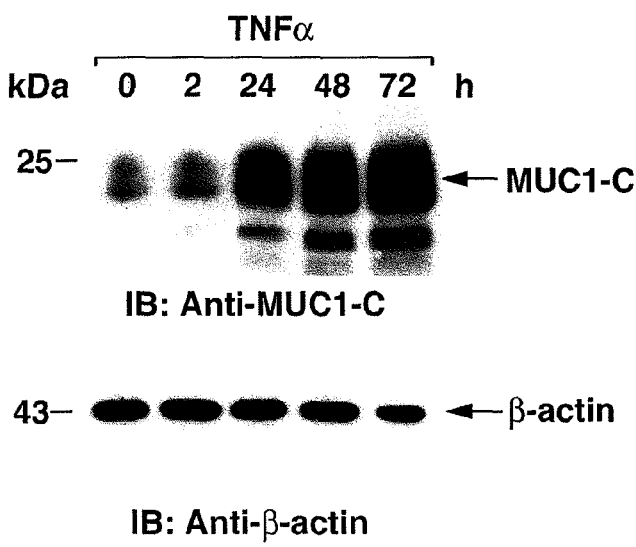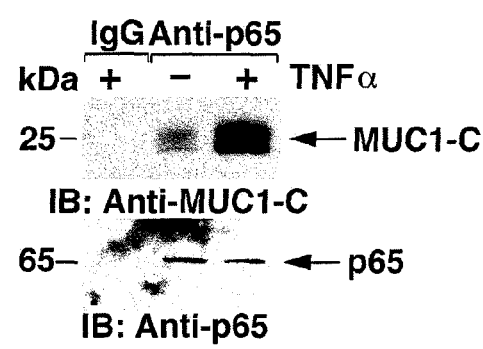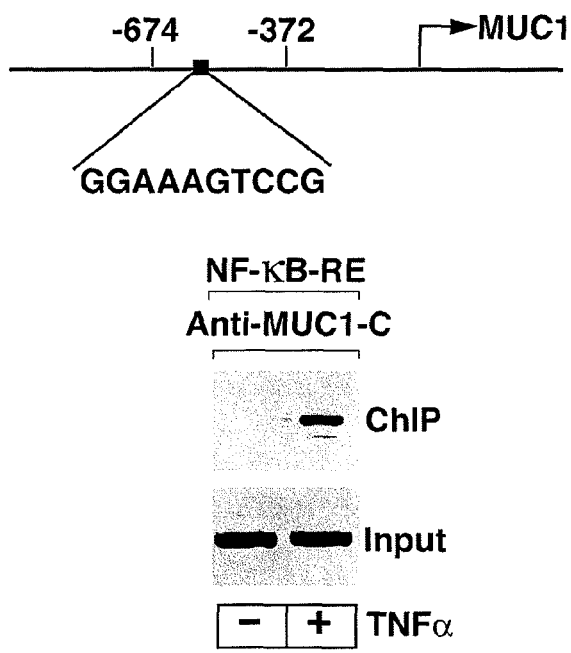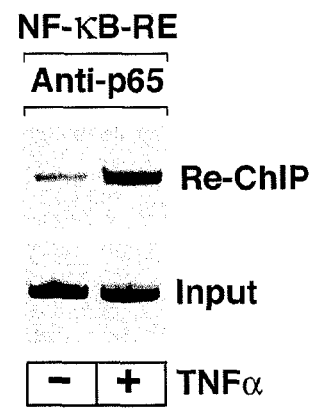
FIG. 4A-D

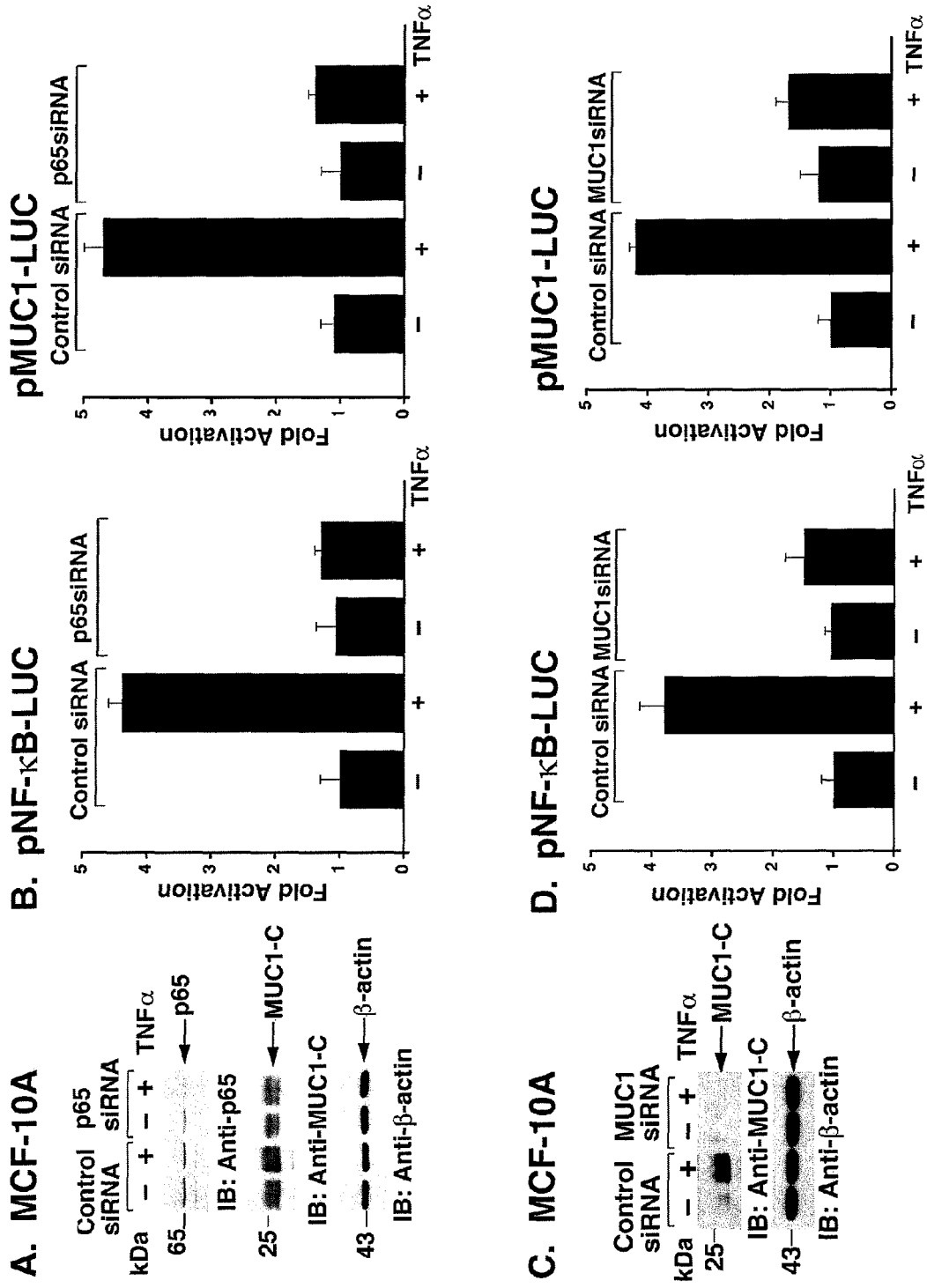
FIG. 5A-D

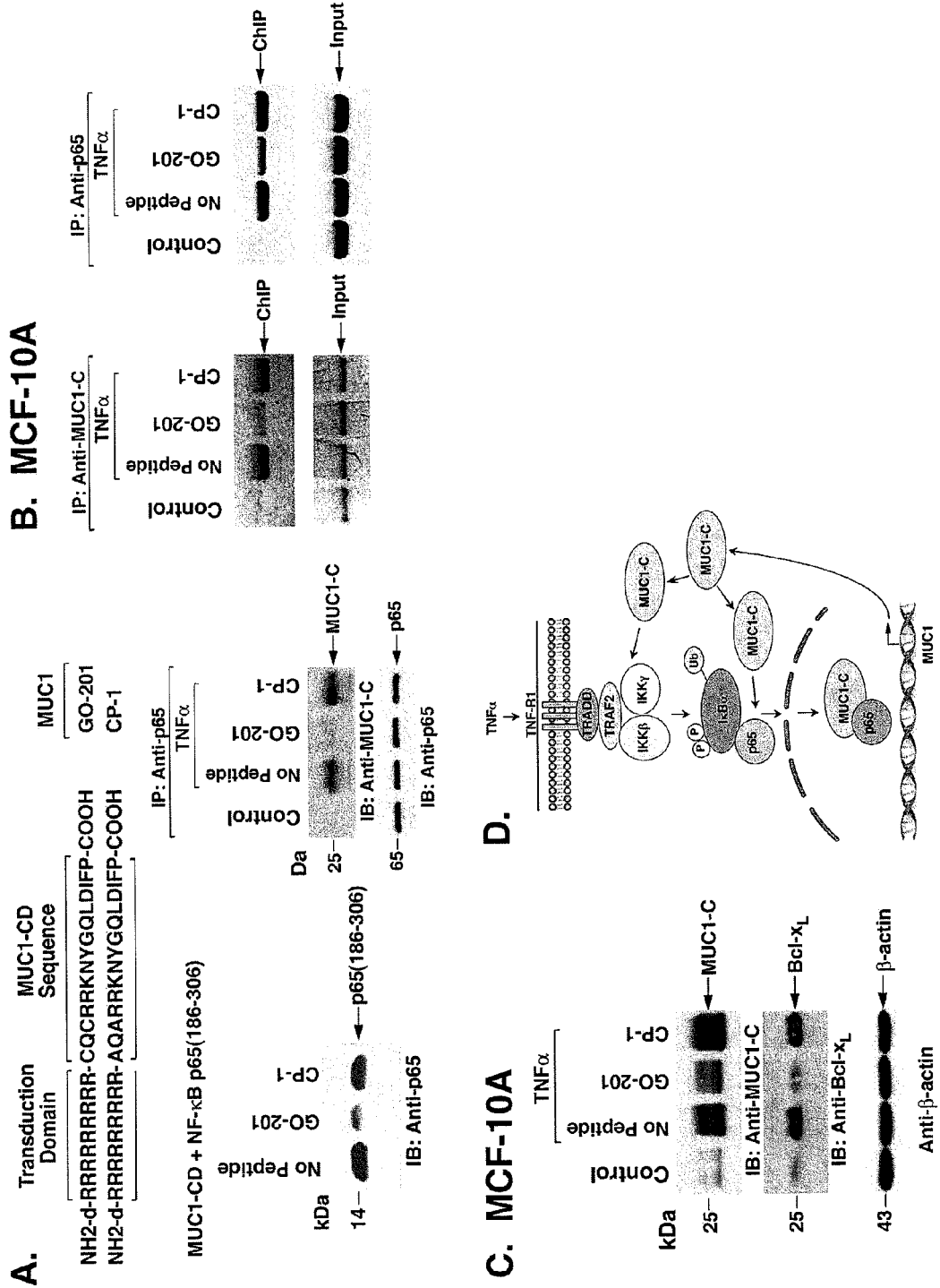
FIG. 6A-D

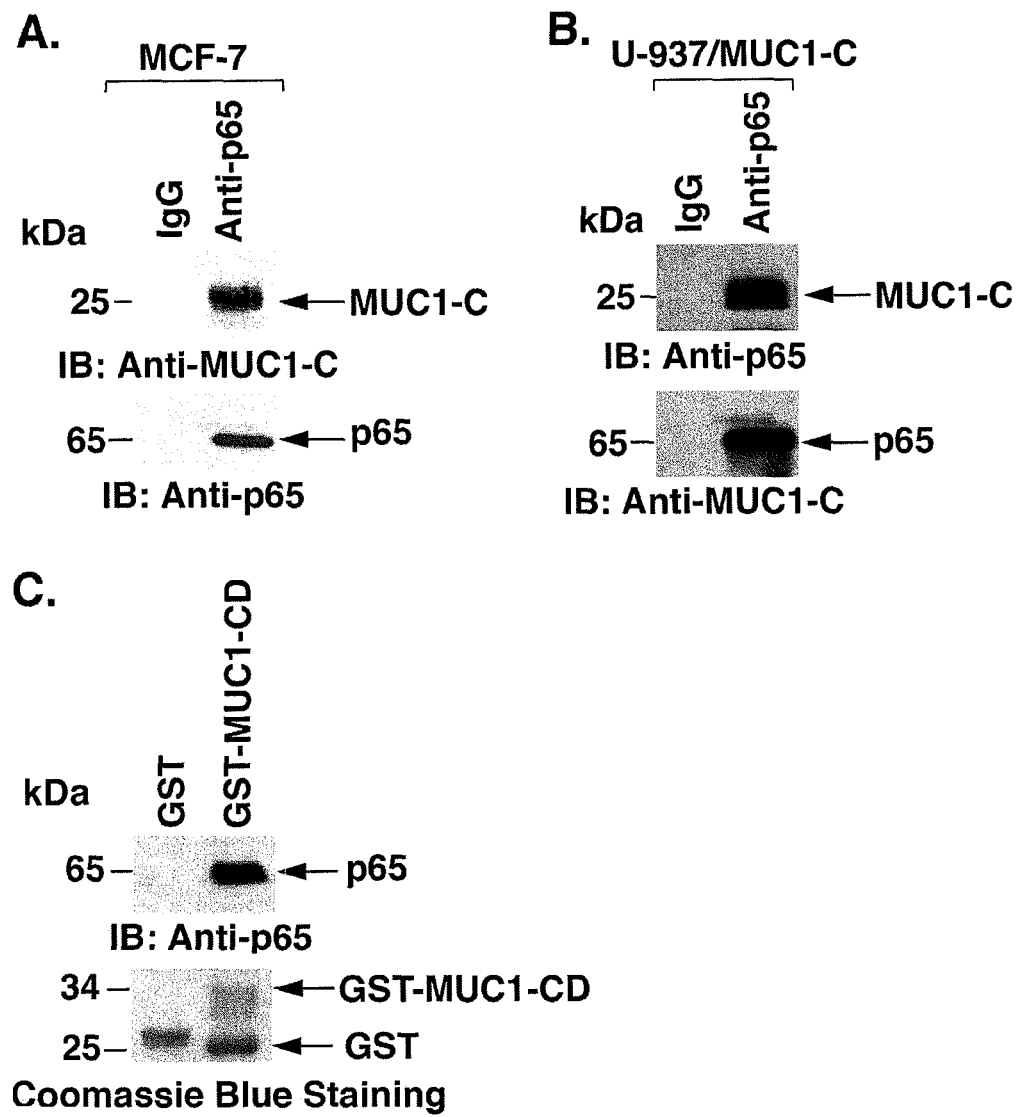
FIG. 7A-C

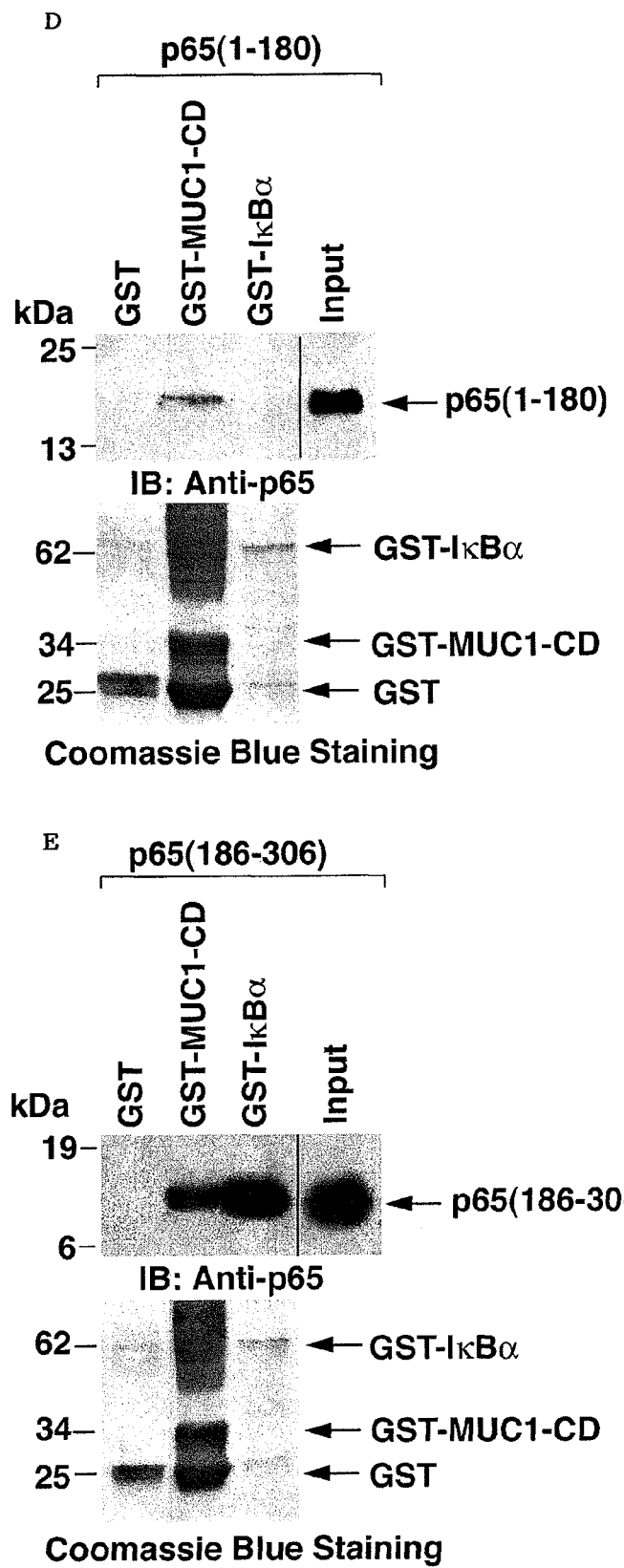
FIG. 7D-E

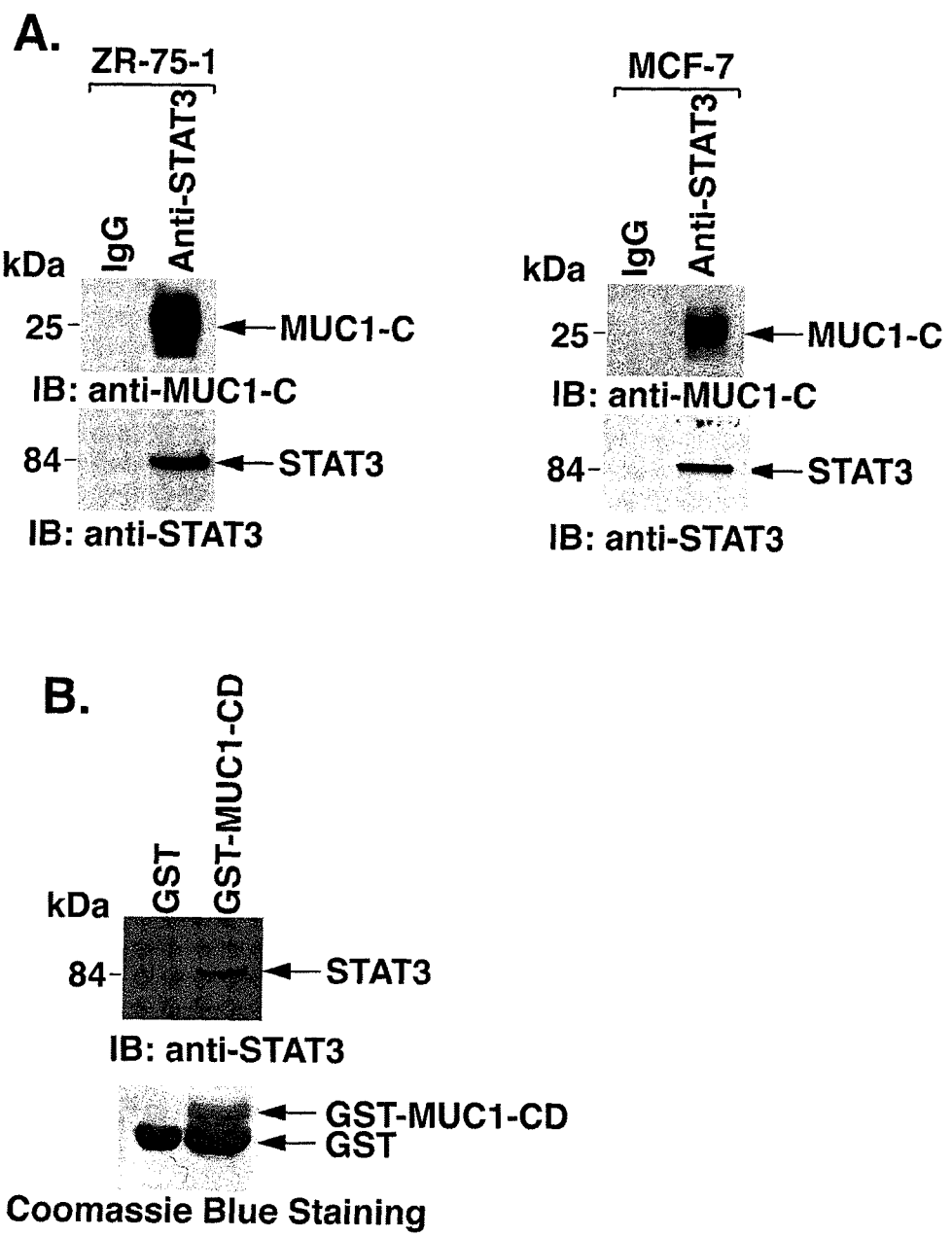
FIG. 9A-B

C.
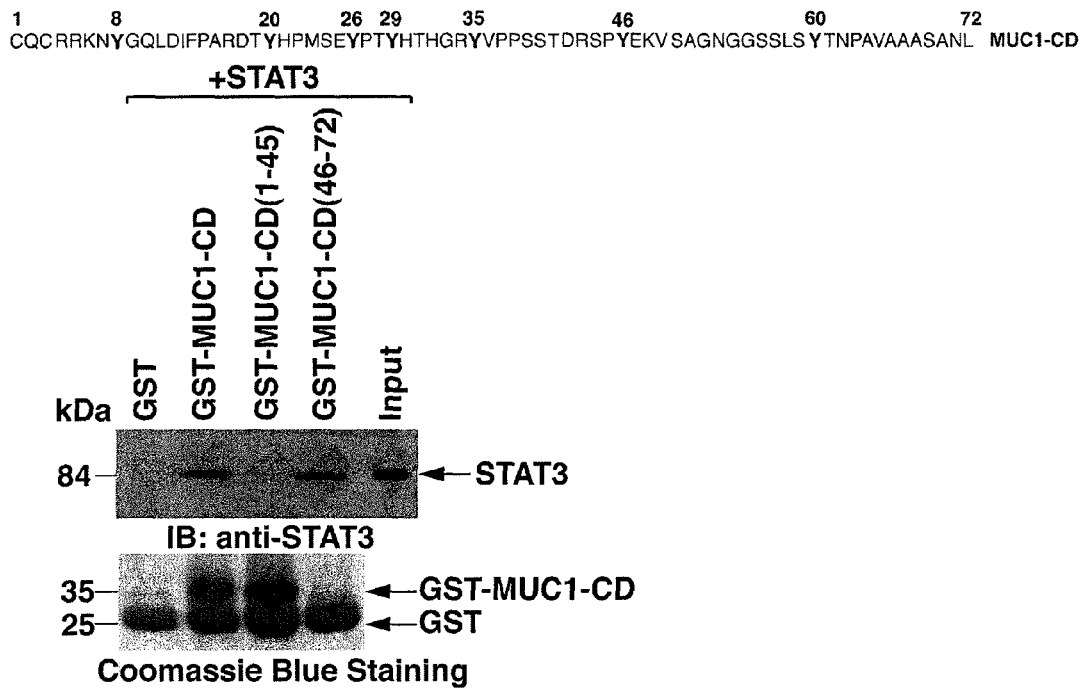
D.
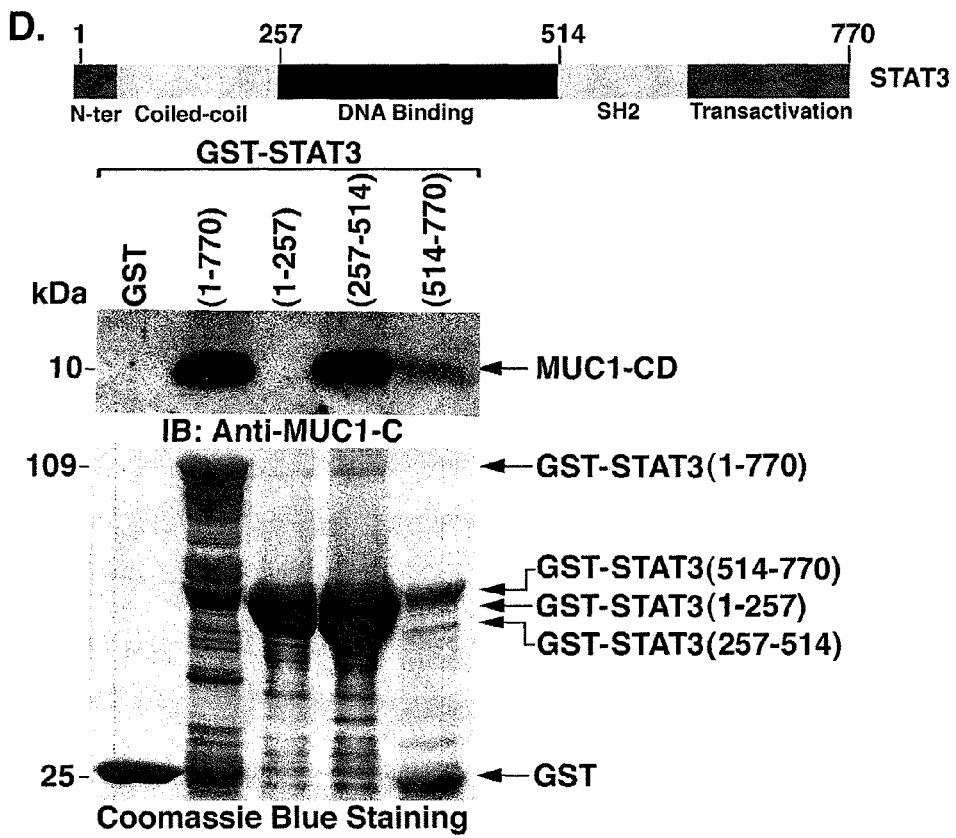
FIG. 9C-D

A. ZR-75-1
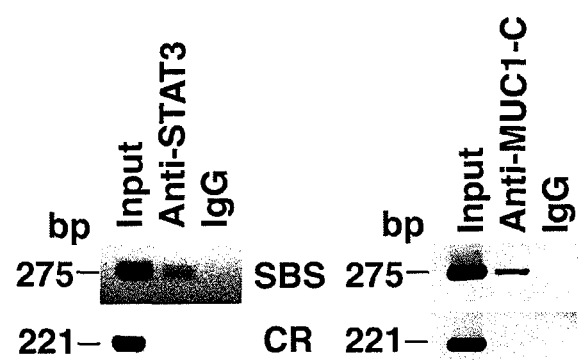
B. MCF-7
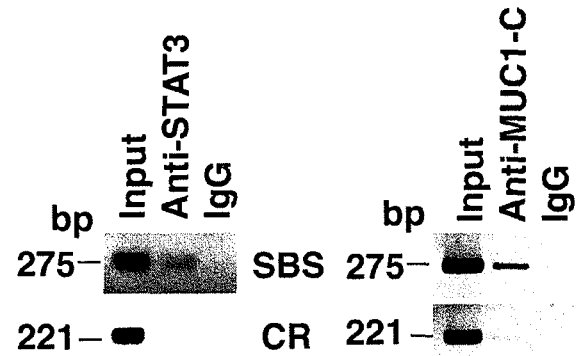
FIG. 10A-B

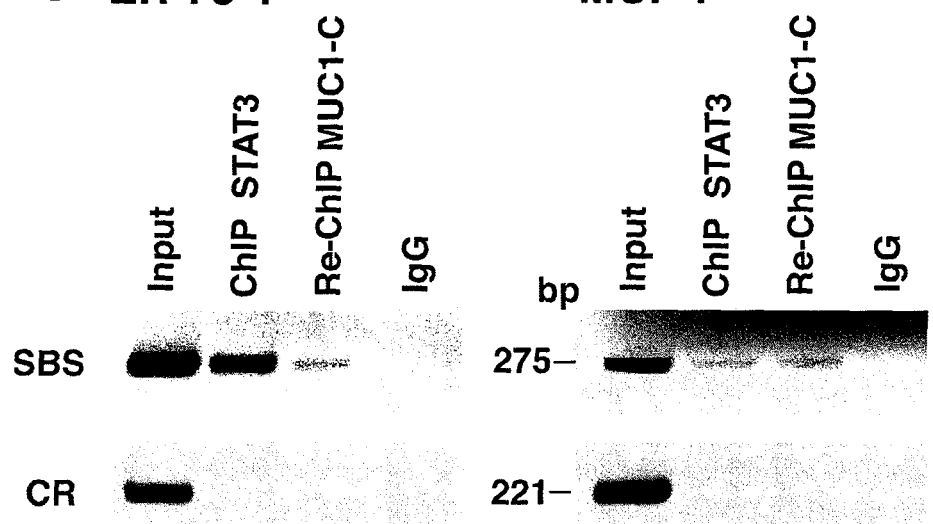
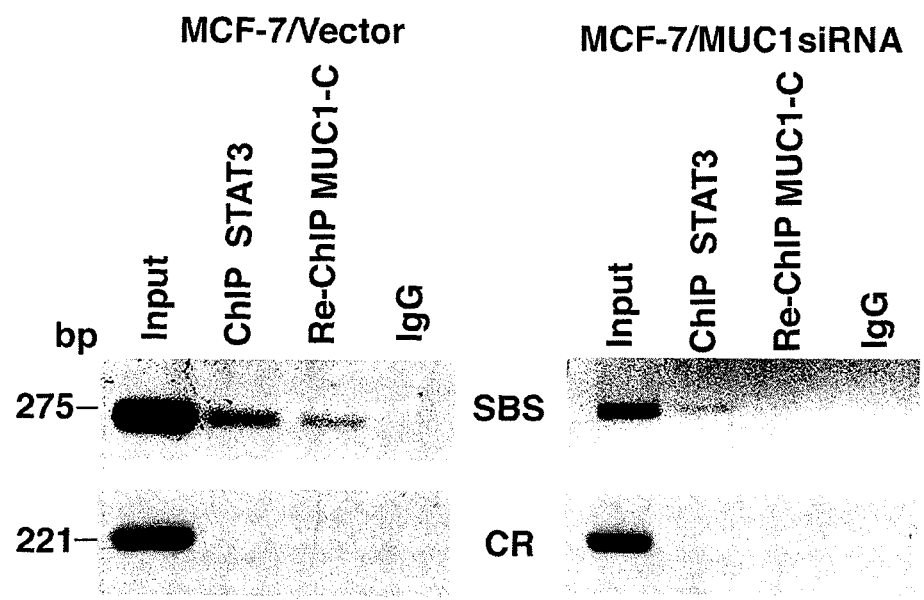
FIG. 10C-D

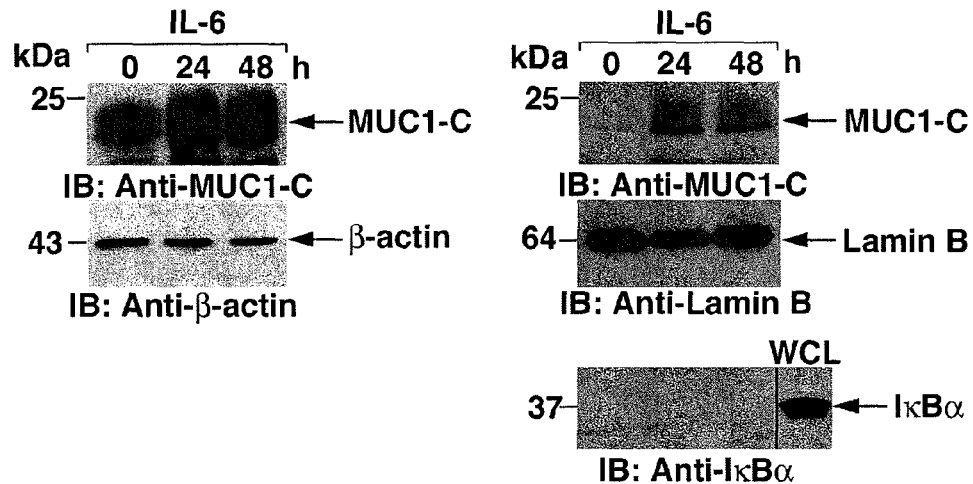
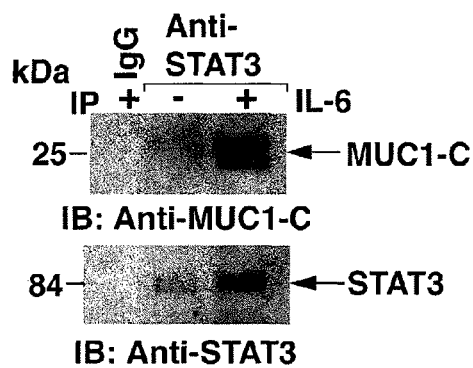
FIG. 11A-B

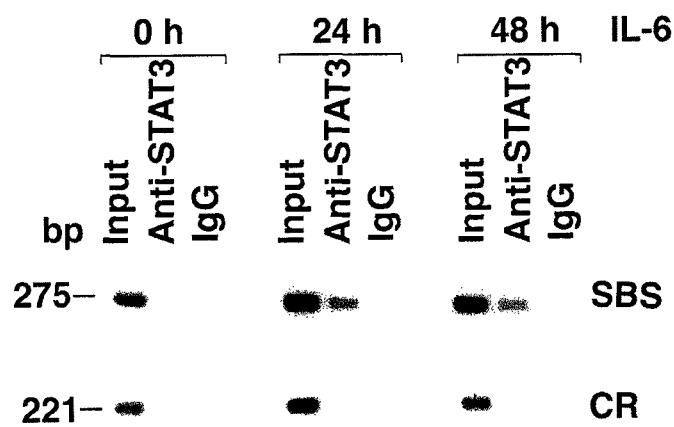
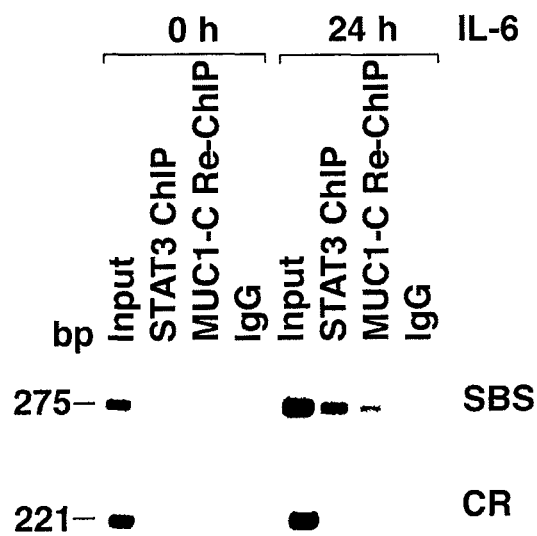
FIG. 11C-D

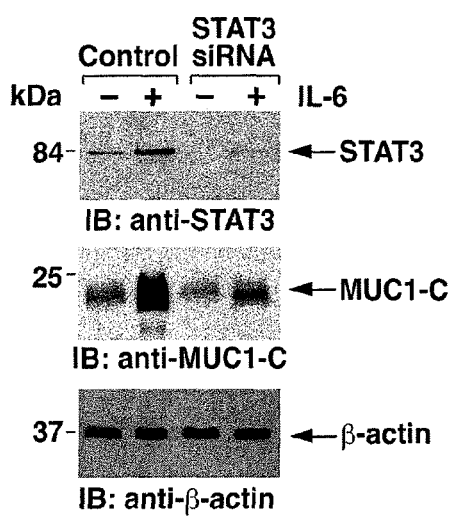
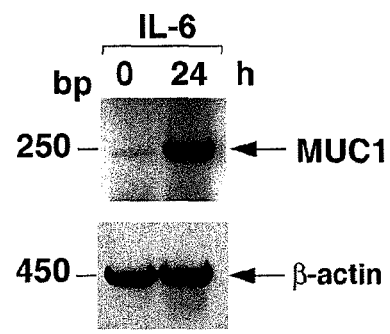
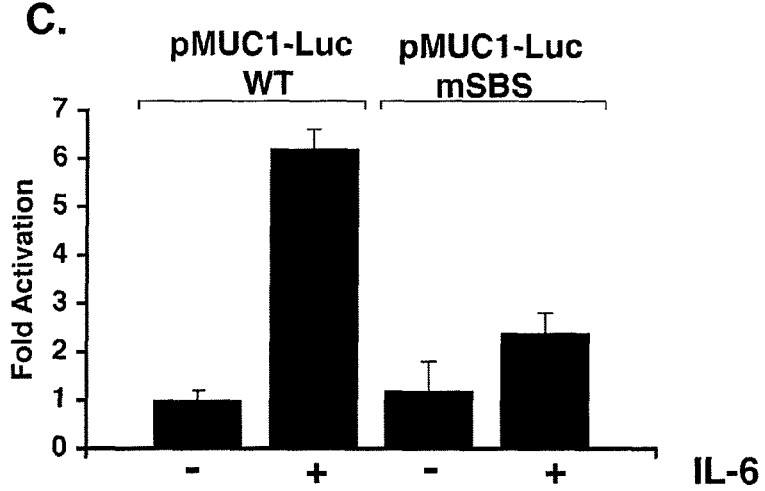
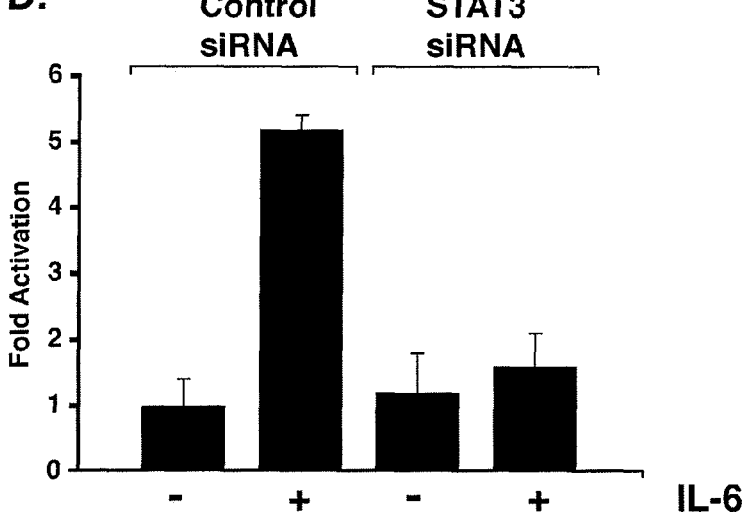
FIG. 12A-D

A. MCF-10A
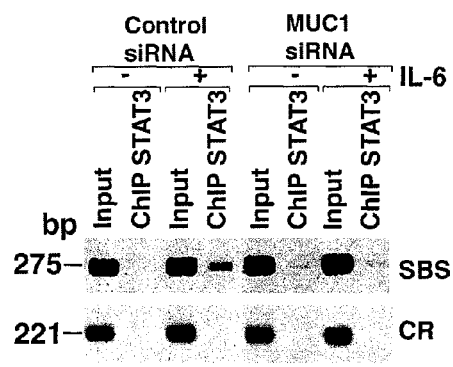
B. MCF-10A
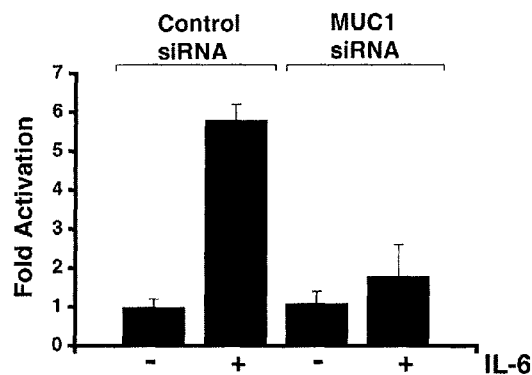
C. ZR-75-1
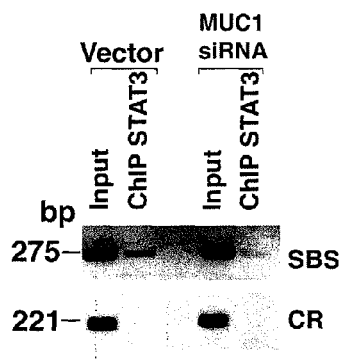
D. ZR-75-1
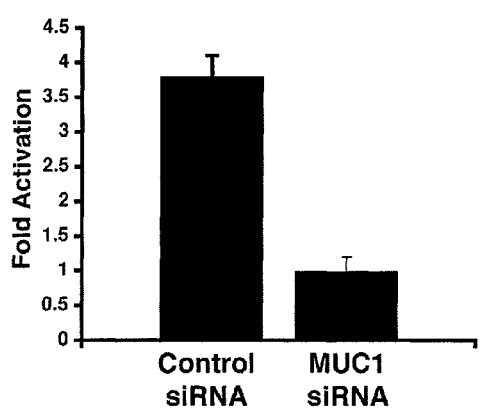
FIG. 13A-D

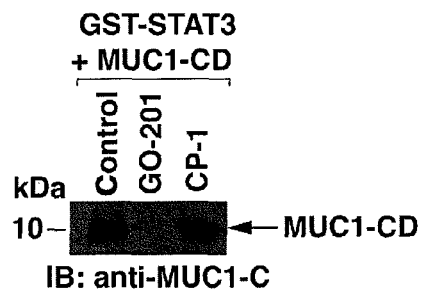
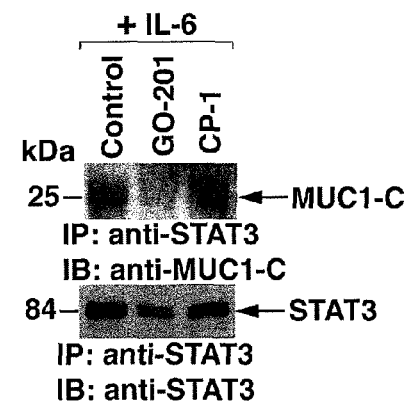
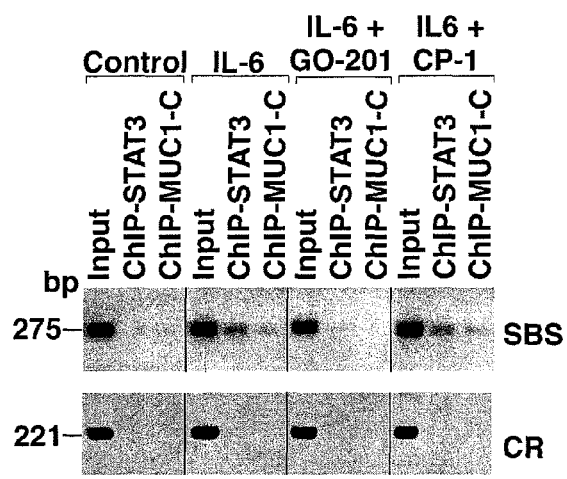
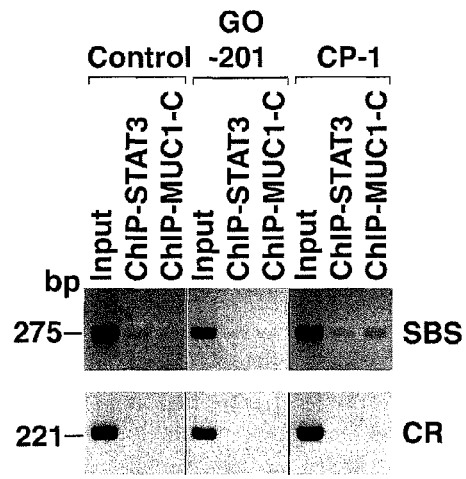
FIG. 14A-D

MUC1-CD

CQCRRKNYGQLDIFPARDTYHPMSEYPTYHTHGRYVPPSSTDRSPYEKVSAGNGGSSLYTNPAVAAASL
(SEQ ID NO:62)

|  |  |  | SEQ ID NOS: |
|---|---|---|---|
| Endogenous | A I V Y L I A L A V C Q C R R K N Y G |  | 55 |
| GO-200-1B | Ac-A I V Y L-*S5*-A L A-*S5*-C Q C-R-R K N Y G-NH2 |  | 56 |
| GO-200-2B | Ac-A K K Y L-*S5*-A L A-*B5*-C Q C-*S5*-R K N Y –NH2 |  | 57 |
| GO-201 | *NH2*-[*dR*]$_9$- C Q C R R K N Y G Q L D I F P –*COOH* | TFA | 3 |
| GO-202 | *NH2*-[*dR*]$_9$- C Q C R R K N –*COOH* | TFA | 53 |
| GO-203 | *NH2*-[*dR*]$_9$- *dC dQ dC dR dR dK dN*-*COOH* | TFA | 53 |
| GO-203-1 | *Acetyl*- [*dR*]$_9$ - *dC dQ dC dR dR dK dN* –*NH2* | TFA | 53 |
| GO-203-2 | *Acetyl*- [*dR*]$_9$ - *dC dQ dC dR dR dK dN* –*NH2* | HCL | 53 |
| GO-203a | *NH2-dR- dR- dR - dC dQ dC dR dR dK dN dR -COOH* | TFA | 58 |
| GO-203b | *NH2-dR- dR- dC dQ dC dR dR dK dN dR -COOH* | TFA | 58 |
| GO-203c | *Acetyl-dR- dR - dC dQ dC dR dR dK dN- NH2* | TFA | 53 |
| GO-203-cyc | *Acetyl*- [*dR*]$_9$ - *dC dQ dC dR dR dK dN* –*NH2* | TFA | 53 |
| GO-203-cyc-1 | *Acetyl-dR- dR - dC dQ dC dR dR dK dN- NH2* | TFA | 53 |
| GO-204 | *NH2- dC dQ dC dR dR dK dN*-[*dR*]9 -*COOH* | TFA | 53 |
| GO-205 | *Acetyl*- [*dR*]$_9$ - *dN dK dR dR dC dQ dC* –*NH2* | TFA | 59 |
| GO-206 | *NH2- dN dK dR dR dC dQ dC*--[*dR*]9 -*COOH* | TFA | 59 |
| GO-207 | *NH2*-[*dR*]$_9$- *dC dQ dC dR dR dK* -*COOH* | TFA | 4 |
| GO-208 | *NH2*-[*dR*]$_9$- *dC dQ dC dR dR* -*COOH* | TFA | 50 |
| GO-209 | *NH2*-[*dR*]$_9$- *dC dQ dC dR* -*COOH* | TFA | 54 |
| GO-210 | *NH2*-[*dR*]$_9$- *dC dQ dC-COOH* | TFA |  |
| CP-1 | *NH2*-[*dR*]$_9$- A Q A R R K N Y G Q L D I F P –*COOH* | TFA | 60 |
| CP-2 | *NH2*-[*dR*]$_9$- *dA dQ dA dR dR dK dN-COOH* | TFA | 61 |

FIG. 15

INHIBITION OF INFLAMMATION USING ANTAGONISTS OF MUC1

This application claims benefit of priority to U.S. Provisional Application Ser. No. 61/181,530, filed May 27, 2009, U.S. Provisional Application Ser. No. 61/253,730, filed Oct. 21, 2009, and U.S. Provisional Application Ser. No. 61/303,997, filed Feb. 12, 2010, the entire contents of each of the foregoing applications being incorporated by reference.

BACKGROUND OF THE INVENTION

1. Field of the Invention

This invention relates to regulation of inflammatory signaling. In particular, MUC1 peptides derived from a particular region of the MUC1 cytoplasmic domain have been shown to inhibit MUC1 interaction with NF-κB, and thus inhibit NF-κB-mediated inflammatory signaling. In addition, similar effects against STAT3-mediated inflammatory signaling have been demonstrated.

2. Related Art

The NF-κB proteins (RelA/p65, RelB, c-Rel, NF-κB1/p50 and NF-κB2/p52) are ubiquitously expressed transcription factors. In the absence of stimulation, NF-κB proteins localize to the cytoplasm in complexes with IκBα and other members of the IκB family of inhibitor proteins (Hayden & Ghosh, 2008). Phosphorylation of IκBα by the high molecular weight IκB kinase (IKKα, IKKβ, IKKγ) complex induces ubiquitination and degradation of IκBα and thereby release of NF-κB for nuclear translocation. In turn, activation of NF-κB target genes contributes to tumor development through regulation of inflammatory responses, cellular proliferation and survival (Karin & Lin, 2002). NF-κB p65, like other members of the family, contains an N-terminal Rel homology domain (RHD) that is responsible for dimerization and DNA binding. The RHD also functions as a binding site for ankyrin repeats in the IκBα protein, which blocks the NF-κB p65 nuclear localization signal (NLS). The NF-κB-IκBα complexes shuttle between the nucleus and cytoplasm (Hayden & Ghosh, 2008). Activation of the canonical NF-κB pathway, for example in the cellular response to tumor necrosis α (TNFα), induces IKKβ-mediated phosphorylation of IκBα and its degradation, with a shift in the balance of NF-κB p65 to the nucleus. The nuclear NF-κB dimers engage κB consensus sequences, as well as degenerate variants, in promoter and enhancer regions (Hoffman et al., 2006; Gilmore, 2008). Activation of NF-κB target genes is then further regulated by posttranslational modification of NF-κB p65 and its interaction with transcriptional coactivators (Hayden & Ghosh, 2008). One of the many NF-κB target genes is IκBα, the activation of which results in de novo synthesis of IκBα and termination of the NF-κB transcriptional response.

Mucins are extensively O-glycosylated proteins that are predominantly expressed by epithelial cells. The secreted and membrane-bound mucins form a physical barrier that protects the apical borders of epithelial cells from damage induced by toxins, microorganisms and other forms of stress that occur at the interface with the external environment. The transmembrane mucin 1 (MUC1) can also signal to the interior of the cell through its cytoplasmic domain. MUC1 has no sequence similarity with other membrane-bound mucins, except for the presence of a sea urchin sperm protein-enterokinase-agrin (SEA) domain (Duraisamy et al., 2006). In that regard, MUC1 is translated as a single polypeptide and then undergoes autocleavage at the SEA domain JBC, 1992; Macao, 2006).

The transmembrane MUC1 C-terminal subunit (MUC1-C) functions as a receptor (Ramasamy et al., 2007) and contains a 72-amino acid cytoplasmic domain (MUC1-CD) that is sufficient for inducing transformation (Huang et al., 2005). The MUC1-C subunit is also targeted to the nucleus by a process dependent on its oligomerization (Leng et al., 2007). MUC1-CD functions as a substrate for phosphorylation by the epidermal growth factor receptor (Li et al. 2001), c-Src (Li et al., 2001), glycogen synthase kinase 3β (GSK3β) (Li et al., 1998) and c-Abl (Ahmad et al., 2006). MUC1-CD also stabilizes the Wnt effector, β-catenin, through a direct interaction and thereby contributes to transformation (Huang et al., 2005). Other studies have demonstrated that MUC1-CD interacts directly with IKKβ and IKKγ, and contributes to activation of the IKK complex (Ahmad et al., 2007). Significantly, constitutive activation of NF-κB p65 in human carcinoma cells is downregulated by silencing MUC1, indicating that MUC1-CD has a functional role in regulation of the NF-κB p65 pathway (Ahmad et al., 2007). These findings have also suggested that MUC1-CD function could be targeted with small molecules to disrupt NF-κB signaling in carcinoma cells. However, to date, there are no reports of MUC1 antagonists that impact the signaling of NF-κB.

Members of the signal transducer and activator of transcription (STAT) family also have been implicated in transformation, tumor cell survival, invasion and metastasis (Yu and Jove, 2004). The STAT3 transcription factor was identified as an effector of the interleukin-6 (IL-6) inflammatory response (Wegenka, 1994). STAT3 is activated by Janus-activated kinase (JAK)-1 phosphorylation of the IL-6 receptor, recruitment of STAT3 and then phosphorylation of STAT3 on a conserved tyrosine at position 705 (Yu and Jove, 2004). Activation of the epidermal growth factor receptor is also associated with direct phosphorylation of STAT3 on Tyr-705. In turn, phosphorylated STAT3 undergoes dimerization, translocates to the nucleus and induces activation of STAT3 target genes, which encode regulators of cell cycle progression (cyclin D1 and c-Myc) and inhibitors of apoptosis (survivin and Bcl-xL) (Alvarez, 2005; Alvarez, 2006). Activated STAT3 induces transformation (Bromberg, 1999). Moreover, STAT3 activation has been detected in diverse carcinomas and hematologic malignancies (Aaronson and Horvath, 2002; Bowman, 2000; Yu and Jove, 2004), consistent with involvement of STAT3 in the transcription of genes that control growth and survival. In this regard, small molecule inhibitors of the JAK-1→STAT3 pathway have anti-cancer activity in vitro and in animal models (Song, 2005; Siddiquee, 2007; Ahmad, 2008; Germain and Frank, 2007). In addition, aptamers that block EGFR signaling to STAT3 inhibit growth of malignant epithelial and hematologic cells (Buerger, 2003). These findings have collectively supported the importance of the STAT3 pathway in linking inflammation with tumorigenesis.

SUMMARY OF THE INVENTION

Thus, in accordance with the present invention, there is provided a method of inhibiting inflammatory signaling in a MUC1-expressing cell comprising contacting the cell with a MUC1 peptide of at least 4 consecutive MUC1 residues and no more than 20 consecutive MUC1 residues and comprising the sequence CQC, wherein the amino-terminal cysteine of CQC is covered on its $NH_2$-terminus by at least one amino acid residue that need not correspond to the native MUC-1 transmembrane sequence. The peptide may comprise at least 5, 6 or 7 consecutive MUC1 residues, and the sequence may more specifically comprise CQCR (SEQ ID NO:54), CQCRR (SEQ ID NO:50), CQCRRR (SEQ ID NO:51), CQCRRRR (SEQ ID NO:52), CQCRRK (SEQ ID NO:4), or CQCRRKN (SEQ ID NO:53). The peptide may contain no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1.

The MUC1-positive cell may be a tumor cell, an endothelial cell or an inflammatory cell, such as a macrophage, a B cell, at T cell, a dendritic cell, a myeloid-derived suppressor cell, an NK cell or a neutrophil. The peptide may be fused to a cell delivery domain, such as poly-D-R, poly-D-P or poly-D-K. The method may further comprise contacting the cell with a second anti-inflammatory agent, such as a steroid or a COX-2 inhibitor. The second anti-inflammatory agent may be contacted prior to, after, or at the same time as the peptide. The peptide may comprise all L amino acids, all D amino acids or a mix of L and D amino acids. The inflammatory signaling may comprise NF-κB-mediated signaling or STAT-mediated signaling, such as STAT3-mediated signaling. The NF-κB-mediated signaling inflammatory signaling may comprise NF-κB activation of a target gene selected from the group consisting of Bcl-xL and MUC1. The STAT3-mediated inflammatory signaling may comprise STAT3 activation of a target gene selected from the group consisting of Cyclin D1, survivin, Idp1, Idp2, Cdkn1C, Lefty1, Mest, Aes1, Zfp57, Zfp3611, Sh3bp1, Ccnd3 and MUC1.

In another embodiment, there is provided a method of inhibiting MUC1 binding to NF-κB or a STAT comprising in a MUC1-expressing cell comprising contacting the cell with a MUC1 peptide of at least 4 consecutive MUC1 residues and no more than 20 consecutive MUC1 residues and comprising the sequence CQC, wherein the amino-terminal cysteine of CQC is covered on its $NH_2$-terminus by at least one amino acid residue that need not correspond to the native MUC1 transmembrane sequence.

In yet another embodiment, there is provided a method of inhibiting MUC1 competition with IκBα for binding to NF-κB in a MUC1-expressing cell comprising contacting the cell with a MUC1 peptide of at least 4 consecutive MUC1 residues and no more than 20 consecutive MUC1 residues and comprising the sequence CQC, wherein the amino-terminal cysteine of CQC is covered on its $NH_2$-terminus by at least one amino acid residue that need not correspond to the native MUC1 transmembrane sequence.

In still yet another embodiment, there is provided a method of inhibiting MUC1-induced nuclear translocation of NF-κB in a MUC1-expressing cell comprising contacting the cell with a MUC1 peptide of at least 4 consecutive MUC1 residues and no more than 20 consecutive MUC1 residues and comprising the sequence CQC, wherein the amino-terminal cysteine of CQC is covered on its $NH_2$-terminus by at least one amino acid residue that need not correspond to the native MUC1 transmembrane sequence.

In a further embodiment, there is provided a method of inhibiting an inflammatory response in a subject comprising administering to the subject a MUC1 peptide of at least 4 consecutive MUC1 residues and no more than 20 consecutive MUC1 residues and comprising the sequence CQC (SEQ ID NO:4), wherein the amino-terminal cysteine of CQC is covered on its $NH_2$-terminus by at least one amino acid residue that need not correspond to the native MUC-1 transmembrane sequence. The peptide may comprise at least 5, 6 or 7 consecutive MUC1 residues, and the sequence may more particularly comprise CQCR (SEQ ID NO: 54), CQCRR (SEQ ID NO: 50), CQCRRR (SEQ ID NO: 51), CQCRRRR (SEQ ID NO: 52), CQCRRK (SEQ ID NO: 4), or CQCRRKN (SEQ ID NO: 53). The peptide may contain no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1.

The inflammatory response may be caused by NF-κB-mediated signaling or STAT-mediated signaling, such as STAT3-mediate signaling. The peptide may be fused to a cell delivery domain, such as poly-D-R, poly-D-P or poly-D-K. Administering may comprise intravenous, intra-arterial, oral, intratumoral, subcutaneous, topical or intraperitoneal administration, or local, regional, systemic, or continual administration. Inhibiting may comprise inhibition or resolution of the inflammatory response. The method may further comprise administering to the subject a second anti-inflammatory therapy, such as a steroid or a COX2 inhibitor. The second anti-inflammatory therapy may be administered prior to, after or at the same time as the peptide. The subject may be a human. The peptide may be administered at 0.1-500 mg/kg/d, or more specifically, at 10-100 mg/kg/d. The peptide my be administered daily, such as for 7 days, 2 weeks, 3 weeks, 4 weeks, one month, 6 weeks, 8 weeks, two months, 12 weeks, or 3 months. The peptide may be administered weekly, such as for 2 weeks, 3 weeks, 4 weeks, 6 weeks, 8 weeks, 10 weeks, or 12 weeks. The peptide may comprise all L amino acids, all D amino acids or a mix of L and D amino acids.

In still a further embodiment, there is provided a pharmaceutical composition comprising (i) a MUC1 peptide of at least 4 consecutive MUC1 residues and no more than 20 consecutive MUC1 residues and comprising the sequence CQC, wherein the amino-terminal cysteine of CQC is covered on its $NH_2$-terminus by at least one amino acid residue that need not correspond to the native MUC-1 transmembrane sequence; and (ii) a second anti-inflammatory agent other than (i). The second anti-inflammatory agent a steroid or COX-2 inhibitor.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed.

FIGS. 1A-D: MUC1-C associates with NF-κB p65. (FIGS. 1A-C) Lysates from the indicated cells were immunoprecipitated with anti-p65 or a control IgG. The precipitates were immunoblotted with anti-MUC1-C and anti-p65. (FIG. 1D) Lysates from ZR-75-1 cells were incubated with GST or GST-MUC1-CD bound to glutathione beads. The adsorbates were immunoblotted with anti-p65. Input of the GST proteins was assessed by Coomassie blue staining. Sequence in FIG. 1B is SEQ ID NO: 1; sequences in FIG. 1D are SEQ ID NO: 59 ("peptide"), SEQ ID NO: 60 ("A") and SEQ ID NO: 61 ("B").

FIGS. 2A-D: MUC1 attenuates binding of IκBα and NF-κB p65. (FIGS. 2A-C) Cytosolic lysates from the indicated ZR-75-1//vector, ZR-75-1/MUC1siRNA (FIG. 2A), HeLa/vector, HeLa/MUC1 (FIG. 2B), 3Y1/vector and 3Y1/MUC1-CD (FIG. 2C) cells were immunoprecipitates with anti-p65 or a control IgG. The precipitates were immunoblotted with antibodies against IκBα and p65. (FIG. 2D) GST and GST-IκBα bound to glutathione beads were incubated with p65(186-306) in the absence and presence of increasing amounts of MUC1-CD. The adsorbates were immunoblotted with anti-p65 (upper). Input of the MUC1-CD was assessed by immunoblotting with anti-MUC1-C (middle). Input of the GST and GST-IκBα proteins was assessed by Coomassie blue staining (lower).

FIGS. 3A-D: MUC1-C promotes occupancy of NF-κB p65 on the Bcl-xL gene promoter. (FIG. 3A) ZR-75-1/vector and ZR-75-1/MUC1 siRNA cells were fixed and double stained with anti-MUC1-C (green) and anti-NF-κB p65 (red). Nuclei were stained with TO-PRO-3. (FIGS. 3B and 3C) Soluble chromatin from ZR-75-1/vector, ZR-75-1/MUC1siRNA (FIG. 3B), HeLa/vector and HeLa/MUC1 (FIG. 3C) cells was immunoprecipitated with anti-p65 or a control IgG. The final DNA extractions were amplified by PCR with pairs of primers that cover the NF-κB-RE (−597 to −304) or control region (−1001 to −760) in the Bcl-xL promoter. (FIG. 3D) Soluble chromatin from ZR-75-1 cells was immunoprecipitated with anti-MUC1-C or a control IgG and analyzed for Bcl-xL NF-κB-RE or control region sequences (left). In Re-ChIP experiments, the anti-MUC1-C precipitates were released, reimmunopreciptiated with anti-p65 and then analyzed for Bcl-xL promoter sequences (right).

FIGS. 4A-D: MUC1-C interacts with NF-κB p65 in the response of MCF-10A cells to TNFα. (FIG. 4A) MCF-10A cells were stimulated with 20 ng/ml TNFα for the indicated times. Lysates were immunoblotted with anti-MUC1-C and anti-β-actin. (FIG. 4B) Lysates from MCF-10A cells left untreated or stimulated with 20 ng/ml TNFα for 24 h were subjected to immunoprecipitation with anti-p65 or a control IgG. The precipitates were immunoblotted with the indicated antibodies. FIG. 4C) soluble chromatin from MCF-10A cells left untreated and stimulated with 20 ng/ml TNFα for 24 h was immunoprecitated with anti-MUC1-C and then analyzed for MUC1 NF-κB binding motif promoter sequences. (FIG. 4D) In Re-ChIP experiments, the anti-MUC1-C precipitates were released, reimmunoprecipitated with anti-p65 and then analyzed for MUC1 NF-κB binding motif promoter sequences.

FIGS. 5A-D: MUC1-C promotes NF-κB p65-mediated activation of the MUC1 promoters. (FIGS. 5A and 5B) MCF-10A cells were transfected with control or p65 siRNA pools for 72 h. The transfected cells were left untreated or stimulated with TNFα for 24 h. Lysates were immunoblotted with the indicated antibodies (FIG. 5A). The cells were then transfected to express a NF-κB-Luc reporter or a MUC1 promoter-Luc reporter (pMUC1-Luc) and, as a control, the SV-40-Renilla-Luc plasmid (FIG. 5B). (FIGS. 5C and 5D) MCF-10A cells were transfected with control or MUC1 siRNA pools for 72 h. The transfected cells were left untreated or stimulated with TNFα for 24 h. Lysates were immunoblotted with the indicated antibodies (FIG. 5C). The cells were then transfected to express a NF-κB-Luc reporter or a MUC1 promoter-Luc reporter (pMUC1-Luc) and, as a control, the SV-40-Renilla-Luc plasmid (FIG. 5D). Luciferase activity was measured at 48 h after transfection. The results are expressed as the fold-activation (mean±SD from three separate experiments) compared to that obtained with cells transfected with the control siRNA and left untreated (assigned a value of 1).

FIGS. 6A-D. MUC1/CQC peptide blocks the interaction between MUC1 and NF-κB p65. (FIG. 6A). Sequence of the MUC1/CQC (GO-201; SEQ ID NO: 3) and MUC1/AQA (CP-1; SEQ ID NO: 62) peptides with the poly-dArg transduction domain. GST-MUC1-CD was incubated with purified NF-κB p65 in the presence of MUC1/CQC or MUC1/AQA for 1 h at room temperature. Adsorbates to glutathione beads were immunoblotted with anti-p65 (left). MCF-10A cells were left untreated or stimulated with TNFα in the presence of 5 μM MUC1/CQC or MUC1/AQA peptide added each 24 h for 72 h. Anti-p65 precipitates were immunoblotted with the indicated antibodies (right). (FIGS. 6B and 6C) MCF-10A cells were left untreated or stimulated with TNFα in the presence of 5 μM MUC1/CQC or MUC1/AQA peptide added each 24 h for 72 h. Soluble chromatin was precipitated with anti-MUC1-C (left) or anti-p65 (right) and then analyzed for MUC1 NF-κB binding motif promoter sequences (FIG. 6B). Lysates were immunoblotted with the indicated antibodies (FIG. 6C). (FIG. 6D) Model for the proposed effects of MUC1-C on activation of the NF-κB pathway through interactions with IKKs and p65 in an auto-inductive regulatory loop.

FIGS. 7A-E: MUC1-C cytoplasmic domain binds to NF-κB p65 and to the p65 RHD. (FIGS. 7A-B) Lysates from the indicated cells were immunoprecipitated with anti-p65 or a control IgG. The precipitates were immunoblotted with anti-MUC1-C and anti-p65. (FIG. 7C) Lysates from ZR-75-1 cells were incubated with GST or GST-MUC1-CD bound to glutathione beads. The adsorbates were immunoblotted with anti-p65. Input of the GST proteins was assessed by Coomassie blue staining. (FIGS. 7D-E) GST, GST-MUC1-CD and GST-IκBα were incubated with purified p65(1-180) (FIG. 7D) or p65 (186-306) (FIG. 7E). The adsorbates and inputs were immunoblotted with anti-p65.

FIGS. 9A-D: MUC1-C binds directly to the STAT3 DBD. (FIG. 9A) Lysates from ZR-75-1 (left) and MCF-7 (right) cells were subjected to immunoprecipitation with anti-STAT3 or a control IgG. The precipitates were immunoblotted with the indicated antibodies. (FIG. 9B) Lysates from ZR-75-1 cells were incubated with GST and GST-MUC1-CD bound to glutathione beads. The adsorbates were immunoblotted with anti-STAT3 Input of the GST and GST-MUC1-CD proteins was assessed by Coomassie blue staining. (FIG. 9C) Amino acid sequence of the MUC1 cytoplasmic domain is shown with the indicated phosphorylation and binding sites. GST, GST-MUC1-CD, GST-MUC1-CD (1-45) and GST-MUC1-CD (46-72) bound to glutathione beads were incubated with purified recombinant STAT3. The adsorbates were immunoblotted with anti-STAT3. Input of the GST and GST-MUC1-CD fusion proteins was assessed by Coomassie blue staining. (FIG. 9D) Structure of STAT3. GST, GST-STAT3 (full length; amino acids 1-770), GST-MUC1-CD (N-terminal: amino acids 1-257), GST-MUC1-CD (DBD; amino acids 257-514) and GST-MUC1-CD (C-terminal; amino acids 514-770) bound to glutathione beads were incubated with purified MUC1-CD. Adsorbates were immunoblotted with anti-MUC1-C. Input of the GST and GST-STAT3 fusion proteins was assessed by Coomassie blue staining.

FIGS. 10A-D. MUC1-C associates with the STAT3 transcription complex. (FIGS. 10A-B). Schema of the MUC1 promoter region with positioning of the STAT binding site (SBS). Soluble chromatin from ZR-75-1 (FIG. 10A) and MCF-7 (FIG. 10B) cells was immunoprecipitated with anti-STAT3 (left) and anti-MUC1-C (right). The final DNA extractions were amplified by PCR with pairs of primers that cover the STAT binding site (SBS; −689 to −414) and the control region (CR; +4524 to +4745 in the MUC1 promoter. (FIGS. 10C-D) Soluble chromatin from the indicated cells was precipitated with anti-STAT3 and analyzed for MUC1 promoter SBS and CR sequences. In the re-ChIP experiments, anti-STAT3 precipitates were released, reimmunoprecipitated with anti-MUC1-C and then analyzed for MUC 1 promoter sequences.

FIGS. 11A-D: MUC1-C interacts with STAT3 in the response of MCF-10A cells to IL-6. (FIG. 11A) MCF-10A cells were stimulated with IL-6 for the indicated times. Whole cell lysates (left) and nuclear lysates (right) were immunoblotted with the indicated antibodies. (FIG. 11B) MCF-10A cells were stimulated with IL-6 for 24 h. Lysates were immunoprecipitated with anti-STAT3 and a control IgG. The precipitates were immunoblotted with the indicated antibodies. (FIG. 11C) Soluble chromatin from MCF-10A cells stimulated with IL-6 for the indicated times was precipitated with anti-STAT3 and a control IgG. The precipitates were analyzed for MUC1 promoter SBS and CR sequences. (FIG. 11D) Soluble chromatin from control and IL-6-stimulated MCF-10A cells was precipitated with anti-STAT3 and analyzed for MUC1 promoter SBS and CR sequences. In the re-ChIP experiments, anti-STAT3 precipitates were released, reimmunoprecipitated with anti-MUC1-C and then analyzed for MUC1 promoter sequences.

FIGS. 12A-D: Activation of the MUC1 promoter by IL-6 is mediated by STAT3. (FIGS. 12A and B) MCF-10A cells were transfected with control or STAT3 siRNA pools for 72 h. The transfected cells were then left untreated or stimulated with IL-6 for 24 h. Lysates were immunoblotted with the indicated antibodies (FIG. 12A). The cells were then transfected to express a MUC1 promoter-Luc reporter (pMUC1-Luc) and the Renilla-Luc plasmid. Luciferase activity was measured at 48 h after transfection (FIG. 12B). The results are expressed as the fold-activation (mean±SD from three separate experiments) compared to that obtained with cells transfected with control siRNA and left untreated (assigned a value of 1). (FIG. 12C) MCF-10A were transfected to express pMUC1-Luc, which was wild-type or mutated at the STAT binding site (mSBS), and Renilla-Luc. After 24 h, the cells were left untreated or stimulated with IL-6 for 24 h and then assayed for luciferase activity The results are expressed as the fold-activation (mean±SD from three separate experiments) compared to that obtained with cells transfected with wild-type pMUC1-Luc and left untreated (assigned a value of 1). (FIG. 12D) MCF-10A were treated with control or STAT3 siRNA. After 24 h, the cells were left untreated or stimulated with IL-6 for 24 h and then assayed for luciferase activity The results are expressed as the fold-activation (mean±SD from three separate experiments) compared to that obtained with cells transfected with control siRNA and left untreated (assigned a value of 1).

FIGS. 13A-D: MUC1-C promotes STAT3 occupancy of the MUC1 promoter. (FIGS. 13A and B) MCF-10A cells were transfected with control or MUC1 siRNA pools for 72 h. The transfected cells were then left untreated or stimulated with IL-6 for 24 h. Soluble chromatin was precipitated with anti-STAT3 and analyzed for MUC1 promoter SBS and CR sequences (FIG. 13A). The cells were then transfected to express a MUC1 promoter-Luc reporter (pMUC1-Luc) and the Renilla-Luc plasmid. Luciferase activity was measured at 48 h after transfection (FIG. 13B). The results are expressed as the fold-activation (mean±SD from three separate experiments) compared to that obtained with cells transfected with control siRNA and left untreated (assigned a value of 1). (FIG. 13C) Soluble chromatin from ZR-75-1/vector and ZR-75-1/MUC1 siRNA cells was precipitated with anti-STAT3 and analyzed for MUC1 promoter SBS and CR sequences. (FIG. 13D) ZR-75-1/vector and ZR-75-1/MUC1 siRNA cells were transfected to express pMUC1-Luc and Renilla-Luc. Luciferase activity was measured at 48 h after transfection. The results are expressed as the fold-activation (mean±SD from three separate experiments) compared to that obtained with ZR-75-1/MUC1siRNA cells (assigned a value of 1).

FIGS. 14A-D: GO-201 blocks the interaction between MUC1-C and STAT3 in IL-6-stimulated MCF-10A cells. (FIG. 14A) GST-STAT3 was incubated with purified MUC1-CD in the presence of GO-201 or CP-1 for 1 h at room temperature. Adsorbates to glutathione beads were immunoblotted with anti-MUC1-C. (FIGS. 14B-C). MCF-10A cells were stimulated with IL-6 in the presence of 5 mM GO-201 or CP-1 added each 24 h for 72 h. Anti-STAT3 precipitates were immunoblotted with the indicated antibodies (FIG. 14B). Soluble chromatin was precipitated with anti-STAT3 or anti-MUC1-C and analyzed for MUC1 promoter SBS and CR sequences (FIG. 14C). (FIG. 14D) pMUC1-Luc.

FIG. 15: Sequences of MUC1-CD Stapled Peptides.

DESCRIPTION OF ILLUSTRATIVE EMBODIMENTS

Figure 8:
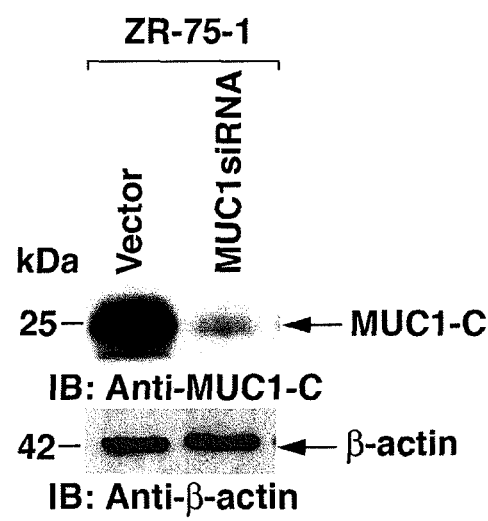
FIG. 8: Silencing of MUC1 in ZR-75-1 breast cancer cells. The BLOCK-iT Target Screening System (Invitrogen) was used to generate small interfering RNAs (siRNA) that target the MUC1 sequence (AAGTTCAGTGCCCAGCTCTAC (SEQ ID NO:55)) and a control sequence (CGCTTACCGAT-TCAGAATGG (SEQ ID NO:56)). The siRNA cassettes were used for the generation of lentiviruses as described (Kawano et al., 2007). The ZR-75-1 cells were infected with the lentiviruses at a multiplicity of infection of 5 in the presence of polybrene (Sigma). Cell clones were selected for expression of EGFP. Lysates were subjected to immunoblotting with the indicated antibodies.

MUC1 has been studied extensively by the inventors and others for its role in cancer. As discussed above, human MUC1 is heterodimeric glycoprotein, translated as a single polypeptide and cleaved into N- and C-terminal subunits in the endoplasmic reticulum (Ligtenberg et al., 1992; Macao et al., 2006; Levitin et al., 2005). Aberrant overexpression of MUC1, as found in most human carcinomas (Kufe et al., 1984), confers anchorage-independent growth and tumorigenicity (Li et al., 2003a; Huang et al., 2003; Schroeder et al., 2004; Huang et al., 2005). Other studies have demonstrated that overexpression of MUC1 confers resistance to apoptosis induced by oxidative stress and genotoxic anti-cancer agents (Yin and Kufe, 2003; Ren et al., 2004; Raina et al., 2004; Yin et al., 2004; Raina et al., 2006; Yin et al., 2007).

The family of tethered and secreted mucins functions in providing a protective barrier of the epithelial cell surface. With damage to the epithelial layer, the tight junctions between neighboring cells are disrupted, and polarity is lost as the cells initiate a heregulin-induced repair program (Vermeer et al., 2003). MUC1-N is shed from the cell surface (Abe and Kufe, 1989), leaving MUC1-C to function as a transducer of environmental stress signals to the interior of the cell. In this regard, MUC1-C forms cell surface complexes with members of the ErbB receptor family, and MUC1-C is targeted to the nucleus in the response to heregulin stimulation (Li et al., 2001; Li et al., 2003c). MUC1-C also functions in integrating the ErbB receptor and Wnt signaling pathways through direct interactions between the MUC1 cytoplasmic domain (CD) and members of the catenin family (Huang et al., 2005; Li et al., 2003c; Yamamoto et al., 1997; Li et al., 1998; Li et al., 2001; Li and Kufe, 2001). Other studies have demonstrated that MUC1-CD is phosphorylated by glycogen synthase kinase 3β, c-Src, protein kinase Cδ, and c-Abl (Raina et al., 2006; Li et al., 1998; Li et al., 2001; Ren et al., 2002).

The mechanisms responsible for nuclear targeting of MUC1-C are unclear. Proteins containing a classical nuclear localization signal (NLS) are imported into the nucleus by first binding to importin α and then, in turn, importin β (Weis, 2003). The cargo-importin α/β complex docks to the nuclear pore by binding to nucleoporins and is transported through the pore by a mechanism dependent on the Ran GTPase. Classical NLSs are monopartite with a single cluster of 4-5 basic amino acids or bipartite with two clusters of basic amino acids separated by a linker of 10-12 amino acids. MUC1-CD contains a RRK motif that does not conform to a prototypical monopartite NLS (Hodel et al., 2002). However, certain proteins containing non-classical NLSs are transported through the nuclear pore by binding directly to importin β (Kau et al., 2004). Importin β associates with several nucleoporins (Ryan and Wente, 2000), including Nup62, which is located on both the cytoplasmic and nucleoplasmic faces of nuclear pore complexes (Percipalle et al., 1997). Other studies have indicated that β-catenin is imported into the nucleus by an importin- and nucleoporin-independent mechanism (Suh and Gumbiner, 2003).

In 2006, the inventors reported that MUC1 is imported into the nucleus by a mechanism involving binding to Nup62 (Leng et al., 2007). They also demonstrate that MUC1 forms oligomers through a CQC motif in the MUC1 cytoplasmic domain and that MUC1 oligomerization is necessary for nuclear import. In 2007, they also demonstrated that overexpression of MUC1 in human carcinoma cells is associated with constitutive activation of NF-kappaB p65 (Ahmad et al. 2007). MUC1 was shown to interact with the high-molecular-weight IκB kinase (IKK) complex in vivo, and that the MUC1 cytoplasmic domain binds directly to IKKβ and IKKγ. Interaction of MUC1 with both IKKβ and IKKγ is necessary for IKKβ activation, resulting in phosphorylation and degradation of IκBα. These findings indicated that MUC1 is important for physiological activation of IKKβ and that overexpression of MUC1, as found in human cancers, confers sustained induction of the IKKβ-NF-κB p65 pathway.

In additional unpublished work, the inventors have extended their research to encompass a further elucidation of the role that the CQC motif plays in oligomer formation. They also have demonstrated that short peptides corresponding to this region are able to disrupt MUC1 oligomer formation, preventing transport into the nucleus of tumor cells. These peptides are able to inhibit tumor cell growth, as well as induce apoptosis in such cells and even necrosis of tumor tissue.

Given the emerging role for MUC1 in inflammatory disease states, the inventors sought to examine whether these same peptides would find use in treating inflammatory disorders. The present studies demonstrate that MUC1-CD binds directly to NF-κB p65 and blocks the interaction between NF-κB p65 and IκBα. The inventors now show that the MUC1-C subunit associates with NF-κB p65 on the promoters of NF-κB target genes and promotes NF-κB-mediated transcription. The results also demonstrate that an inhibitor of MUC1-C oligomerization blocks the MUC1 interaction with NF-κB p65 and constitutive activation of the inflammatory NF-κB pathway. In addition, a similar interaction with STAT3, another inflammatory signaling factor, has been demonstrated, even further implicating MUC1 in this process.

These and other aspects of the invention are described in greater detail below.

I. MUC1

A. Structure

MUC1 is a mucin-type glycoprotein that is expressed on the apical borders of normal secretory epithelial cells (Kufe et al., 1984). MUC1 forms a heterodimer following synthesis as a single polypeptide and cleavage of the precursor into two subunits in the endoplasmic reticulum (Ligtenberg et al., 1992). The cleavage may be mediated by an autocatalytic process (Levitan et al., 2005). The >250 kDa MUC1 N-terminal (MUC1 N-ter, MUC1-N) subunit contains variable numbers of 20 amino acid tandem repeats that are imperfect with highly conserved variations and are modified by O-linked glycans (Gendler et al., 1988; Siddiqui et al., 1988). MUC1-N is tethered to the cell surface by dimerization with the ~23 kDa C-terminal subunit (MUC1 C-ter, MUC1-C), which includes a 58 amino acid extracellular region, a 28 amino acid transmembrane domain and a 72 amino acid cytoplasmic domain (CD; SEQ ID NO:1) (Merlo et al., 1989). The human MUC1 sequence is shown below:

```
                                               (SEQ ID NO: 2)
GSVVVQLTLAFREGTINVHDVETQFNQYKTEAASRYNLTISDVSVSDVP

FPFSAQSGAGVPGWGIALLVLVCVLVALAIVYLIALAVCQCRRKNYGQL

DIFPARDTYHPMSEYPTYHTHGRYVPPSSTDRSPYEKVSAGNGGSSLSY

TNPAVAATSANL
```

The bold sequence indicates the CD, and the underlined portion is an oligomer-inhibiting peptide (SEQ ID NO:3). With transformation of normal epithelia to carcinomas, MUC1 is aberrantly overexpressed in the cytosol and over the entire cell membrane (Kufe et al., 1984; Perey et al., 1992). Cell membrane-associated MUC1 is targeted to endosomes by clathrin-mediated endocytosis (Kinlough et al., 2004). In addition, MUC1-C, but not MUC1-N, is targeted to the nucleus (Baldus et al., 2004; Huang et al., 2003; Li et al., 2003a; Li et al., 2003b; Li et al., 2003c; Wei et al., 2005; Wen et al., 2003) and mitochondria (Ren et al., 2004).

B. Function

MUC1 interacts with members of the ErbB receptor family (Li et al., 2001b; Li et al., 2003c; Schroeder et al., 2001) and with the Wnt effector, β-catenin (Yamamoto et al., 1997). The epidermal growth factor receptor and c-Src phosphorylate the MUC1 cytoplasmic domain (MUC1-CD) on Y-46 and thereby increase binding of MUC1 and β-catenin (Li et al., 2001a; Li et al., 2001b). Binding of MUC1 and β-catenin is also regulated by glycogen synthase kinase 3β and protein kinase Co (Li et al., 1998; Ren et al., 2002). MUC1 colocalizes with β-catenin in the nucleus (Baldus et al., 2004; Li et al., 2003a; Li et al., 2003c; Wen et al., 2003) and coactivates transcription of Wnt target genes (Huang et al., 2003). Other studies have shown that MUC1 also binds directly to p53 and regulates transcription of p53 target genes (Wei et al., 2005). Notably, overexpression of MUC1 is sufficient to induce anchorage-independent growth and tumorigenicity (Huang et al., 2003; Li et al., 2003b; Ren et al., 2002; Schroeder et al., 2004).

Most mitochondrial proteins are encoded in the nucleus and are imported into mitochondria by translocation complexes in the outer and inner mitochondrial membranes. Certain mitochondrial proteins contain N-terminal mitochondrial targeting sequences and interact with Tom20 in the outer mitochondrial membrane (Truscott et al., 2003). Other mitochondrial proteins contain internal targeting sequences and interact with the Tom70 receptor (Truscott et al., 2003). Recent work showed that mitochondrial proteins without internal targeting sequences are delivered to Tom70 by a complex of HSP70 and HSP90 (Young et al., 2003).

II. MUC1 Peptides

A. Structure

The present invention contemplates the design, production and use of various MUC1 peptides. The structural features of these peptides are as follows. First, the peptides have no more than 20 consecutive residues of MUC1. Thus, the term "a peptide having no more than 20 consecutive residues," even when including the term "comprising," cannot be understood to comprise a greater number of consecutive MUC1 residues. Second, the peptides will contain the CQC motif, and may further comprise the CQCR (SEQ ID NO: 54), CQCRR (SEQ ID NO: 50), or CQCRRK (SEQ ID NO: 4) motifs. Thus, the peptides will have, at a minimum, these four, five or six consecutive residues of the MUC1-C domain. Third, the peptides will have at least one amino acid residue attached to the NH$_2$-terminal side of the first C residue in the CQCRRK (SEQ ID NO: 4) motif, such that the first C residue is "covered" by that at least one amino acid attached thereto. This residue may be native to MUC1 (i.e., from the transmembrane domain), may be selected at random (any of the twenty naturally-occuring amino acids or analogs thereof), or may be part of another peptide sequence (e.g., a tag sequence for purification, a stabilizing sequence, or a cell delivery domain).

In general, the peptides will be 50 residues or less, again, comprising no more than 20 consecutive residues of MUC1. The overall length may be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 residues. Ranges of peptide length of 4-50 residues, 7-50 residues, 4-25 residues 7-25, residues, 4-20 residues, 7-20 residues, and 3-15 residues, and 7-15 residues are contemplated. The number of consecutive MUC1 residues may be 3, 4, 5, 6, 7, 8, 9, 10, 11, 12, 13, 14, 15, 16, 17, 18, 19 or 20. Ranges of consecutive residues of 4-20 residues, 5-20 residues, 6-20 residues, 7-20 residues, 4-15 residues, 5-15 residues, 6-15 residues and 7-15 residues are contemplated.

The present invention may utilize L-configuration amino acids, D-configuration amino acids, or a mixture thereof. While L-amino acids represent the vast majority of amino acids found in proteins, D-amino acids are found in some proteins produced by exotic sea-dwelling organisms, such as cone snails. They are also abundant components of the peptidoglycan cell walls of bacteria. D-serine may act as a neurotransmitter in the brain. The L and D convention for amino acid configuration refers not to the optical activity of the amino acid itself, but rather to the optical activity of the isomer of glyceraldehyde from which that amino acid can theoretically be synthesized (D-glyceraldehyde is dextrorotary; L-glyceraldehyde is levorotary).

One form of an "all-D" peptide is a retro-inverso peptide. Retro-inverso modification of naturally occurring polypeptides involves the synthetic assemblage of amino acids with α-carbon stereochemistry opposite to that of the corresponding L-amino acids, i.e., D-amino acids in reverse order with respect to the native peptide sequence. A retro-inverso analogue thus has reversed termini and reversed direction of peptide bonds (NH—CO rather than CO—NH) while approximately maintaining the topology of the side chains as in the native peptide sequence. See U.S. Pat. No. 6,261,569, incorporated herein by reference.

As mentioned above, the present invention contemplates fusing or conjugating a cell delivery domain (also called a cell delivery vector, or cell transduction domain). Such domains are well known in the art and are generally characterized as short amphipathic or cationic peptides and peptide derivatives, often containing multiple lysine and arginine resides (Fischer, 2007). Of particular interest are poly-D-Arg and poly-D-Lys sequences (e.g., dextrorotary residues, eight residues in length).

TABLE 1

| CDD/CTD PEPTIDES | SEQ ID NO |
|---|---|
| QAATATRGRSAASRPTERPRAPARSASRPRRPVE | 5 |
| RQIKIWFQNRRMKWKK | 6 |
| RRMKWKK | 7 |
| RRWRRWWRRWWRRWRR | 8 |
| RGGRLSYSRRRFSTSTGR | 9 |
| YGRKKRRQRRR | 10 |
| RKKRRQRRR | 11 |
| YARAAARQARA | 12 |
| RRRRRRRR | 13 |
| KKKKKKKK | 14 |
| GWTLNSAGYLLGKINLKALAALAKXIL | 15 |
| LLILLRRRIRKQANAHSK | 16 |
| SRRHHCRSKAKRSRHH | 17 |
| NRARRNRRRVR | 18 |
| RQLRIAGRRLRGRSR | 19 |
| KLIKGRTPIKFGK | 20 |
| RRIPNRRPRR | 21 |
| KLALKLALKALKAALKLA | 22 |
| KLAKLAKKLAKLAK | 23 |
| GALFLGFLGAAGSTNGAWSQPKKKRKV | 24 |
| KETWWETWWTEWSQPKKKRKV | 25 |
| GALFLGWLGAAGSTMGAKKKRKV | 26 |
| MGLGLHLLVLAAALQGAKSKRKV | 27 |
| AAVALLPAVLLALLAPAAANYKKPKL | 28 |
| MANLGYWLLALFVTMWTDVGLCKKRPKP | 29 |
| LGTYTQDFNKFHTFPQTAIGVGAP | 30 |
| DPKGDPKGVTVTVTVTGKGDPXPD | 31 |
| PPPPPPPPPPPPPP | 32 |
| VRLPPPVRLPPPVRLPPP | 33 |
| PRPLPPPRPG | 34 |
| SVRRRPRPPYLPRPRPPPFFPPRLPPRIPP | 35 |
| TRSSRAGLQFPVGRVHRLLRK | 36 |
| GIGKFLHSAKKFGKAFVGEIMNS | 37 |
| KWKLFKKIEKVGQNIRDGIIKAGPAVAVVGQATQIAK | 38 |
| ALWMTLLKKVLKAAAKAALNAVLVGANA | 39 |
| GIGAVLKVLTTGLPALISWIKRKRQQ | 40 |

TABLE 1-continued

| CDD/CTD PEPTIDES | SEQ ID NO |
|---|---|
| INLKALAALAKKIL | 41 |
| GFFALIPKIISSPLPKTLLSAVGSALGGSGGQE | 42 |
| LAKWALKQGFAKLKS | 43 |
| SMAQDIISTIGDLVKWIIQTVNXFTKK | 44 |
| LLGDFFRKSKEKIGKEFKRIVQRIKQRIKDFLANLVPRTES | 45 |
| LKKLLKKLLKKLLKKLLKKL | 46 |
| KLKLKLKLKLKLKLKLKL | 47 |
| PAWRKAFRWAWRMLKKAA | 48 |

Also as mentioned above, peptides modified for in vivo use by the addition, at the amino- and/or carboxyl-terminal ends, of a blocking agent to facilitate survival of the peptide in vivo are contemplated. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. These agents can be added either chemically during the synthesis of the peptide, or by recombinant DNA technology by methods familiar in the art. Alternatively, blocking agents such as pyroglutamic acid or other molecules known in the art can be attached to the amino and/or carboxyl terminal residues.

B. Synthesis

It will be advantageous to produce peptides using the solid-phase synthetic techniques (Merrifield, 1963). Other peptide synthesis techniques are well known to those of skill in the art (Bodanszky et al., 1976; Peptide Synthesis, 1985; Solid Phase Peptide Synthelia, 1984). Appropriate protective groups for use in such syntheses will be found in the above texts, as well as in Protective Groups in Organic Chemistry, 1973. These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptides of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

Aside from the twenty standard amino acids can be used, there are a vast number of "non-standard" amino acids. Two of these can be specified by the genetic code, but are rather rare in proteins. Selenocysteine is incorporated into some proteins at a UGA codon, which is normally a stop codon. Pyrrolysine is used by some methanogenic archaea in enzymes that they use to produce methane. It is coded for with the codon UAG. Examples of non-standard amino acids that are not found in proteins include lanthionine, 2-aminoisobutyric acid, dehydroalanine and the neurotransmitter gamma-aminobutyric acid. Non-standard amino acids often occur as intermediates in the metabolic pathways for standard amino acids—for example ornithine and citrulline occur in the urea cycle, part of amino acid catabolism. Non-standard amino acids are usually formed through modifications to standard amino acids. For example, homocysteine is formed through the transsulfuration pathway or by the demethylation of methionine via the intermediate metabolite S-adenosyl methionine, while hydroxyproline is made by a posttranslational modification of proline.

C. Linkers

Linkers or cross-linking agents may be used to fuse MUC1 peptides to other proteinaceous sequences. Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidino-, indole-, or carboxyl-specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

D. Design, Variants and Analogs

In one aspect, the present invention focuses on peptides comprising the sequence CQCRRK (SEQ ID NO: 4). Having identified this key structure in MUC1 oligomer formation, the inventors also contemplate that variants of the CQCRRK (SEQ ID NO: 4) sequence may be employed. For example, certain non-natural amino acids that satisfy the structural constraints of the CQCRRK (SEQ ID NO: 4) sequence may be substituted without a loss, and perhaps with an improvement in, biological function. In addition, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Methods for generating specific structures have been disclosed in the art. For example, α-helix mimetics are disclosed in U.S. Pat. Nos. 5,446,128; 5,710,245; 5,840,833; and 5,859,184. Methods for generating conformationally restricted β-turns and β-bulges are described, for example, in U.S. Pat. Nos. 5,440,013; 5,618,914; and 5,670,155. Other types of mimetic turns include reverse and γ-turns. Reverse turn mimetics are disclosed in U.S. Pat. Nos. 5,475,085 and 5,929,237, and γ-turn mimetics are described in U.S. Pat. Nos. 5,672,681 and 5,674,976.

By "molecular modeling" is meant quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods. Computer programs that use X-ray crystallography data are particularly useful for designing such compounds. Programs such as RasMol, for example, can be used to generate three dimensional models. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures. The methods can involve the additional step of outputting to an output device a model of the 3-D structure of the compound. In addition, the 3-D data of candidate compounds can be compared to a computer database of, for example, 3-D structures.

Compounds of the invention also may be interactively designed from structural information of the compounds described herein using other structure-based design/modeling techniques (see, e.g., Jackson, 1997; Jones et al., 1996). Candidate compounds can then be tested in standard assays familiar to those skilled in the art. Exemplary assays are described herein.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., International Application No. PCT/US99/11913, the disclosure of which is incorporated herein by reference in its entirety). Other molecular modeling techniques may also be employed in accordance with this invention (e.g., Cohen et al., 1990; Navia et al., 1992), the disclosures of which are incorporated herein by reference in their entirety). All these methods produce data that are amenable to computer analysis. Other spectroscopic methods that can also be useful in the method of the invention, but that do not currently provide atomic level structural detail about biomolecules, include circular dichroism and fluorescence and ultraviolet/visible light absorbance spectroscopy. A preferred method of analysis is x-ray crystallography. Descriptions of this procedure and of NMR spectroscopy are provided below.

X-ray Crystallography. X-ray crystallography is based on the diffraction of x-radiation of a characteristic wavelength by electron clouds surrounding the atomic nuclei in a crystal of a molecule or molecular complex of interest. The technique uses crystals of purified biological macromolecules or molecular complexes (but these frequently include solvent components, co-factors, substrates, or other ligands) to determine near atomic resolution of the atoms making up the particular biological macromolecule. A prerequisite for solving 3-D structure by x-ray crystallography is a well-ordered crystal that will diffract x-rays strongly. The method directs a beam of x-rays onto a regular, repeating array of many identical molecules so that the x-rays are diffracted from the array in a pattern from which the structure of an individual molecule can be retrieved. Well-ordered crystals of, for example, globular protein molecules are large, spherical or ellipsoidal objects with irregular surfaces. The crystals contain large channels between the individual molecules. These channels, which normally occupy more than one half the volume of the crystal, are filled with disordered solvent molecules, and the protein molecules are in contact with each other at only a few small regions. This is one reason why structures of proteins in crystals are generally the same as those of proteins in solution.

Methods of obtaining the proteins of interest are described below. The formation of crystals is dependent on a number of different parameters, including pH, temperature, the concentration of the biological macromolecule, the nature of the solvent and precipitant, as well as the presence of added ions or ligands of the protein. Many routine crystallization experiments may be needed to screen all these parameters for the combinations that give a crystal suitable for x-ray diffraction analysis. Crystallization robots can automate and speed up work of reproducibly setting up a large number of crystallization experiments (see, e.g., U.S. Pat. No. 5,790,421, the disclosure of which is incorporated herein by reference in its entirety).

Polypeptide crystallization occurs in solutions in which the polypeptide concentration exceeds its solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Crystallizations are generally carried out between 4° C. and 20° C. Substances known as "precipitants" are often used to decrease the solubility of the polypeptide in a concentrated solution by forming an energetically unfavorable precipitating depleted layer around the polypeptide molecules (Weber, 1991). In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2-4 pentanediol, and many of the polyglycols, such as polyethylene glycol (PEG). The precipitating solutions can include, for example, 13-24% PEG 4000, 5-41% ammonium sulfate, and 1.0-1.5 M sodium chloride, and a pH ranging from 5.0-7.5. Other additives can include 0.1 M Hepes, 2-4% butanol, 20-100 mM sodium acetate, 50-70 mM citric acid, 120-130 mM sodium phosphate, 1 mM ethylene diamine tetraacetic acid (EDTA), and 1 mM dithiothreitol (DTT). These agents are prepared in buffers and are added dropwise in various combinations to the crystallization buffer. Proteins to be crystallized can be modified, e.g., by phosphorylation or by using a phosphate mimic (e.g., tungstate, cacodylate, or sulfate).

Commonly used polypeptide crystallization methods include the following techniques: batch, hanging drop, seed initiation, and dialysis. In each of these methods, it is important to promote continued crystallization after nucleation by maintaining a supersaturated solution. In the batch method, polypeptide is mixed with precipitants to achieve supersaturation, and the vessel is sealed and set aside until crystals appear. In the dialysis method, polypeptide is retained in a sealed dialysis membrane that is placed into a solution containing precipitant. Equilibration across the membrane increases the polypeptide and precipitant concentrations, thereby causing the polypeptide to reach supersaturation levels.

In the preferred hanging drop technique (McPherson, 1976), an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide may form.

Another method of crystallization introduces a nucleation site into a concentrated polypeptide solution. Generally, a concentrated polypeptide solution is prepared and a seed crystal of the polypeptide is introduced into this solution. If the concentrations of the polypeptide and any precipitants are correct, the seed crystal will provide a nucleation site around which a larger crystal forms.

Yet another method of crystallization is an electrocrystallization method in which use is made of the dipole moments of protein macromolecules that self-align in the Helmholtz layer adjacent to an electrode (see, e.g., U.S. Pat. No. 5,597, 457, the disclosure of which is incorporated herein by reference in its entirety).

Some proteins may be recalcitrant to crystallization. However, several techniques are available to the skilled artisan to induce crystallization. For example, the removal of flexible polypeptide segments at the amino or carboxyl terminal end of the protein may facilitate production of crystalline protein samples. Removal of such segments can be done using molecular biology techniques or treatment of the protein with proteases such as trypsin, chymotrypsin, or subtilisin.

In diffraction experiments, a narrow and parallel beam of x-rays is taken from the x-ray source and directed onto the crystal to produce diffracted beams. The incident primary beams cause damage to both the macromolecule and solvent molecules. The crystal is, therefore, cooled (e.g., to between −220° C. and −50° C.) to prolong its lifetime. The primary beam must strike the crystal from many directions to produce all possible diffraction spots, so the crystal is rotated in the beam during the experiment. The diffracted spots are recorded on a film or by an electronic detector. Exposed film has to be digitized and quantified in a scanning device, whereas the electronic detectors feed the signals they detect directly into a computer. Electronic area detectors significantly reduce the time required to collect and measure diffraction data. Each diffraction beam, which is recorded as a spot on film or a detector plate, is defined by three properties: the amplitude, which is measured from the intensity of the spot; the wavelength, which is set by the x-ray source; and the phase, which is lost in x-ray experiments. All three properties are needed for all of the diffracted beams in order to determine the positions of the atoms giving rise to the diffracted beams. One way of determining the phases is called Multiple Isomorphous Replacement (MIR), which requires the introduction of exogenous x-ray scatterers (e.g., heavy atoms such metal atoms) into the unit cell of the crystal. For a more detailed description of MIR, see U.S. Pat. No. 6,093,573 (column 15) the disclosure of which is incorporated herein by reference in its entirety.

Atomic coordinates refer to Cartesian coordinates (x, y, and z positions) derived from mathematical equations involving Fourier synthesis of data derived from patterns obtained via diffraction of a monochromatic beam of x-rays by the atoms (scattering centers) of biological macromolecule of interest in crystal form. Diffraction data are used to calculate electron density maps of repeating units in the crystal (unit cell). Electron density maps are used to establish the positions (atomic coordinates) of individual atoms within a crystal's unit cell. The absolute values of atomic coordinates convey spatial relationships between atoms because the absolute values ascribed to atomic coordinates can be changed by rotational and/or translational movement along x, y, and/or z axes, together or separately, while maintaining the same relative spatial relationships among atoms. Thus, a biological macromolecule (e.g., a protein) whose set of absolute atomic coordinate values can be rotationally or translationally adjusted to coincide with a set of prior determined values from an analysis of another sample is considered to have the same atomic coordinates as those obtained from the other sample.

Further details on x-ray crystallography can be obtained from co-pending U.S. Application No. 2005/0015232, U.S. Pat. No. 6,093,573 and International Application Nos. PCT/US99/18441, PCT/US99/11913, and PCT/US00/03745. The disclosures of all these patent documents are incorporated herein by reference in their entirety.

NMR Spectroscopy

Whereas x-ray crystallography requires single crystals of a macromolecule of interest, NMR measurements are carried out in solution under near physiological conditions. However, NMR-derived structures are not as detailed as crystal-derived structures.

While the use of NMR spectroscopy was until relatively recently limited to the elucidation of the 3-D structure of relatively small molecules (e.g., proteins of 100-150 amino acid residues), recent advances including isotopic labeling of the molecule of interest and transverse relaxation-optimized spectroscopy. (TROSY) have allowed the methodology to be extended to the analysis of much larger molecules, e.g., proteins with a molecular weight of 110 kDa (Wider, 2000).

NMR uses radio-frequency radiation to examine the environment of magnetic atomic nuclei in a homogeneous magnetic field pulsed with a specific radio frequency. The pulses perturb the nuclear magnetization of those atoms with nuclei of nonzero spin. Transient time domain signals are detected as the system returns to equilibrium. Fourier transformation of the transient signal into a frequency domain yields a one-dimensional NMR spectrum. Peaks in these spectra represent chemical shifts of the various active nuclei. The chemical shift of an atom is determined by its local electronic environment. Two-dimensional NMR experiments can provide information about the proximity of various atoms in the structure and in three dimensional space. Protein structures can be determined by performing a number of two- (and sometimes 3- or 4-) dimensional NMR experiments and using the resulting information as constraints in a series of protein folding simulations.

More information on NMR spectroscopy including detailed descriptions of how raw data obtained from an NMR experiment can be used to determine the 3-D structure of a macromolecule can be found in: Protein NMR Spectroscopy, Principles and Practice, (1996); Gronenborn et al. (1990); and Wider (2000), supra., the disclosures of all of which are incorporated herein by reference in their entirety Also of interest are peptidomimetic compounds that are designed based upon the amino acid sequences of compounds of the invention that are peptides. Peptidomimetic compounds are synthetic compounds having a three-dimensional conformation "motif" that is substantially the same as the three-dimensional conformation of a selected peptide. The peptide motif provides the peptidomimetic compound with the ability to inhibit the oligomerization of MUC1. Peptidomimetic compounds can have additional characteristics that enhance their in vivo utility, such as increased cell permeability and prolonged biological half-life. The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

Stapled/Stitched Peptides A particular modification is in the context of peptides as therapeutics is the so-called "Stapled Peptide" technology of Aileron Therapeutics. The general approach for "stapling" a peptide is that two key residues within the peptide are modified by attachment of linkers through the amino acid side chains. Once synthesized, the linkers are connected through a catalyst, thereby creating a bridge that physically constrains the peptide into its native α-helical shape. In addition to helping retain the native structure needed to interact with a target molecule, this conformation also provides stability against peptidases as well as promotes cell-permeating properties.

More particularly, the term "peptide stapling" may encompasses the joining of two double bond-containing sidechains, two triple bond-containing sidechains, or one double bond-containing and one triple bond-containing side chain, which may be present in a polypeptide chain, using any number of reaction conditions and/or catalysts to facilitate such a reaction, to provide a singly "stapled" polypeptide. In a specific embodiment, the introduction of a staple entails a modification of standard peptide synthesis, with α-methy, α-alkenyl amino acids being introduced at two positions along the peptide chain, separated by either three or six intervening residues (i+4 or i+7). These spacings place the stapling amino acids on the same fact of the α-helix, straddling either one (i+4) or two (i+7) helical turns. The fully elongated, resin-bound peptide can be exposed to a ruthenium catalyst that promotes cross-linking of the alkenyl chains through olefin metathesis, thereby forming an all-hydrocarbon macrocyclic cross-link. U.S. Pat. Nos. 7,192,713 and 7,183,059, and U.S. Patent Publications 2005/02506890 and 2006/0008848, describing this technology, are hereby incorporated by reference. See also Schafineister et al., *Journal of the American Chemical Society,* 122(24): p. 5891-5892 (2000); Walensky et al., *Science* 305:1466-1470 (2004). Additionally, the term "peptide stitching" refers to multiple and tandem "stapling" events in a single peptide chain to provide a "stitched" (multiply stapled) polypeptide, each of which is incorporated herein by reference. See WO 2008/121767 for a specific example of stitched peptide technology.

IV. Therapies

A. Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Inflammatory Disease States and Conditions i. Sepsis

Sepsis is a serious medical condition characterized by a whole-body inflammatory state caused by infection. Traditionally the term sepsis has been used interchangeably with septicaemia and septicemia ("blood poisoning"). However, these terms are no longer considered synonymous; septicemia is considered a subset of sepsis.

Symptoms of sepsis are often related to the underlying infectious process. When the infection crosses into sepsis, the resulting symptoms are that of systemic inflammatory response syndrome (SIRS): general inflammation, fever, elevated white blood cell count (leukocytosis), and raised heart rate (tachycardia) and breathing rate (tachypnea). Secondary to the above, symptoms also include flu like chills.

The immunological response that causes sepsis is a systemic inflammatory response causing widespread activation of inflammation and coagulation pathways. This may progress to dysfunction of the circulatory system and, even under optimal treatment, may result in the multiple organ dysfunction syndrome and eventually death.

Sepsis is considered present if infection is highly suspected or proven and two or more of the following systemic inflammatory response syndrome (SIRS) criteria are met:
  heart rate>90 beats per minute
  body temperature<36 (96.8° F.) or >38° C. (100.4° F.)
  hyperventilation (high respiratory rate)>20 breaths per minute or, on blood gas, a $P_aCO_2$ less than 32 mm Hg
  white blood cell count<4000 cells/mm$^3$ or >12000 cells/mm$^3$ (<4×10$^9$ or >12×10$^9$ cells/L), or greater than 10% band forms (immature white blood cells).

Consensus definitions however continue to evolve with the latest expanding the list of signs and symptoms of sepsis to reflect clinical bedside experience.

The more critical subsets of sepsis are severe sepsis (sepsis with acute organ dysfunction) and septic shock (sepsis with refractory arterial hypotension). Alternatively, when two or more of the systemic inflammatory response syndrome criteria are met without evidence of infection, patients may be diagnosed simply with "SIRS." Patients with SIRS and acute organ dysfunction may be termed "severe SIRS."

Patients are defined as having "severe sepsis" if they have sepsis plus signs of systemic hypoperfusion; either end organ dysfunction or a serum lactate greater than 4 mmol/dL. Patient are defined as having septic shock if they have sepsis plus hypotension after an appropriate fluid bolus (typically 20 ml/kg of crystaloid). The criteria for diagnosing an adult with sepsis do not apply to infants under one month of age. In infants, only the presence of infection plus a "constellation" of signs and symptoms consistent with the systemic response to infection are required for diagnosis.

The therapy of sepsis rests on antibiotics, surgical drainage of infected fluid collections, fluid replacement and appropriate support for organ dysfunction. This may include hemodialysis in kidney failure, mechanical ventilation in pulmonary dysfunction, transfusion of blood products, and drug and fluid therapy for circulatory failure. Ensuring adequate nutrition, if necessary by parenteral nutrition, is important during prolonged illness.

A problem in the adequate management of septic patients has been the delay in administering therapy after sepsis has been recognized. Published studies have demonstrated that for every hour delay in the administration of appropriate antibiotic therapy there is an associated 7% rise in mortality. A large international collaboration was established to educate people about sepsis and to improve patient outcomes with sepsis, entitled the "Surviving Sepsis Campaign." The Campaign has published an evidence-based review of management strategies for severe sepsis, with the aim to publish a complete set of guidelines in subsequent years.

Most therapies aimed at the inflammatory process itself have failed to improve outcome, however drotrecogin alfa (activated protein C, one of the coagulation factors) has been shown to decrease mortality from about 31% to about 25% in severe sepsis. To qualify for drotrecogin alfa, a patient must have severe sepsis or septic shock with an APACHE II score of 25 or greater and a low risk of bleeding. Low dose hydrocortisone treatment has shown promise for septic shock patients with relative adrenal insufficiency as defined by ACTH stimulation testing.

Standard treatment of infants with suspected sepsis consists of supportive care, maintaining fluid status with intravenous fluids, and the combination of a β-lactam antibiotic (such as ampicillin) with an aminoglycoside such as gentamicin.

ii. Trauma

Physical trauma is a serious and body-altering physical injury, such as the removal of a limb. Blunt force trauma, a type of physical trauma caused by impact or other force applied from or with a blunt object, whereas penetrating trauma is a type of physical trauma in which the skin or tissues are pierced by an object. Trauma can also be described as both unplanned, such as an accident, or planned, in the case of surgery. Both can be characterized by mild to severe tissue damage, blood loss and/or shock, and both may lead to subsequent infection, including sepsis. The present invention provides to treatment of trauma, including both pre-treatment (in the case of a medical procedure) and treatment after trauma injury as occurred.

Surgery. Surgery uses operative manual and instrumental techniques on a patient to investigate and/or treat a pathological condition such as disease or injury, to help improve bodily function or appearance, or sometimes for some other reason. The present invention can address trauma resulting from surgeries, as defined further below.

As a general rule, a procedure is considered surgical when it involves cutting of a patient's tissues or closure of a previously sustained wound. Other procedures that do not necessarily fall under this rubric, such as angioplasty or endoscopy, may be considered surgery if they involve common surgical procedure or settings, such as use of a sterile environment, anesthesia, antiseptic conditions, typical surgical instruments, and suturing or stapling. All forms of surgery are considered invasive procedures; so-called noninvasive surgery usually refers to an excision that does not penetrate the structure being addressed (e.g., laser ablation of the cornea) or to a radiosurgical procedure (e.g., irradiation of a tumor). Surgery can last from minutes to hours.

Surgical procedures are commonly categorized by urgency, type of procedure, body system involved, degree of invasiveness, and special instrumentation. Elective surgery is done to correct a non-life-threatening condition, and is carried out at the patient's request, subject to the surgeon's and the surgical facility's availability. Emergency surgery is surgery which must be done quickly to save life, limb, or functional capacity. Exploratory surgery is performed to aid or confirm a diagnosis. Therapeutic surgery treats a previously diagnosed condition.

Amputation involves cutting off a body part, usually a limb or digit. Replantation involves reattaching a severed body part. Reconstructive surgery involves reconstruction of an injured, mutilated, or deformed part of the body. Cosmetic surgery is done to improve the appearance of an otherwise normal structure. Excision is the cutting out of an organ, tissue, or other body part from the patient. Transplant surgery is the replacement of an organ or body part by insertion of another from different human (or animal) into the patient. Removing an organ or body part from a live human or animal for use in transplant is also a type of surgery.

When surgery is performed on one organ system or structure, it may be classed by the organ, organ system or tissue involved. Examples include cardiac surgery (performed on the heart), gastrointestinal surgery (performed within the digestive tract and its accessory organs), and orthopedic surgery (performed on bones and/or muscles).

Minimally invasive surgery involves smaller outer incision(s) to insert miniaturized instruments within a body cavity or structure, as in laparoscopic surgery or angioplasty. By contrast, an open surgical procedure requires a large incision to access the area of interest. Laser surgery involves use of a laser for cutting tissue instead of a scalpel or similar surgical instruments. Microsurgery involves the use of an operating microscope for the surgeon to see small structures. Robotic surgery makes use of a surgical robot, such as Da Vinci or Zeus surgical systems, to control the instrumentation under the direction of the surgeon.

Traumatic Hemorrhage. Traumatic hemorrhage accounts for much of the wide ranging international impact of injury, causing a large proportion of deaths and creating great morbidity in the injured. Despite differences in pre-hospital care, the acute management of traumatic hemorrhage is similar around the world and follows well accepted published guidelines. A critically injured patient's care occurs as four, often overlapping segments: the resuscitative, operative, and critical care phases. The diagnosis and control of bleeding should be a high priority during all of the phases of trauma care and is especially important in the patient who is in hemorrhagic shock. Early attempts at hemorrhage control include direct control of visible sources of severe bleeding with direct pressure, pressure dressings, or tourniquets; stabilization of long bone and pelvic fractures; and keeping the patient warm. During the resuscitative phase, warmed intravenous fluids, hypotensive resuscitation prior to surgical control of hemorrhage, and appropriate transfusion of blood and blood products are provided. In the operative phase, surgical control of the hemorrhage and any other injury, and additional transfusion is provide. Finally, the critical care phase provides for post-operative support and tissue perfusion.

iii. Acute Pancreatitis

Acute pancreatitis is rapidly-onset inflammation of the pancreas. Depending on its severity, it can have severe complications and high mortality despite treatment. While mild cases are often successfully treated with conservative measures or laparoscopy, severe cases require invasive surgery (often more than one intervention) to contain the disease process.

iv. Acute Respiratory Distress Syndrome

Acute respiratory distress syndrome (ARDS), also known as respiratory distress syndrome (RDS) or adult respiratory distress syndrome (in contrast with IRDS) is a serious reaction to various forms of injuries to the lung. This is the most important disorder resulting in increased permeability pulmonary edema.

ARDS is a severe lung disease caused by a variety of direct and indirect insults. It is characterized by inflammation of the lung parenchyma leading to impaired gas exchange with concomitant systemic release of inflammatory mediators causing inflammation, hypoxemia and frequently resulting in multiple organ failure. This condition is life threatening and often lethal, usually requiring mechanical ventilation and admission to an intensive care unit. A less severe form is called acute lung injury (ALI).

ARDS can occur within 24 to 48 hours of an injury or attack of acute illness. In such a case the patient usually presents with shortness of breath, tachypnea, and symptoms related to the underlying cause, i.e., shock. Long term illnesses can also trigger it, such as malaria. The ARDS may then occur sometime after the onset of a particularly acute case of the infection.

An arterial blood gas analysis and chest X-ray allow formal diagnosis by inference using the aforementioned criteria. Although severe hypoxemia is generally included, the appropriate threshold defining abnormal $PaO_2$ has never been systematically studied. Any cardiogenic cause of pulmonary edema should be excluded. This can be done by placing a pulmonary artery catheter for measuring the pulmonary artery wedge pressure. However, this is not necessary and is now rarely done as abundant evidence has emerged demonstrating that the use of pulmonary artery catheters does not lead to improved patient outcomes in critical illness including ARDS. Plain chest X-rays are sufficient to document bilateral alveolar infiltrates in the majority of cases. While CT scanning leads to more accurate images of the pulmonary parenchyma in ARDS, its has little utility in the clinical management of patients with ARDS, and remains largely a research tool.

Acute respiratory distress syndrome is usually treated with mechanical ventilation in the Intensive Care Unit. Ventilation is usually delivered through oro-tracheal intubation, or tracheostomy whenever prolonged ventilation (≥2 weeks) is deemed inevitable. The possibilities of non-invasive ventilation are limited to the very early period of the disease or, better, to prevention in individuals at risk for the development of the disease (atypical pneumonias, pulmonary contusion, major surgery patients). Treatment of the underlying cause is imperative, as it tends to maintain the ARDS picture. Appropriate antibiotic therapy must be administered as soon as microbiological culture results are available. Empirical therapy may be appropriate if local microbiological surveillance is efficient. More than 60% ARDS patients experience a (nosocomial) pulmonary infection either before or after the onset of lung injury. The origin of infection, when surgically treatable, must be operated on. When sepsis is diagnosed, appropriate local protocols should be enacted.

v. Ischemia-Reperfusion Injury

Reperfusion injury refers to damage to tissue caused when blood supply returns to the tissue after a period of ischemia. The absence of oxygen and nutrients from blood creates a condition in which the restoration of circulation results in inflammation and oxidative damage through the induction of oxidative stress rather than restoration of normal function.

The damage of reperfusion injury is due in part to the inflammatory response of damaged tissues. White blood cells carried to the area by the newly returning blood release a host of inflammatory factors such as interleukins as well as free radicals in response to tissue damage. The restored blood flow reintroduces oxygen within cells that damages cellular proteins, DNA, and the plasma membrane. Damage to the cell's membrane may in turn cause the release of more free radicals. Such reactive species may also act indirectly in redox signaling to turn on apoptosis. Leukocytes may also build up in small capillaries, obstructing them and leading to more ischemia.

Reperfusion injury plays a part in the brain's ischemic cascade, which is involved in stroke and brain trauma. Repeated bouts of ischemia and reperfusion injury also are thought to be a factor leading to the formation and failure to heal of chronic wounds such as pressure sores and diabetic foot ulcers. Continuous pressure limits blood supply and causes ischemia, and the inflammation occurs during reperfusion. As this process is repeated, it eventually damages tissue enough to cause a wound.

In prolonged ischemia (60 min or more), hypoxanthine is formed as breakdown product of ATP metabolism. The enzyme xanthine dehydrogenase is converted to xanthine oxidase as a result of the higher availability of oxygen. This oxidation results in molecular oxygen being converted into highly reactive superoxide and hydroxyl radicals. Xanthine oxidase also produces uric acid, which may act as both a prooxidant and as a scavenger of reactive species such as peroxinitrite. Excessive nitric oxide produced during reperfusion reacts with superoxide to produce the potent reactive species peroxynitrite. Such radicals and reactive oxygen species attack cell membrane lipids, proteins, and glycosaminoglycans, causing further damage. They may also initiate specific biological processes by redox signaling.

vi. Cardiovascular Disease

Cardiovascular disease refers to the class of diseases that involve the heart or blood vessels (arteries and veins). While the term technically refers to any disease that affects the cardiovascular system, it is usually used to refer to those related to atherosclerosis (arterial disease). These conditions have similar causes, mechanisms, and treatments. Treatment of cardiovascular disease depends on the specific form of the disease in each patient, but effective treatment always includes preventive lifestyle changes discussed above. Medications, such as blood pressure reducing medications, aspirin and the statin cholesterol-lowering drugs may be helpful. In some circumstances, surgery or angioplasty may be warranted to reopen, repair, or replace damaged blood vessels Most Western countries face high and increasing rates of cardiovascular disease. Each year, heart disease kills more Americans than cancer. Diseases of the heart alone caused 30% of all deaths, with other diseases of the cardiovascular system causing substantial further death and disability. Up until the year 2005, it was the number 1 cause of death and disability in the United States and most European countries. A large histological study (PDAY) showed vascular injury accumulates from adolescence, making primary prevention efforts necessary from childhood.

Some biomarkers are thought to offer a more detailed risk of cardiovascular disease. However, the clinical value of these biomarkers is questionable. Currently, biomarkers which may reflect a higher risk of cardiovascular disease include:

higher fibrinogen and PAI-1 blood concentrations
elevated homocysteine, or even upper half of normal
elevated blood levels of asymmetric dimethylarginine
high inflammation as measured by C-reactive protein
elevated blood levels of B-type natriuretic peptide (BNP)

Various forms of cardiovascular disease include aneurysms, angina, arrhythmia, atherosclerosis, cardiomyopathy, cerebrovascular disease, congenital heart disease, congestive heart failure, myocarditis, valve disease, coronary artery disease, dilated cardiomyopathy, diastolic dysfunction, endocarditis, high blood pressure (hypertension), hypertrophic cardiomyopathy, nitral valve prolapse, myocardial infarction, and venous thromboembolism.

vii. Autoimmune/Inflammatory Disease

The present invention contemplates the treatment of a variety of autoimmune and/or inflammatory disease states such as spondyloarthropathy, ankylosing spondylitis, psoriatic arthritis, reactive arthritis, enteropathic arthritis, ulcerative colitis, Crohn's disease, irritable bowel disease, inflammatory bowel disease, rheumatoid arthritis, juvenile rheumatoid arthritis, familial Mediterranean fever, amyotrophic lateral sclerosis, Sjogren's syndrome, early arthritis, viral arthritis, multiple sclerosis, or psoriasis. The diagnosis and treatment of these diseases are well documented in the literature.

viii. Chemotherapy, Radiotherapy and Cytokine Therapy Toxicity

Various forms of cancer therapy, including chemotherapy, radiation, and cytokines, are associated with toxicity, sometimes severe, in the cancer patient. To the extent that the toxicity is caused at least in part by the extracellular actions of histones, the present invention seeks to reduce this toxicity using the pharmaceutical compositions of the present invention, thereby reducing or alleviating discomfort on the part of the patient, as well as permitting higher doses of the therapy.

ix. Burns

In medicine, a burn may be an injury caused by heat, cold, electricity, chemicals, friction or radiation. First-degree burns are usually limited to redness (erythema), a white plaque, and minor pain at the site of injury. These burns usually extend only into the epidermis. Second-degree burns additionally fill with clear fluid, have superficial blistering of the skin, and can involve more or less pain depending on the level of nerve involvement. Second-degree burns involve the superficial (papillary) dermis and may also involve the deep (reticular) dermis layer. Third-degree burns additionally have charring of the skin, and produce hard, leather-like eschars. An eschar is a scab that has separated from the unaffected part of the body. Frequently, there is also purple fluid. These types of burns are often painless, because nerve endings have been destroyed in the burned areas. Serious burns, especially if they cover large areas of the body, can cause death; any hint of burn injury to the lungs (e.g., through smoke inhalation) is a medical emergency.

Burns that injure the tissues underlying the skin, such as the muscles or bones, are sometimes categorized as fourth-degree burns. These burns are broken down into three additional degrees: fourth-degree burns result in the skin being irretrievably lost, fifth-degree burns result in muscle being irretrievably lost, and sixth-degree burns result in bone being charred.

A newer classification of "Superficial Thickness," "Partial Thickness" (which is divided into superficial and deep categories) and "Full Thickness" relates more precisely to the epidermis, dermis and subcutaneous layers of skin and is used to guide treatment and predict outcome.

Chemical burns are usually caused by chemical compounds, such as sodium hydroxide (lye), silver nitrate, and more serious compounds (such as sulfuric acid). Most chemicals (but not all) that can cause moderate to severe chemical burns are strong acids or bases. Nitric acid, as an oxidizer, is possibly one of the worst burn-causing chemicals. Hydrofluoric acid can eat down to the bone and its burns are often not immediately evident. Most chemicals that can cause moderate to severe chemical burns are called caustic.

Electrical burns are generally symptoms of electric shock, being struck by lightning, being defibrillated or cardioverted without conductive gel, etc. The internal injuries sustained may be disproportionate to the size of the "burns" seen—as these are only the entry and exit wounds of the electrical current.

Burns are assessed in terms of total body surface area (TBSA), which is the percentage affected by partial thickness or full thickness burns (superficial thickness burns are not counted). The rule of nines is used as a quick and useful way to estimate the affected TBSA. The first step in managing a person with a burn is to stop the burning process. With dry powder burns, the powder should be brushed off first. With other burns, the affected area should be rinsed with a large amount of clean water to remove foreign bodies and help stop the burning process. Cold water should never be applied to any person with extensive burns, as it may severely compromise the burn victim's temperature status. At this stage of management, it is also critical to assess the airway status. If the patient was involved in a fire, then it must be assumed that he or she has sustained inhalation injury until proven otherwise, and treatment should be managed accordingly.

Once the burning process has been stopped, and airway status is ensured, the patient should be volume resuscitated according to the Parkland formula. This formula dictates that the amount of Lactated Ringer's solution to deliver in the first twenty four hours after time of injury is:

fluid=4 cc×% TBSA×weight in kg

% TBSA excludes any first degree burn

Half of this fluid should be given in the first eight hours post injury and the rest in the subsequent sixteen hours. The formula is a guide only and infusions must be tailored to urine output and central venous pressure. Inadequate fluid resuscitation causes renal failure and death. Severe edema in full thickness burns may be treated by escharotomy.

x. Cancer

Cancer results from the outgrowth of a clonal population of cells from tissue. The development of cancer, referred to as carcinogenesis, can be modeled and characterized in a number of ways. An association between the development of cancer and inflammation has long-been appreciated. The inflammatory response is involved in the host defense against microbial infection, and also drives tissue repair and regeneration. Considerable evidence points to a connection between inflammation and a risk of developing cancer, i.e., chronic inflammation can lead to dysplasia.

Studies have estimated that nearly 15% of worldwide cancer is associated with microbial infection. Organisms such as human papilloma virus (HPV), hepatitis B and C virus, HIV, and *Helicobacter pylori* all have been linked to cancer. In other cases, environmental conditions causing chronic irritation and subsequent inflammation can also predispose to cancer, including cigarette smoke, asbestos and silica.

In the case of some types of viral infection, virally-encoded genes can contribute to cellular transformation. An example is the HPV oncoproteins E6 and E7. However, other microbes associated with cancer do not operate in this fashion as they are not transforming. For example, certain strains of *H. pylori* contain factors that affect host cell signaling but do not contain oncogenes. Interestingly, it has been observed that *H. pylori* induces MUC1.

Other ways in which chronic inflammatory states can lead to genomic lesions and tumor initiation are chemical. For example, host cells fight microbial infection by the production of free radicals. In addition to their anti-microbial effects, these molecules lead to oxidative damage and nitration of DNA bases which increases the risk of DNA mutations even in host cells.

Yet another path to cellular dysregulation may result from the cell death that occurs in infection or other inflammatory insult. Lost cells must be repopulated by the expansion of other cells, sometimes undifferentiated precursor cells such as tissue stem cells. Not surprisingly, many inflammatory pathways function to mediate survival and proliferation. Thus, in attempting to mediating tissue repair, the inflammatory response may unwittingly provide excessive survival and proliferative signals to cells, thus leading to tumorigenesis.

Because of the link between cancer and inflammation, the ability of the peptides and peptide analogs of the present invention to reduce inflammatory signalling pathways can be exploited in a pre-cancer or cancer risk situation to prevent or delay the onset of dysplastic growth.

C. Treatment Methods

Peptides or analogs that inhibit MUC1 oligomer formation are generally useful as anti-inflammatories. They can be administered to mammalian subjects (e.g., human patients) alone or in conjunction with other drugs that modulate inflammation. The compounds can also be administered to subjects that are genetically and/or due to, for example, physiological and/or environmental factors, susceptible to inflammation, e.g., subjects with a family history of inflammatory disease, or subjects with chronic inflammation or subject to chronic stress.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more times). Encapsulation of the polypeptide in a suitable delivery vehicle (e.g., polymeric microparticles or implantable devices) may increase the efficiency of delivery, particularly for oral delivery.

D. Combination Therapies

It is common in many fields of medicine to treat a disease with multiple therapeutic modalities, often called "combination therapies." Inflammatory disease are no exception.

To treat inflammatory disorders using the methods and compositions of the present invention, one would generally contact a target cell or subject with a MUC1 antagonist and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the MUC1 antagonist and the other includes the other agent.

Alternatively, the MUC1 antagonist may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the MUC1 antagonist or the other therapy will be desired. Various combinations may be employed, where the MUC1 antagonist is "A," and the other therapy is "B," as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are contemplated.

Agents or factors suitable for use in a combined therapy against an inflammatory disorder include steroids, glucocorticoids, non-steriodal anti-inflammatory drugs (NSAIDS; including COX-1 and COX-2 inhibitors), aspirin, ibuprofen, and naproxen. Analgesics are commonly associated with anti-inflammatory drugs but which have no anti-inflammatory effects. An example is paracetamol, called acetaminophen in the U.S. and sold under the brand name of Tylenol. As opposed to NSAIDS, which reduce pain and inflammation by inhibiting COX enzymes, paracetamol has recently been shown to block the reuptake of endocannabinoids, which only reduces pain, likely explaining why it has minimal effect on inflammation.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It also should be pointed out that any of the foregoing therapies may prove useful by themselves in treating inflammation.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Cell culture. Human ZR-75-1 breast cancer and U-937 leukemia cells were grown in RPMI 1640 medium containing 10% heat-inactivated fetal bovine serum (FBS), 100 units/ml penicillin, 100 µg/ml streptomycin and 2 mM L-glutamine. Human HeLa cervical and MCF-7 breast carcinoma cells were grown in Dulbecco's modified Eagle's medium with 10% FBS, antibiotics and L-glutamine. Human MCF-10A breast epithelial cells were grown in mammary epithelial cell growth medium (MEGM; Lonza, Walkersville, Md.) and treated with 20 ng/ml TNFα (BD Biosciences, San Jose, Calif.). Transfection of the MCF-10A cells with siRNA pools (Dharmacon, Lafayette, Colo.) was performed in the presence of Lipofectamine 2000 (Invitrogen, Carlsbad, Calif.). Cells were treated with 5 µM MUC1/CQC and MUC1/AQA peptides synthesized by the MIT Biopolymer Laboratory (Cambridge, Mass.).

Immunoprecipitation and immunoblotting. Lysates from sub-confluent cells were prepared as described (Ren et al., 2004). Soluble proteins were precipitated with anti-NF-κB p65 (Santa Cruz Biotechnology, Santa Cruz, Calif.). The immunoprecipitates and cell lysates were subjected to immunoblotting with anti-p65, anti-p65 (180-306) (Millipore, Billerica, Mass.) anti-MUC1-C (Ab5; Lab Vision, Fremont, Calif.), anti-IκBα (Santa Cruz Biotechnology), anti-Bcl-xL (Santa Cruz Biotechnology) and anti-α-actin (Sigma, St. Louis, Mo.). Immune complexes were detected with horseradish peroxidase-conjugated secondary antibodies (GE Healthcare Biosciences, Piscataway, N.J.) and enhanced chemiluminescence (GE Healthcare).

In vitro binding assays. GST, GST-MUC1-CD, GST-MUC1-CD(1-45) and GST-MUC1-CD(46-72) were prepared as described (Ahmad et al., 2007) and incubated with p65 and certain p65 deletion mutants. Purified GST-MUC1-CD was cleaved with thrombin to remove the GST moiety. GST-IκBα (Millipore, Billerica, Mass.) was incubated with p65(186-306) for 2 h at 25° C. in the absence and presence of purified MUC1-CD. Adsorbates to glutathione-conjugated beads were analyzed by immunoblotting.

Immunofluorescence confocal microscopy. Cells were fixed and permeabilized as described (Raina et al., 2006). Incubation with anti-MUC1-C and anti-NF-κB p65 in blocking buffer was performed overnight at 4° C. The cells were blocked with 10% goat serum and stained with anti-MUC1-

C, followed by FITC-conjugated secondary anti-hamster antibody. The cells were then incubated with anti-NF-κB p65 followed by Texas Red-conjugated anti-mouse Ig conjugate (Jackson Immuno-Research Laboratories, West Grove, Pa.). Nuclei were stained with 2 μM TO-PRO-3. Images were captured with a Zeiss LSM510 confocal microscope at 1024× 1024 resolution.

ChIP assays. Soluble chromatin was prepared as described (Wei et al., 2006) and precipitated with anti-p65, anti-MUC1-C or a control non-immune IgG. For Re-ChIP assays, complexes from the primary ChIP were eluted with 10 mM DTT, diluted in Re-ChIP buffer and reimmunoprecipitated with anti-p65. For PCR, 2 μl from a 50 μl DNA extraction was used with 25-35 cycles of amplification.

Luciferase assays. Cells were transfected with NFκB-Luc (Ahmad et al., 2007) or pMUC1-Luc (Yin et al., 2003) and SV-40-*Renilla*-Luc (Promega, Madison, Wis.) in the presence of Lipofectamine. After 48 h, the cells were lysed in passive lysis buffer. Lysates were analyzed for firefly and *Renilla* luciferase activities using the dual luciferase assay kit (Promega).

Example 2

Results

MUC1-C associates with NF-κB p65. To determine whether MUC1 interacts with NF-κB, anti-NF-κB p65 precipitates from ZR-75-1 breast cancer cells were immunoblotted with an antibody against the MUC1-C subunit cytoplasmic domain. The results demonstrate that MUC1-C coprecipitates with NF-κB p65 (FIG. 1A). Similar findings were obtained with lysates from MCF-7 breast cancer cells, which also overexpress endogenous MUC1 (FIG. 1B). To determine whether the MUC1-N subunit is necessary for the association, studies were performed on U-937 cells that stably express exogenous MUC1-C and not MUC1-N (Agata et al., 2008). The coprecipitation of NF-κB p65 and MUC1-C in these cells demonstrated that MUC1-N is dispensable for the interaction (FIG. 1C). Incubation of ZR-75-1 cell lysates with GST or a GST fusion protein containing the 72 amino acid MUC1-CD further demonstrated that MUC1-CD associates with NF-κB p65 (FIG. 1D). These findings indicated that the MUC1-C subunit associates constitutively with NF-κB p65 in human breast cancer cells and that the interaction is mediated by the MUC1-C cytoplasmic domain.

MUC1-CD binds directly to NF-κB p65. To determine whether MUC1 binds directly to NF-κB, the inventors incubated GST, GST-MUC1-CD or GST-MUC1-CD deletion mutants (FIG. 7A, upper panel) with purified recombinant NF-κB p65. Analysis of the adsorbates demonstrated that GST-MUC1-CD, and not GST, binds to NF-κB p65 (FIG. 7A, lower panels). Incubation of MUC1-CD deletion mutants further demonstrated that this interaction is mediated by MUC1-CD(46-72), and not MUC1-CD(1-45) (FIG. 7A, lower panels). NF-κB p65 is a 551-amino acid protein that includes an N-terminal Rel homology domain (RHD) and a C-terminal transactivation domain (TAD) (FIG. 7B, upper panel). Incubation of GST-MUC1-CD with purified NF-κB deletion mutants demonstrated binding to p65(1-306) and not p65(354-551) (FIG. 7B, lower panels). To further define the NF-κB region responsible for the interaction, the inventors incubated GST-MUC1-CD with p65(1-180) and p65(186-306). The results show that MUC1-CD binds to p65(1-180) (FIG. 7C). As a control, there was no detectable interaction of GST-IκBα and p65(1-180) (FIG. 7C). In that regard, IκBα binds to sequences just upstream to the NLS at amino acids 301-304 (Jacobs et al., 1998; Huxford et al., 1998). Notably, however, both MUC1-CD and IκBα formed complexes with p65(186-306) (FIG. 7D). These findings indicated that, like IκBα, MUC1-CD binds directly to the NF-κB p65 RHD.

MUC1-CD competes with IκBα for binding to NF-κB p65. The conserved RHD is responsible for DNA binding, dimerization and association with the IκB inhibitory proteins (Ghosh et al., 1998; Chen and Greene, 2004). To determine whether binding of MUC1 to the RHD region affects the association with IκBα, the inventors first studied ZR-75-1 cells that are stably silenced for MUC1 with a MUC1 siRNA (FIG. 8). Silencing of MUC1 was associated with increased binding of NF-κB p65 and IκBα (FIG. 2A). In addition, stable expression of exogenous MUC1 in HeLa cells (Ahmad et al., 2007) decreased the interaction between NF-κB p65 and IκBα (FIG. 2B). Stable expression of MUC1-CD in 3Y1 cells (Huang et al., 2005) was also sufficient to block binding of NF-κB p65 and IκBα (FIG. 2C), confirming that the MUC1-C cytoplasmic domain, and not other regions of this subunit, is responsible for the interaction. To determine whether MUC1 directly affects binding of NF-κB p65 and IκBα, the inventors performed competition studies in which binding of IκBα to p65(186-306) was assessed in the presence of MUC1-CD. As expected, binding of IκBα to p65 (186-306) was detectable in the absence of MUC1-CD (FIG. 2D). Significantly, however, the addition of increasing amounts of MUC1-CD was associated with a progressive decrease in the interaction IκBα and p65(186-306) (FIG. 2D). These findings indicate that NF-κB p65 forms mutually exclusive complexes with IκBα and MUC1-CD.

MUC1-C associates with NF-κB p65 in the nucleus. Confocal analysis of ZR-75-1 cells showed nuclear colocalization of MUC1-C and NF-κB p65 (FIG. 3A). In addition, and consistent with MUC1-CD competing for binding to NF-κB p65, silencing MUC1 in the ZR-75-1 cells was associated with localization of nuclear NF-κB p65 to the cytoplasm (FIG. 3A). Previous studies demonstrated that MUC1 contributes to the upregulation of Bcl-xL expression (Ahmad et al., 2007). To determine if MUC1-C affects the NF-κB p65 transcription complex, the inventors performed ChIP assays with anti-p65. Immunoprecipitation of the NF-κB responsive element (RE) in the promoter of the Bcl-xL gene (GGGACT-GCCC; -366 to -356) (Grillot et al., 1997) was analyzed by semiquantitative PCR. In ZR-75-1 cells, occupancy of the Bcl-xL promoter by NF-κB p65 was decreased by silencing MUC1 (FIG. 3B). As a control, there was no detectable signal in immunoprecipitates performed with non-immune IgG (FIG. 3B). There was also no detectable NF-κB p65 occupancy of a control region (CR; -1001 to -760) of the Bcl-xL promoter upstream to the NF-κB-RE (FIG. 3B). Analysis of HeLa cells further demonstrated that expression of exogenous MUC1 is associated with increased NF-κB p65 occupancy of the Bcl-xL promoter (FIG. 3C). To determine whether MUC1-C is present in the NF-κB transcription complex, ChIP assays were performed with anti-MUC1-C. Using chromatin from ZR-75-1 cells, MUC1-C occupancy was detectable on the NF-κB-RE and not on the control region (FIG. 3D, left). In Re-ChIP assays, the anti-MUC1-C complexes were released, reimmunoprecipitated with anti-p65 and then analyzed by PCR. Anti-p65 precipitated the NF-κB-RE region after release from anti-MUC1-C (FIG. 3D, right), indicating that MUC1-C is constitutively present in the Bcl-xL promoter region occupied by the NF-κB transcription complex.

Inducible interaction of NF-κB p65 and MUC1-C in MCF-10A breast epithelial cells. The non-malignant MCF-10A breast epithelial cells (Soule et al., 1990; Muthuswamy et al., 2001) express endogenous MUC1, but at levels lower than that found in breast carcinoma cells (Ahmad et al., 2007). The inventors found, however, that stimulation of the MCF-10A cells with TNFα is associated with a substantial upregulation of MUC1 expression (FIG. 4A). In contrast to breast cancer cells, the MCF-10A cells exhibited little if any constitutive interaction between NF-κB p65 and MUC1-C (FIG. 4B). In turn, stimulation of the MCF-10A cells with TNFα induced the interaction between NF-κB p65 and MUC1-C (FIG. 4B). NF-κB engages consensus and degenerate κB binding sequences (5'-GGGRNWYYCC-3' (SEQ ID NO: 57), where R is a purine, N is any base, W is an adenine or thymine and Y is a pyrimidine). The MUC1 promoter contains such a potential sequence for NF-κB binding (5'-GGAAAGTCC-3'; SEQ ID NO: 63; −589 to −580) (Lagow et al., 2002) (FIG. 4C). ChIP analysis of TNFα-stimulated, but not unstimulated, MCF-10A cells demonstrated MUC1-C occupancy of the MUC1 promoter NF-κB binding motif (FIG. 4C). Re-ChIP analysis further demonstrated that NF-κB p65 and MUC1-C occupy the same region of the MUC1 promoter (FIG. 4D). These findings indicate, that, in contrast to breast cancer cells, the interaction between NF-κB p65 and MUC1-C and their occupancy of the NF-κB binding motif in the MUC1 promoter is inducible in MCF-10A cells.

Effects of MUC1 on NF-κB p65-mediated transcriptional activation. To determine whether MUC1 affects activation of NF-κB-mediated transcription, the inventors silenced NF-κB p65 in control and TNFα-stimulated MCF-10A cells (FIG. 5A). Silencing NF-κB p65 attenuated TNFα-induced increases in MUC1-C expression (FIG. 5A), consistent with a potential role for NF-κB p65 in activating MUC1 gene transcription. As expected, silencing NF-κB p65 attenuated TNFα-induced activation of the NF-κB-Luc reporter (FIG. 5B, left). Significantly, TNFα-induced activation of the MUC1 promoter-Luc (pMUC1-Luc) was also attenuated by silencing NF-κB p65 (FIG. 5B, right). To assess the effects of MUC1-C, the inventors silenced MUC1 expression in the MCF-10A cells with a MUC1siRNA (FIG. 5C). Consistent with the effects of MUC1 on NF-κB p65 occupancy of the NF-κB-RE, silencing MUC1 attenuated TNF□-induced activation of the NF-κB-Luc reporter (FIG. 5D, left). Moreover, silencing MUC1 attenuated activation of the pMUC1-Luc reporter (FIG. 5D, right). These findings indicate that MUC1 promotes NF-κB p65-mediated transcriptional activation of the MUC1 promoter.

Targeting MUC1-CD blocks NF-κB p65 function. To further define the role of MUC1 in NF-κB p65 function, the inventors synthesized a peptide corresponding to MUC1-CD (1-15) which blocks oligomerization and thereby function of the MUC1-C cytoplasmic domain (Leng et al., 2007). In addition, a control peptide was synthesized in which the CQC motif was mutated to AQA (FIG. 6A). A poly D-arginine transduction domain was included in the synthesis to facilitate entry of the peptides into cells (Fischer, 2007) (FIG. 6A). The MUC1/CQC peptide blocked the interaction between MUC1-CD and NF-κB p65 in vitro (FIG. 6A, left). By contrast, the MUC1/AQA peptide had little if any effect on this interaction (FIG. 6A, left). Treatment of MCF-10A cells with the MUC1/CQC, but not the MUC1/AQA, peptide also blocked the TNFα-induced interaction between MUC1-C and NF-κB p65 (FIG. 6A, right). ChIP analysis of the MUC1 promoter further showed that treatment with the MUC1/CQC peptide decreased TNFα-induced MUC1-C and NF-κB p65 occupancy of the NF-κB binding motif (FIG. 6B). In concert with these results, treatment with the MUC1/CQC peptide decreased TNFα-induced MUC1 expression (FIG. 6C). The MUC1/CQC peptide also attenuated TNFα-induced Bcl-xL expression (FIG. 6C). These findings indicate that disruption of MUC1-C function with the MUC1/CQC peptide attenuates (i) nuclear targeting of MUC1-C and (ii) NF-κB p65-mediated activation of MUC1 and Bcl-xL expression.

MUC1-C directly interacts with STAT3. The MUC1-C subunit interacts with certain transcription factors that include p53 (Wei, 2005; Wei, 2006; Wei, 2007). To determine whether MUC1-C associates with STAT3, anti-STAT3 precipitates from ZR-75-1 breast cancer cells were immunoblotted with an antibody against MUC1-C. The results demonstrate that MUC1-C constitutively associates with STAT3 (FIG. 9A, left). Similar results were obtained when coprecipitation studies were performed on MCF-7 breast cancer cells, which also express endogenous MUC1 (FIG. 9A, right). Incubation of ZR-75-1 cell lysates with GST or a GST-MUC1-CD fusion protein further demonstrated that MUC1-CD interacts with STAT3 (FIG. 9A). To determine whether the interaction is direct, studies were performed with purified recombinant STAT3. GST-MUC1-CD, and not GST, associated with STAT3 (FIG. 9C). Incubation with MUC1-CD deletion mutants further demonstrated that MUC1(46-72), and not MUC1-CD(1-45), binds directly to STAT3 (FIG. 9C). The structure of STAT3 includes a dimerization domain at the N-terminus, a central DNA binding domain (DBD) and C-terminal transactivation domain (Yu and Jove, 2004) (FIG. 9D). Incubation of MUC1-CD with STAT3 deletion mutants demonstrated binding to the DBD and not the dimerization or transactivation domains (FIG. 9D). These findings indicate that MUC1-C associates with STAT3 in breast cancer cells and that the interaction is mediated by direct binding of the MUC1-C cytoplasmic domain and the STAT3 DBD.

STAT3 and MUC1-C constitutively occupy the MUC1 promoter in breast cancer cells. MUC1-C localizes to the nucleus of breast cancer cells (Wei, 2006). To determine whether MUC1-C associates with STAT3 in the nucleus, the inventors performed chromatin immunoprecipitation (ChIP) assays on a consensus STAT binding site (SBS; −575 to −564; GGGCTATTCCGGGGAAGTGGTG (SEQ ID NO:58)) in the MUC1 promoter (Gaemers, 2001). Precipitation of chromatin from ZR-75-1 cells with anti-STAT3 demonstrated the presence of STAT3 on the STAT binding motif, and not on a control region (CR; +4524 to +4745) (FIG. 10A, left). ChIP analysis also demonstrated that MUC1-C constitutively occupies the STAT binding site (FIG. 10A, right). ChIP analysis of the MUC1 promoter in MCF-7 cells further demonstrated that both STAT3 and MUC1-C constitutively occupy the STAT binding site and not the control region (FIG. 10B). Moreover, Re-ChIP assays demonstrated that MUC1-C occupies the MUC1 promoter with STAT3 in both ZR-75-1 and MCF-7 cells (FIG. 10C). Analysis of MCF-7 cells that are stably silenced for MUC1 with a MUC1 siRNA further indicated that MUC1-C promotes STAT3 occupancy of the MUC1 promoter SBS (FIG. 10D). These findings indicate that MUC1-C associates with the STAT3 transcription complex.

IL-6 induces MUC1 expression in MCF-10A breast epithelial cells. The non-malignant MCF-10A breast epithelial cells express endogenous MUC1, but at levels lower than that in ZR-75-1 and MCF-7 breast cancer cells (Ahmad, 2007). However, stimulation of MCF-10A cells with IL-6, an activator of the STAT3 pathway (Yu and Jove, 2004), was associated with upregulation of MUC1-C expression (FIG. 11A, left) and targeting of MUC1-C to the nucleus (FIG. 11B, right). In contrast to the breast cancer cells, there was little constitutive association of MUC1-C with STAT3 in the MCF-10A cells (FIG. 11B). Moreover, stimulation with IL-6 induced binding of MUC1-C and STAT3 (FIG. 11B). ChIP analysis of the MUC1 promoter further showed that IL-6 induces both STAT3 and MUC1-C occupancy of the STAT binding site (FIG. 11C). In addition, re-ChIP studies demonstrated that MUC1-C associates with STAT3 on the MUC1 promoter by an IL-6-dependent mechanism (FIG. 11D). These findings indicate that the interaction between MUC1-C and STAT3, and their occupancy on the MUC1 promoter is inducible by IL-6 in MCF-10A cells.

IL-6 activates the MUC1 promoter by a STAT3-dependent mechanism. To confirm that STAT3 is responsible for the IL-6-induced upregulation of MUC1, the inventors silenced STAT3 in the MCF-10A cells (FIG. 12A). The results demonstrate that IL-6 induces MUC1 expression by an IL-6-dependent mechanism (FIG. 12A). IL-6 stimulation of MCF-10A cells is associated with upregulation of MUC1 mRNA levels as determined by RT-PCR (FIG. 12B). To determine whether IL-6 activates the MUC1 promoter, the MCF-10A cells were transfected to express a MUC1 promoter-luciferase construct (pMUC1-Luc). IL-6 stimulation was associated with activation of pMUC1-Luc expression (FIG. 12C). By contrast, mutation of the STAT binding site in pMUC1-Luc attenuated IL-6-induced activation of the reporter, consistent with activation by STAT3 (FIG. 12C). Moreover, silencing STAT3 blocked activation of pMUC1-Luc in the response to IL-6 (FIG. 12D). These findings demonstrate that activation of the MUC1 promoter by IL-6 is dependent on STAT3.

MUC1-C promotes targeting of STAT3 to the MUC1 promoter. To assess the effects of MUC1-C in the STAT3 transcription complex, the inventors silenced MUC1 in the MCF-10A cells (FIG. 13A, left) and then performed ChIP assays of the MUC1 promoter. The results demonstrate that IL-6-induced targeting of STAT3 to the MUC1 promoter is attenuated by silencing MUC1 (FIG. 13A, right). In concert with these results, silencing MUC1 also attenuated IL-6-induced activation of the pMUC1-Luc reporter (FIG. 13B). In ZR-75-1 cells, silencing MUC1 (FIG. 13C, left) was associated with decreases in STAT3 occupancy of the MUC1 promoter (FIG. 13C, right). Moreover, silencing MUC1 in ZR-75-1 cells decreased constitutive activation of the pMUC1-Luc reporter (FIG. 13D). These findings indicate that MUC1 contributes to targeting of STAT3 to the MUC1 promoter and thereby STAT3-mediated activation.

Inhibition of MUC1-C function blocks IL-6-induced targeting of STAT3 to the MUC1 promoter in MCF-10A cells. To further assess the role of MUC1-C in the regulation of STAT3, the inventors synthesized GO-201, a peptide inhibitor of MUC1-C oligomerization and function of the cytoplasmic domain (Raina, 2009). A control CP-1 peptide was also synthesized that had no effect on MUC1-C function (Raina, 2009). GO-201, and not CP-1, blocked the interaction between MUC1-CD and STAT3 in vitro (FIG. 14A). Treatment of MCF-10A cells with GO-201, and not CP-1, also blocked the IL-6-induced interaction between MUC1-C and STAT3 (FIG. 14B). Moreover, GO-201 inhibited IL-6-induced targeting of STAT3 and MUC1-C to the MUC1 promoter (FIG. 14C). Consistent with these results, GO-201 attenuated IL-6-induced activation of the pMUC1-Luc reporter (FIG. 14C). These findings demonstrate that inhibition of MUC1-C function blocks STAT3-mediated activation of MUC1 transcription.

MUC1-C-terminal CQC Stapled Peptides. The intracellular protein-protein interactions that govern many biological pathways are frequently mediated by α-helix structures of proteins. Helical peptides can also interfere with or stabilize protein-protein interactions. Native helical peptides have major shortcomings as therapeutic agents because of low potency, instability and inefficient delivery to cells. Recent studies have shown that these problems could be overcome by a chemical modification of α-helical peptides termed as hydrocarbon stapling.

The inventors used MUC1-C terminal endogenous peptide sequence (AIVYLIALAVCQCRRKNYG; SEQ ID NO: 64) and generated two α-helical peptides, GO-200-1B and GO-200-2B using hydrocarbon stapling:

```
                                           (SEQ ID NO: 65)
GO-200-1B:Ac-AIVYL-S5-ALA-S5-CQCRRKNYG-NH2

(SEQ ID NO: 66)
GO-200-2B:Ac-AKKYL-S5-ALA-B5-CQC-S5-RKNY-NH2
```

Figure 16A:
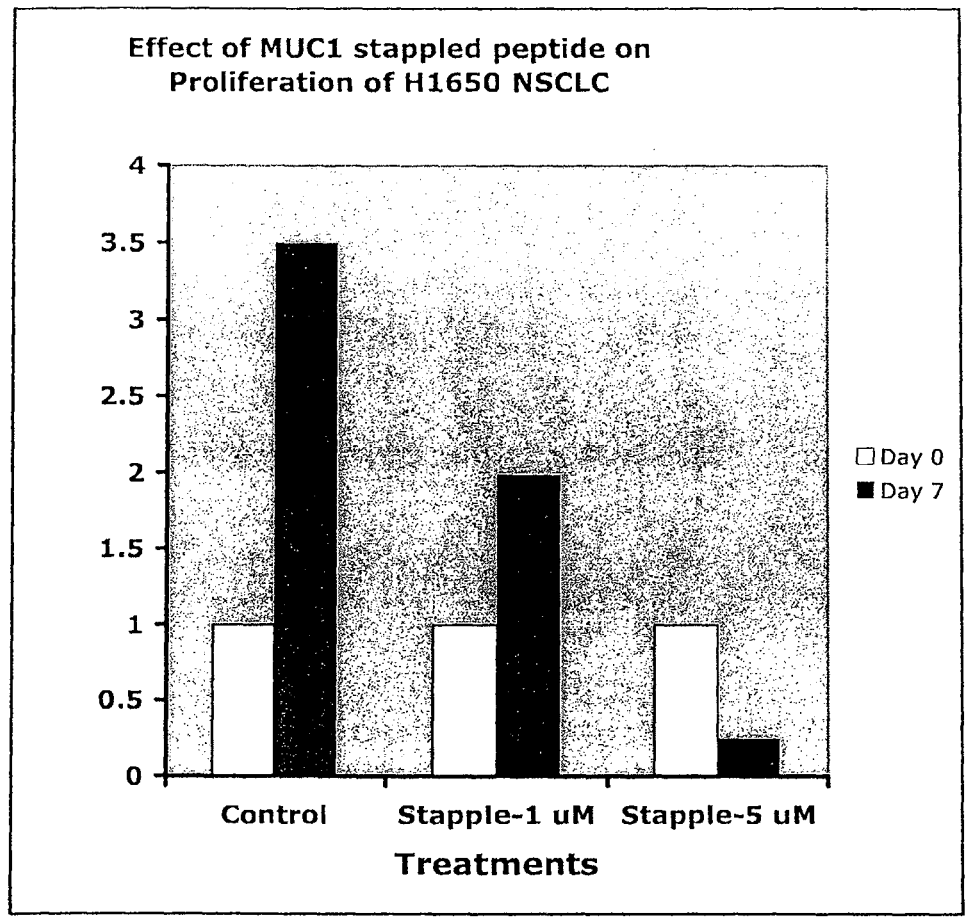
FIG. 16A: Effects of MUC1-CD-stapled peptide on the growth of H1650 non-small cell lung carcinoma cells. To assess sensitivity to inhibition of MUC1 function, H1650 NSCLC cells were treated with 1 and 5 μM MUC1 CQC stapled peptide (GO-200-1B) for 7 days. Treatment of H1650 cells with 5 μM GO-200-1B was associated with significant inhibition of growth and then a decrease in cell number.
Figure 16B:
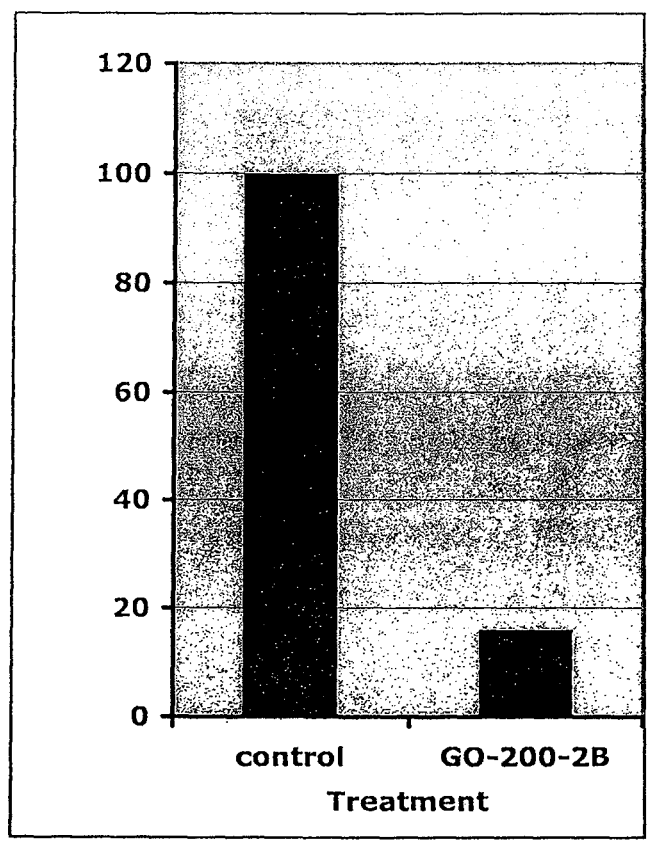
FIG. 16B: Effect of GO-200-2B on cell proliferation. H-1975 non-small cell lung carcinoma cell line was grown in DMEM with 10% heat-inactivated fetal bovine serum with 100 units/mL penicillin, 100 μg/ml streptomycin and 2 mmol/L L-glutamine. Cells were re-seeded one day before treatments. Cells were treated with 5 μM GO-200-2B for 3 days and cell viability was determined by trypan blue exclusion.
Figure 17:
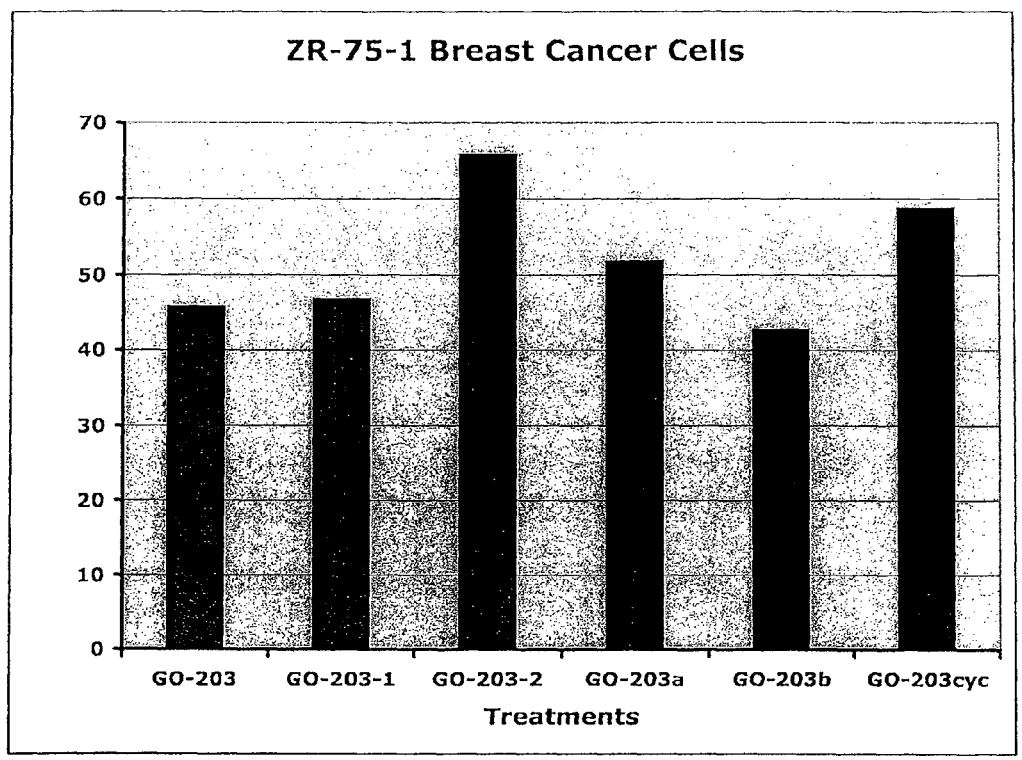
FIG. 17: Effect of different MUC1-CD CQC-region peptides on the growth of hormone-dependent breast carcinoma cells. To determine whether exposure to different MUC1-CD CQC-region containing peptides affect growth, ZR-75-1 breast carcinoma cells were treated with 5 μM of different peptides for 4 days and monitored for cell proliferation. Significantly, there was a substantial growth inhibition compared with that in cells left untreated.
Figure 18:
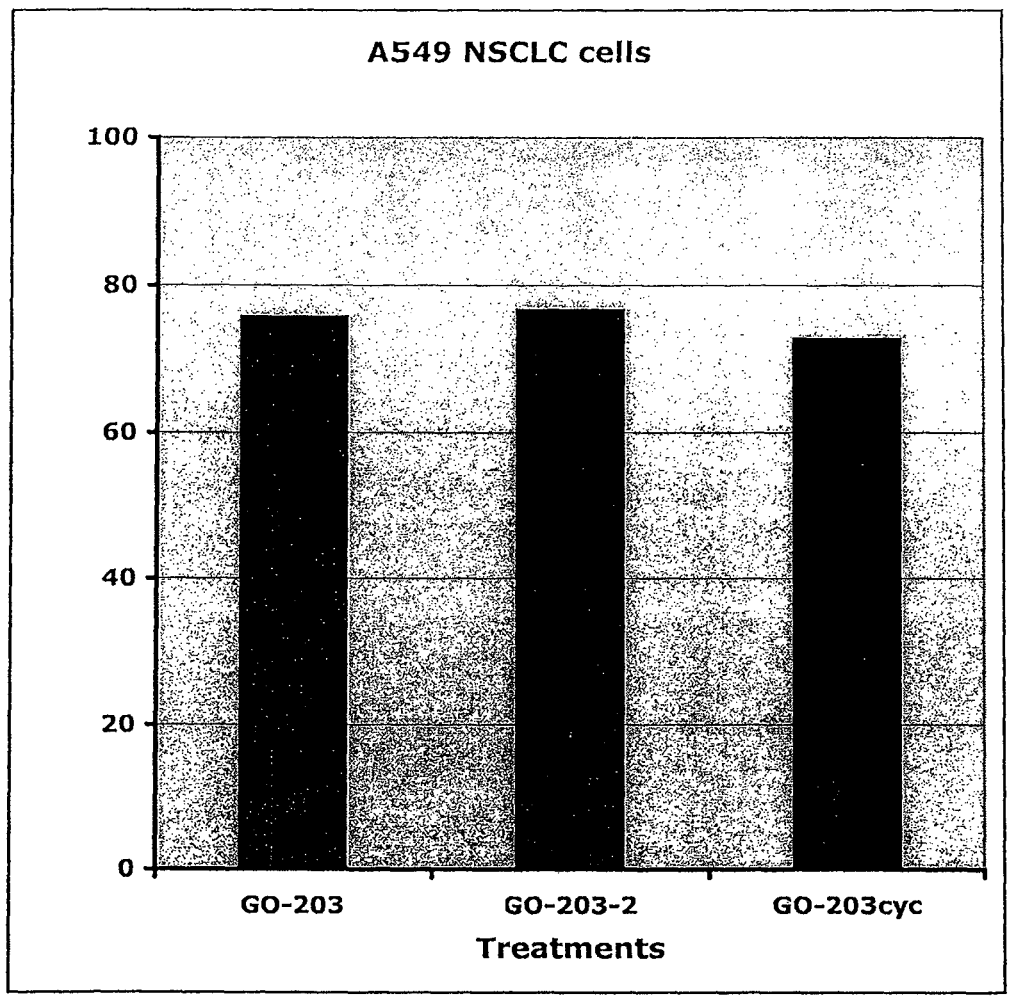
FIG. 18: Effect of different MUC1-CD CQC-region peptides on the growth of non small cell carcinoma cells. A549 non-small cell lung carcinoma cells were treated with 5 μM GO-203, GO-203-2 or GO-203cyc for 7 days. Viable cell number on day 7 was determined by trypan blue exclusion and percent growth inhibition was calculated by comparing the cell growth of untreated cells.
Figure 19:
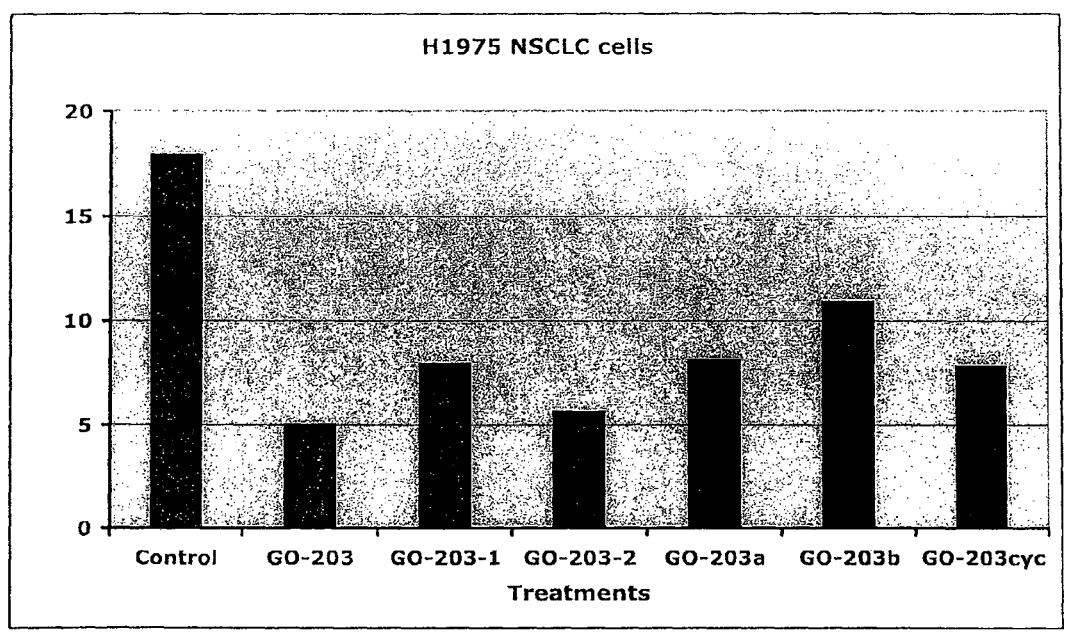
FIG. 19: Effect of different MUC1-CD CQC-region peptides on the growth of H1975 non-small cell carcinoma cells. H1975 non-small cell lung carcinoma cells were treated with 5 µM of different MUC1-CD CQC-region peptides for 6 days. Viable cell number on day 6 was determined by trypan blue exclusion. The results demonstrate that treatment of H1975 cells with 5 µM of different peptides was associated with significant inhibition of growth.
Figure 20:
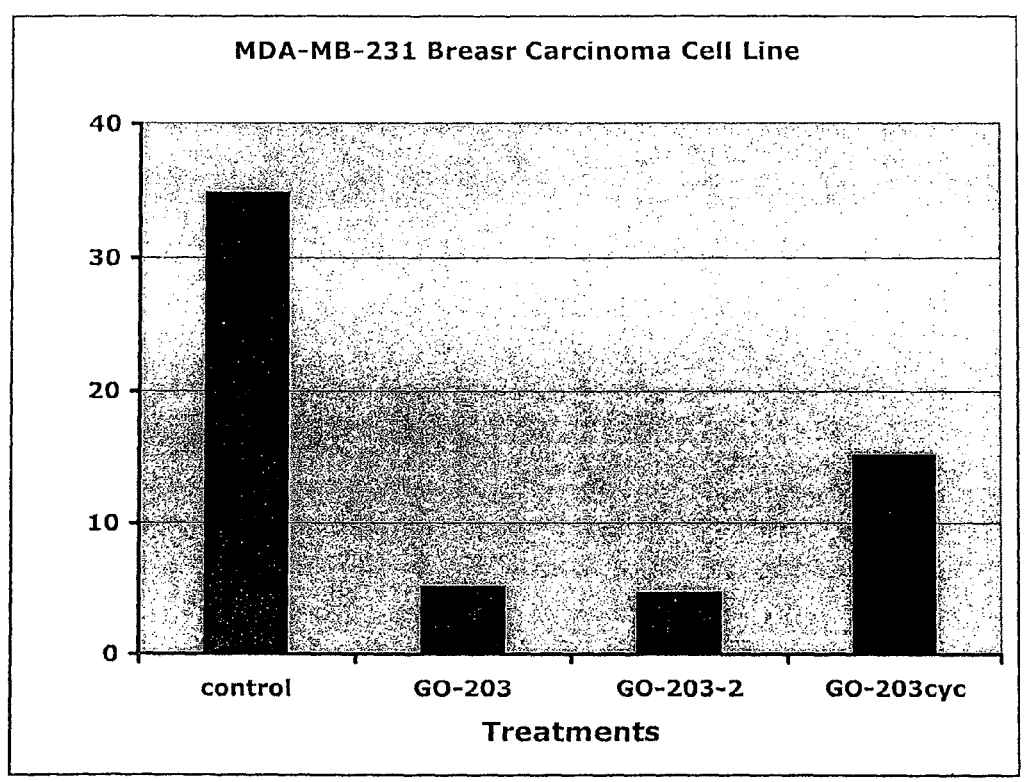
FIG. 20: Effect of different MUC1-CD CQC-region peptides on the growth of triple-negative breast carcinoma cells. MDA-MB-231 triple-negative breast carcinoma cells were treated with 5 µM of different MUC1-CD CQC-region peptides for 6 days. Viable cell number on day 6 was determined by trypan blue exclusion. The results demonstrate that treatment of MDA-MB-231 cells with different peptides was associated with significant inhibition of growth.
Figure 21:
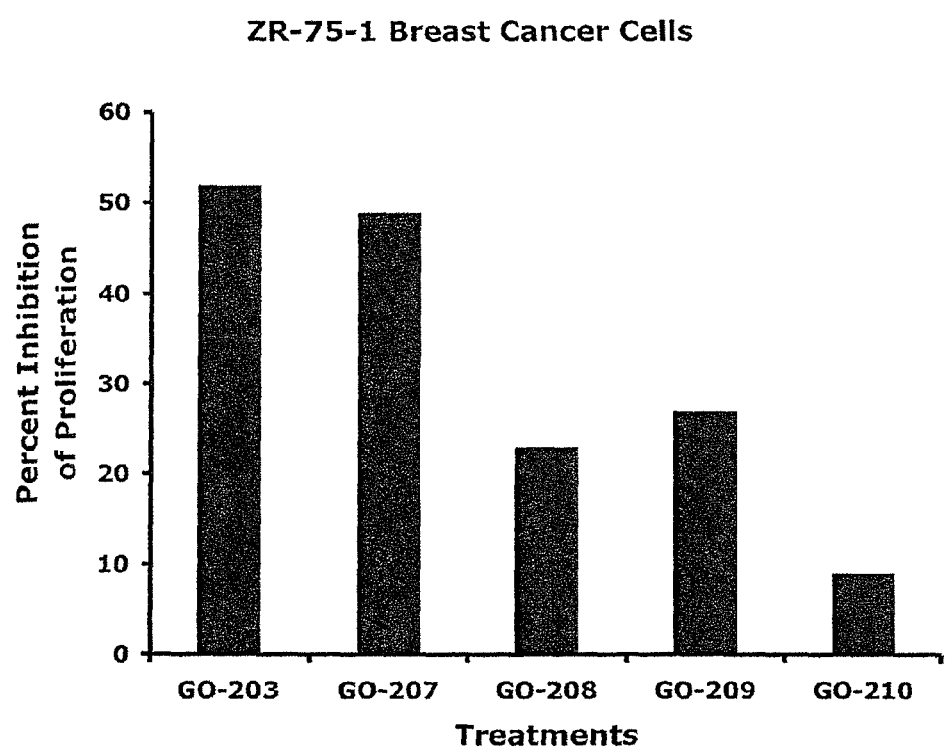
FIG. 21: Effect of Shorter GO-203 peptides on proliferation of ZR-75-1 Breast Cancer Cells. Human ZR-75-1 breast cancer cells were grown in RPMI1640 supplemented with 10% heat-inactivated fetal bovine serum, 100 units/ml penicillin, 100 µg/ml streptomycin. Cells were treated with different peptides at 5 µM every day for four days and cell viability was determined by trypan blue exclusion. In contrast to GO-210, treatment of ZR-75-1 breast carcinoma cells with 5 µM GO-203 (SEQ ID NO:53), GO-207 (SEQ ID NO:4), GO-208 (SEQ ID NO:50) and GO-209 (SEQ ID NO:54) every day for 4 days was associated with significant inhibition of growth.

To determine whether exposure to GO-200-1B affects growth of non-small cell lung carcinoma cells, H-1650 cells were treated with 1 and 5 μM GO-200-1B for 7 days and monitored for growth. The results demonstrate that treatment of cells with 5 μM GO-200-1B was associated with significant inhibition of growth (FIG. 16A). Moreover, another non-small cell lung carcinoma cell line, H-1975, was treated with 5 μM GO-200-2B for 3 days and monitored for cell growth as well as cell death. The results demonstrate that treatment of H-1975 cells with GO-200-2B for 3 days was associated with more than 80% inhibition of cell proliferation. Moreover, GO-200-2B was also associated with significant induction of cell death (FIG. 16B). These findings indicate that stapled MUC1-C peptides are effective in inducing growth arrest and death of human MUC1-positive cancer cells.

GO-203 analogs. The inventors' recent studies have shown that a MUC1 C-terminal peptide (CQCRRKNYGQLDIFP; SEQ ID NO: 3) is active in inhibiting growth of multiple carcinoma cell lines. They have also demonstrated that a shorter MUC 1-C-terminal peptide, CQCRRKN (SEQ ID NO: 4), is also active in killing tumor cells. However, these MUC1-C-terminal peptides consists of L-amino acids. Importantly, peptides with L-amino acids have susceptible to degradation by proteolytic enzymes, whereas those containing D-amino acids have been shown to be more stable. Consequently, they have generated an all-dextro form of the above described shorter MUC1 C-terminal peptide, in which the L-amino acids were changed to D-amino acids (GO-203). Moreover, to determine the minimum amino acid residues from the MUC1-C-terminal region that are required to retain the cell killing activity, they have also generated many different versions of GO-203 as described in FIG. 15.

Multiple tumor cell lines (ZR-75-1 Hormone-dependent Breast Carcinoma; MDA-MB-231 Triple-Negative Breast Carcinoma; A549 Non-small Cell Lung Carcinoma; H-1975 Non-small Cell Lung Carcinoma) were grown in RPMI-1640 supplemented with 10% heat-inactivated fetal bovine serum, 100 units/mL penicillin and 100 μg/mL streptomycin and 2 mmol/L L-glutamine. Cells were treated separately with 5 μM of different analogs of GO-203 (FIG. 15) for 3 to 7 days and viability was determined by trypan blue exclusion. The proliferation of different cell lines was compared with cells treated with vehicle only. The results demonstrate that treatment of multiple tumor cell lines with 5 μM of different analogs of GO-203 was associated with significant inhibition of growth (FIGS. 17-21).

Example 3

Discussion

Previous Studies. Overexpression of MUC1 is sufficient for the induction of anchorage-independent growth and tumorigenicity (Li et al., 2003a; Huang et al., 2003; Huang et al., 2005). Notably, however, the MUC1 transforming function is abrogated by mutation of the CQC motif in the cytoplasmic domain to AQA (Leng et al., 2007). MUC1 forms oligomers and the CQC motif is necessary for this oligomerization (Leng et al., 2007). Moreover, oligomer formation is necessary for targeting of the MUC1-C subunit to the nucleus (Leng et al., 2007). The inventors synthesized a MUC1-derived peptide that contains the CQC motif and a poly-Arg cell delivery domain for entry into cells. Initial studies with this MUC1/CQC peptide showed that it inhibits oligomerization of MUC1-CD in vitro, whereas MUC1/AQA did not. Significantly and consistent with nuclear targeting of MUC1 being dependent on oligomerization (Leng et al., 2007), uptake of the MUC1/CQC peptide was associated with down-regulation of MUC1-C levels in the nucleus. Moreover and notably, exposure of cells to MUC1/CQC, and not MUC1/AQA, was associated with growth arrest and the induction of necrosis. Other findings indicate that sensitivity to the MUC1/CQC peptide is dependent on overexpression of MUC1 and a function of MUC1 associated with the malignant phenotype. The MUC1/CQC peptide thus appears to have a dominant-negative activity that is selective for carcinoma cells overexpressing MUC1. Finally, the inventors found that administration of the MUC1/CQC peptide to tumor bearing mice at 10 and 30 mg/kg/d for 21 d was well-tolerated without apparent acute toxicities, and that treatment at these doses was effective in abrogating tumor growth. Administration of the MUC1/CQC peptide at 50 mg/kg/d for 7 d also demonstrated that tumor growth remains arrested for extended periods following treatment.

MUC1 binds to NF-κB p65 and blocks the IκBα interaction. The NF-κB proteins contain the conserved 300 amino acid RHD that confers DNA binding, dimerization and binding to IκB proteins (Hayden & Ghosh, 2008). The present work demonstrates that the MUC1-C subunit associates with NF-κB p65 in cells and that the MUC1-C cytoplasmic domain binds directly to p65. More detailed binding studies showed that MUC1-CD forms complexes with p65(1-306), but not p65(354-551), indicating that MUC1-CD interacts with the RHD. This observation was confirmed with binding of MUC1-CD to p65(1-180) and p65(186-306). Structural analysis of NF-κB and IκBα cocrystals has demonstrated that IκBα ankyrin repeats interact with amino acid residues just preceding the NLS that resides at the C-terminus of the NF-κB p65 RHD (Jacobs et al., 1998; Huxford et al., 1998). Binding of IκBα to this region of the NF-κB p65 RHD sterically masks the NLS (amino acids 287-300) and thereby targeting of NF-κB p65 to the nucleus. The finding that, like IκBα, MUC1-CD binds to p65(186-306) invoked the possibility that the MUC1-C subunit may interfere with the interaction between IκBα and NF-κB p65. Indeed, studies in cells with gain and loss of MUC1 expression indicated that MUC1 competes with IκBα for binding to NF-κB p65 and that MUC1-CD is sufficient for such competition. In concert with these results, silencing endogenous MUC1 in ZR-75-1 cells is associated with targeting of nuclear NF-κB p65 to the cytoplasm. Moreover, direct binding studies with purified proteins confirmed that MUC1-CD blocks the interaction between NF-κB p65 and IκBα. NF-κB p65 interacts with multiple proteins that affect DNA binding and transcription (Natoli et al., 2005). However, to the inventors' knowledge, there are no reports of proteins that interact with the NF-κB p65 RHD and interfere with binding of IκBα. Thus, based on these findings, the overexpression of MUC1-C in human malignancies could subvert the cytoplasmic retention of NF-κB p65 by competitively blocking the NF-κB p65-IκBα interaction.

MUC1 increases occupancy of NF-κB p65 on NF-κB target genes. Nuclear NF-κB activates IκBα expression in a negative feed back loop that promotes the formation of new NF-κB-IκBα complexes and shuttling of NF-κB back to the cytoplasm (Hayden & Ghosh, 2008). In this context, the association of MUC1-C with NF-κB p65 could attenuate downregulation of NF-κB signaling by blocking the interaction with IκBα. The present results provide support for a model in which binding of MUC1-C to NF-κB p65 results in targeting of NF-κB p65 to the promoters of NF-κB target genes (FIG. 6D). Stimulation of MCF-10A epithelial cells with TNFα was associated with binding of MUC1-C to NF-κB p65 and occupancy of these complexes on the NF-κB-RE in the Bcl-xL gene promoter. In ZR-75-1 cells, NF-κB p65 occupancy of the Bcl-xL NF-κ-RE was detectable constitutively and decreased by silencing MUC1. In concert with the findings obtained for the Bcl-xL NF-κB-RE, occupancy of the MUC1 NF-κB binding motif by NF-κB p65 and MUC1-C was constitutively detectable in ZR-75-1 breast cancer cells and inducible in MCF-10A epithelial cells. These findings and the demonstration that, like NF-κB p65, silencing of MUC1 attenuates activation of the NF-κB-Luc and pMUC1-Luc reporters indicate that MUC1-C is of importance to activation of the NF-κB p65 transcriptional function. Previous work has shown that downregulation of NF-κB signaling is delayed in the absence of IκBα (Gerondakis et al., 2006; Pasparakis et al., 2006) and, thus, overexpression of MUC1 in human tumors could confer similar effects by inhibiting the NF-κB p65-IκBα interaction.

Disruption of the NF-κB p65-MUC1-C interaction with the MUC1 inhibitor. The MUC1-C subunit forms oligomers by a mechanism dependent on a CQC motif in the cytoplasmic domain (Leng et al., 2007). MUC1-C oligomerization is necessary for its interaction with importin β and targeting to the nucleus (Leng et al., 2007). As mentioned above, a 15-mer peptide corresponding to the MUC1 cytoplasmic domain that includes the CQC motif blocks oligomerization of MUC1-CD in vitro and of MUC1-C in cells. The present results show that the same MUC1/CQC peptide blocks the direct binding of MUC1-CD and NF-κB p65 in vitro, indicating that MUC1-CD oligomerization is, at least in part, necessary for the interaction. The TNFα-induced association of NF-κB p65 and MUC1-C in MCF-10A cells was also blocked by treatment with the MUC1/CQC peptide. The specificity of the MUC1/CQC peptide is further supported by the lack of an effect of the mutated MUC1/AQA peptide on the interaction between MUC1-CD and NF-κB p65 in vitro and in cells. Blocking the NF-κB p65-MUC1-C interaction with the MUC1/CQC peptide was associated with a decrease in occupancy of NF-κB p65 on the NF-κB binding motif in the MUC1 promoter and a decrease in MUC1 expression. The MUC1/CQC peptide also decreased Bcl-xL expression. These findings thus provide support for the potential importance of the NF-κB p65-MUC1-C interaction in targeting of NF-κB p65 to the promoters of NF-κB target genes.

Does the MUC1-C-NF-κB p65 interaction contribute to a physiologic defense mechanism exploited by human tumors? TNFα stimulation of TNF receptor 1 induces the formation of cell membrane complexes that lead to the activation of (i) NF-κB and survival or, alternatively, (ii) caspase-8 and apoptosis (Micheau & Tschopp, 2003; Schneider-Brachert et al., 2004). The overexpression of MUC1, as found in human breast carcinomas (Kufe et al., 1984), blocks activation of caspase-8 and apoptosis in the response to TNFα and other death receptor ligands (Agata et al., 2008). In MCF-10A cells, MUC1-C interacts with caspase-8 and FADD as an induced response to death receptor stimulation and blocks recruitment of caspase-8 to the death receptor complex (Agata et al., 2008). Other work has demonstrated that MUC1-C associates with and activates the IKK complex (Ahmad et al., 2007) (FIG. 6D). As shown in the present work, TNFα-induced upregulation of MUC1-C expression in MCF-10A cells directly contributes to the activation of NF-κB p65. Thus, MUC1-C can activate the NF-κB pathway through interactions with both IKKs and p65, and thereby promote a survival response (FIG. 6D). In addition, the upregulation of MUC1-C protects against the induction of apoptosis by blocking caspase-8 activation. The present findings also indicate that through binding to NF-κB p65, MUC1-C can contribute to activation of the MUC1 gene in an auto-inductive loop and, as a result, prolong survival, albeit in a reversible manner. In this regard, MUC1 may play a physiologic role in transiently dictating cell fate in the inducible response to death receptor stimulation. Conversely, irreversible activation of MUC1 expression in carcinoma cells through a MUC1-C-NF-κB p65 regulatory loop could confer a phenotype that is stably resistant to cell death through persistent activation of NF-κB p65 and inhibition of caspase-8. Irreversible activation of a MUC1-C-NF-κB p65 loop and the upregulation of prosurvival NF-κB target genes could also contribute to the MUC1-induced block in the apoptotic response of human carcinoma cells to genotoxic, oxidative and hypoxic stress (Ren et al., 2004; Yin et al., 2003; Raina et al., 2004; Yin et al., 2004; 2007). Thus, a physiologic mechanism designed to protect epithelial cells during death receptor stimulation may have been exploited by human carcinomas for survival under adverse conditions.

MUC1-C interacts directly with STAT3. Constitutive activation of STAT3 has been identified in a wide variety of human carcinomas, including breast cancer, and certain hematologic malignancies (Aaronson, 2002; Bowman, 2000; Yu, 2004). The finding that MUC1 is constitutively overexpressed in breast and other carcinomas invoked the possibility for interaction between the MUC1 and STAT3 pathways. The present results demonstrate that the MUC1-C subunit associates with STAT3 in ZR-75-1 and MCF-7 breast cancer cells. Moreover, the interaction between MUC1-C and STAT3 is induced in the response of non-malignant MCF-10A breast epithelial cells to IL-6 stimulation. The results also demonstrate that the MUC1-C cytoplasmic domain binds directly to the STAT3 DBD. Few insights are available regarding other proteins that interact with the STAT3 DBD (Shuai, 2000). The C-terminal region of c-Jun binds to the STAT3 coiled-coil domain and the DBD, and thereby contributes to cooperation between STAT3 and c-Jun in driving transcription (Zhang, 1999). Other studies have demonstrated that the STAT3 DBD is essential for mediating interactions with NF-κB p65 (Yu, 2004). In addition, STAT3-mediated acetylation of NF-κB p65, and thereby maintenance of NF-κB activity, requires the STAT3 DBD (Lee, 2009). Thus, binding of MUC1-C to the STAT3 DBD could affect STAT3 interactions with c-Jun or NF-κB p65 and the regulation of gene transcription. In this context, ChIP analysis demonstrated that MUC1-C associates with STAT3 in soluble chromatin and is detectable with STAT3 on the STAT binding site in the MUC1 promoter. This occupancy of the MUC1 promoter STAT binding site by MUC1-C and STAT3 was found to be constitutive in breast cancer cells and inducible by IL-6 in the MCF-10A breast epithelial cells. STAT3 had been previously shown to interact with the MUC1 promoter and activate MUC1 gene transcription (Gaemers, 2001). However, to the inventors' knowledge, there have been no reports that MUC1-C constitutes part of the STAT3 transcription complex.

MUC1-C promotes STAT3-mediated transcription. To assess effects of MUC1-C on the STAT3 transcription complex, the inventors first showed that activation of the MUC1 promoter in the response of MCF-10A cells to IL-6 is indeed mediated by STAT3 and occupancy of STAT3 on the STAT binding site in the MUC1 promoter. Surprisingly, however, silencing MUC1 in the MCF-10A cells attenuated IL-6-induced targeting of STAT3 to the STAT binding site, indicating that MUC1-C may play a role in initiating STAT3 occupancy of that site or in delaying STAT3 latency. The demonstration that MUC1-C also promotes STAT3-mediated activation of the MUC1 promoter provided further support for the induction of an auto-inductive loop in which MUC1-C and STAT3 work cooperatively to activate expression of the MUC1 gene. In concert with these observations, silencing MUC1 in breast cancer cells was associated with decreases in (i) constitutive STAT3 occupancy on the STAT binding site, and (ii) constitutive activation of the MUC1 promoter. To provide further support for an auto-inductive loop, studies were performed with GO-201, an inhibitor of MUC1-C oligomerization (Raina, 2009). GO-201, and not the inactive CP-1 mutant, blocked the interaction between the MUC1-C cytoplasmic domain and STAT3 in vitro and in IL-6-stimulated MCF-10A cells. Significantly, GO-201 also blocked IL-6-induced targeting of MUC1-C and STAT3 to the MUC1 promoter, again indicating that MUC1-C promotes STAT3 occupancy of the STAT binding site. Moreover, GO-201 blocked IL-6 induced activation of the MUC1 promoter. The results obtained from IL-6-stimulated MCF-10A cells were confirmed in breast cancer cells with the demonstration that GO-201 inhibits constitutive occupancy of the MUC1 promoter by MUC1-C and STAT3, and constitutive activation of the MUC1 promoter. These findings thus provide support for the potential importance of the MUC1-C-STAT3 interaction in targeting STAT3 to the MUC1 promoter and promoting activation of the MUC1 gene in an auto-inductive loop (FIG. 7D).

Does the MUC1-C-STAT3 interaction contribute to a physiologic defense mechanism exploited by human tumors? The epithelial cell barrier is exposed to diverse forms of stress, including inflammatory settings associated with production of cytokines, such as tumor necrosis factor α, interferon-γ and IL-6. Epithelial cells thus need a robust defense mechanism to survive in the presence of such insults. In this regard, the MUC1-C subunit and specifically its cytoplasmic domain is sufficient to confer resistance to death in response to multiple insults, including genotoxic, oxidative and hypoxic stress (Ren, 2004; Raina, 2004; Yin, 2003; Yin, 2004; Yin, 2007). The present results suggest that IL-6-mediated activation of the STAT3 pathway induces MUC1 expression as a potential mechanism to protect against epithelial damage during an inflammatory response. In this model, MUC1 could play a physiologic role in transiently dictating cell fate. Conversely, irreversible activation of MUC1 expression through a MUC1-C-STAT3 auto-inductive loop could confer a phenotype that is stably resistant to cell death. Therefore, a physiologic mechanism that protects epithelial cells during an inflammatory response may have been exploited by human breast carcinomas to survive under adverse conditions. The present results further indicate that targeting MUC1-C function could affect constitutive activation of the STAT3 pathway in breast cancer cells.

\*\*\*\*\*\*\*\*\*\*\*\*\*

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. REFERENCES

The following references, to the extent that they provide exemplary procedural or other details supplementary to those set forth herein, are specifically incorporated herein by reference:

U.S. Pat. No. 5,440,013
U.S. Pat. No. 5,446,128
U.S. Pat. No. 5,475,085
U.S. Pat. No. 5,597,457
U.S. Pat. No. 5,618,914
U.S. Pat. No. 5,670,155
U.S. Pat. No. 5,672,681
U.S. Pat. No. 5,674,976
U.S. Pat. No. 5,710,245
U.S. Pat. No. 5,790,421
U.S. Pat. No. 5,840,833
U.S. Pat. No. 5,859,184
U.S. Pat. No. 5,889,155
U.S. Pat. No. 5,929,237
U.S. Pat. No. 6,093,573
U.S. Pat. No. 6,261,569
U.S. Patent Appln. 2005/0015232
Aaronson and Horvath, *Science*, 296(5573):1653-5, 2002.
Abe and Kufe, *Cancer Res.*, 49(11):2834-2839, 1989.
Agata et al., *Cancer Res.*, 68:6136-44, 2008.
Ahmad et al., *Cancer Res.*, 68:2920-2926, 2008.
Ahmad et al., *J. Biol. Chem.*, 281:35764-9, 2006.
Ahmad et al., *Nat. Cell Biol.*, 9:1419-1427, 2007.
Alvarez et al., *Cancer Res.*, 65(12):5054-62, 2005.
Alvarez et al., *Cancer Res.*, 66(6):3162-8, 2006.
Baldus et al., *Clin. Cancer Res.*, 10(8):2790-2796, 2004.
Bodanszky et al., *J. Antibiot.*, 29(5):549-53, 1976.
Bowman et al., *Oncogene*, 19(21):2474-88, 2000.
Bromberg et al., *Cell*, 98(3):295-303, 1999.
Buerger et al., *J. Biol. Chem.*, 278(39):37610-21, 2003.
Chen & Greene, *Mol. Cell. Biol.* 5:392-401, 2004.
Cohen et al., *J. Med. Chem.*, 33:883-894, 1990.
Duraisamy et al., *Gene*, 373:28-34, 2006.
Fischer, *Med. Res. Rev.*, 27(6):755-796, 2007.
Gaemers et al., *J. Biol. Chem.*, 276:6191-6199, 2001.
Gendler et al., *J. Biol. Chem.*, 263:12820-12823, 1988.
Germain and Frank, *Clin. Cancer Res.*, 13(19):5665-9, 2007.
Gerondakis et al., *Oncogene* 25(51):6781-99, 2006.
Ghosh et al., *Annu. Rev. Cell. Dev. Biol.*, 16:225-60, 1998.
Gilmore, available from NF-kB.org, 2008.
Grillot et al., *J. Immunol.*, 158:4750-7, 1997.
Gronenborn et al., *Anal. Chem.*, 62(1):2-15, 1990.
Hayden and Ghosh, *Cell*, 132:344-62, 2008.
Hodel et al., *Mol. Cell*, 10(2):347-58, 2002.
Hoffman et al., *Oncogene*, 25:6706-16, 2006.
Huang et al., *Cancer Biol Ther.*, 2:702-706, 2003.
Huang et al., *Cancer Res.*, 65:10413-10422, 2005.
Huxford et al., *Cell* 95(6):759-70, 1998.
Jackson, *Seminars in Oncology*, 24:L164-172, 1997.
Jacobs et al., *Cell*, 95:749-58, 1998.
Johnson et al., In: *Biotechnology And Pharmacy*, Pezzuto et al. (Eds.), Chapman and Hall, NY, 1993.
Jones et al., *J. Med. Chem.*, 39:904-917, 1996.
Karin & Lin, *Nat. Immunol.*, 3:221-7, 2002.
Kau et al., *Nat. Rev. Cancer*, 4(2):106-17, 2004.
Kawano et al., *Cancer Res.*, 67:11576-84, 2007.
Kinlough et al., *J. Biol. Chem.*, 279(51):53071-53077, 2004.
Kufe et al., *Hybridoma*, 3:223-232, 1984.
Lagow and Carson, *J. Cell. Biochem.*, 86:759-72, 2002.
Lee et al., *Cancer Cell*, 15(4):283-293, 2009.
Leng et al., *J. Biol. Chem.*, 282:19321-19330, 2007.
Levitan et al., *J. Biol. Chem.*, 280:33374-33386, 2005.
Li et al., *Cancer Biol. Ther.*, 2:187-193, 2003b.
Li et al., *J. Biol. Chem.*, 276:35239-35242, 2001.
Li et al., *J. Biol. Chem.*, 276:6061-6064, 2001.
Li et al., *Mol. Cancer Res.*, 1:765-775, 2003c.
Li et al., *Mol. Cell Biol.*, 18:7216-7224, 1998.
Li et al., *Oncogene*, 22:6107-6110, 2003a.
Ligtenberg et al., *J. Biol. Chem.*, 267, 6171-6177, 1992.
Macao, *Nat. Struct. Mol. Biol.*, 13, 71-76, 2006.
McPherson, *J. Biol. Chem.*, 251:6300-6306, 1976.
Merlo et al., *Cancer Res.*, 49, 6966-6971, 1989.
Merrifield, *J. Am. Chem. Soc.*, 85:2149-2154, 1963.
Micheau & Tschopp, *Cell*, 114:181-90, 2003.
Muthuswamy, *Nat. Cell Biol.*, 3(9):785-92, 2001.
Natoli et al., *Nat. Immunol.*, 6:439-45, 2005.
Navia et al., *Curr. Opin. Struct. Biol.*, 2:202-210, 1992.
Pasparakis et al., *Cell Death Differ.* 13:861-72, 2006.
PCT Appln. PCT/US00/03745
PCT Appln. PCT/US00/14667
PCT Appln. PCT/US99/11913
PCT Appln. PCT/US99/18441
Peptide Synthesis, 1985
Percipalle et al., *J. Mol. Biol.*, (4):722-32, 1997.
Perey et al., *Cancer Res.*, 52(22):6365-6370, 1992.
Protective Groups in Organic Chemistry, 1973
Protein NMR Spectroscopy, Principles and Practice, J. Cavanagh et al., Academic Press, San Diego, 1996.
Raina et al., *Direct targeting of the MUC1 oncoprotein blocks survival and tumorigenicity of human breast carcinoma cells. Cancer Res.*, 2009 (IN PRESS).
Raina et al., *EMBO J.*, 25:3774-3783, 2006.
Raina et al., *J. Biol. Chem.*, 279:20607-20612, 2004.
Ramasamy et al., *Mol. Cell*, 27:992-1004, 2007.
Remington's Pharmaceutical Sciences, 15th Ed., 1035-1038 and 1570-1580, 1990.
Remington's Pharmaceutical Sciences, 15th Ed., 3:624-652, 1990.
Ren et al., *Cancer Cell*, 5:163-175, 2004.
Ren et al., *J. Biol. Chem.*, 277:17616-17622, 2002.
Ryan and Wente, *Curr. Opin. Cell Biol.*, 12(3):361-71, 2000.
Schneider-Brachert et al., *Immunity*, 21:415-28, 2004.
Schroeder et al., *J. Biol. Chem.*, 276(16):13057-13064 2001.
Schroeder et al., *Oncogene*, 23:5739-5747, 2004.
Shuai, *Oncogene*, 19(21):2638-44, 2000.
Siddiquee et al., *Proc. Natl. Acad. Sci. USA*, 104(18):7391-6, 2007.
Siddiqui et al., *Proc. Natl. Acad. Sci. USA*, 85:2320-2323, 1988.
Solid Phase Peptide Synthelia, 1984
Song et al., *Proc. Natl. Acad. Sci. USA*, 102(13):4700-5, 2005.
Soule et al., *Cancer Res.*, 50(18):6075-6086, 1990.

Suh and Gumbiner, *Exp. Cell Res.*, 290(2):447-56, 2003.
Truscott et al., *J. Cell Biol.*, 163(4):707-713, 2003.
Vermeer et al., *Nature*, 422(6929):322-6, 2003.
Weber, *Advances Protein Chem.*, 41:1-36, 1991.
Wegenka et al., *Mol. Cell. Biol.*, 14(5):3186-96, 1994.
Wei et al., *Cancer Cell*, 7:167-178, 2005.
Wei et al., *Cancer Res.*, 67(4):1853-8, 2007.
Wei et al., *Mol. Cell.*, 21:295-305, 2006.
Weis, *Cell*, 112(4):441-51, 2003.
Wen et al., *J. Biol. Chem.*, 278:38029-38039, 2003.
Wider, *BioTechniques*, 29:1278-1294, 2000.
Yamamoto et al., *J. Biol. Chem.*, 272:12492-12494, 1997.
Yin et al., *J. Biol. Chem.*, 278:35458-35464, 2003.
Yin et al., *J. Biol. Chem.*, 279:45721-45727, 2004.
Yin et al., *J. Biol. Chem.*, 282:257-266, 2007.
Young et al., *Cell.* 112(1):41-50, 2003.
Yu and Jove, *Nat. Rev. Cancer*, 4(2):97-105, 2004.
Zhang et al., *Mol. Cell. Biol.*, 19:7138-7146, 1999.

---

What is claimed is:

1. A method of inhibiting inflammatory signaling in a subject suffering from inflammatory bowel disease comprising contacting a MUC 1-expressing cell in said subject with a MUC1 peptide of at least 6 consecutive MUC1 residues and no more than 20 consecutive MUC1 residues and comprising the sequence CQCRRK (SEQ ID NO:4), wherein the amino-terminal cysteine of CQC is covered on its NH$_2$-terminus by at least one amino acid residue that need not correspond to the native MUC-1 transmembrane sequence.

2. The method of claim 1, wherein said peptide comprises at least 7 consecutive MUC1 residues.

3. The method of claim 2, wherein the sequence comprises CQCRRKN (SEQ ID NO:53).

4. The method of claim 1, wherein said peptide contains no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1.

5. The method of claim 1, wherein the MUC1-positive cell is an endothelial cell or an inflammatory cell.

6. The method of claim 1, wherein said peptide is fused to a cell delivery domain.

7. The method of claim 6, wherein said cell delivery domain is poly-D-R, poly-D-P or poly-D-K.

8. The method of claim 1, further comprising contacting said cell with a second anti-inflammatory agent.

9. The method of claim 1, wherein said peptide comprises all L amino acids.

10. The method of claim 1, wherein said peptide comprises all D amino acids.

11. The method of claim 1, wherein said peptide comprises a mix of L and D amino acids.

12. A method of inhibiting an inflammatory bowel disease in a subject comprising administering to said subject a MUC1 peptide of at least 6 consecutive MUC1 residues and no more than 20 consecutive MUC1 residues and comprising the sequence CQCRRK (SEQ ID NO:4), wherein the amino-terminal cysteine of CQCRRK is covered on its NH$_2$-terminus by at least one amino acid residue that need not correspond to the native MUC-1 transmembrane sequence.

13. The method of claim 12, wherein said peptide comprises at least 7 consecutive MUC1 residues.

14. The method of claim 13, wherein the sequence comprises CQCRRKN (SEQ ID NO:53).

15. The method of claim 12, wherein said peptide contains no more than 10 consecutive residues, 11 consecutive residues, 12 consecutive residues, 13 consecutive residues, 14 consecutive residues, 15 consecutive residues, 16 consecutive residues, 17 consecutive residues, 18 consecutive residues or 19 consecutive residues of MUC1.

16. The method of claim 12, wherein said peptide is fused to a cell delivery domain.

17. The method of claim 16, wherein said cell delivery domain is poly-D-R, poly-D-P or poly-D-K.

18. The method of claim 12, wherein administering comprises intravenous, intra-arterial, oral, intratumoral, subcutaneous, topical or intraperitoneal administration.

19. The method of claim 12, wherein administering comprises local, regional, systemic, or continual administration.

20. The method of claim 12, wherein inhibiting comprises inhibition or resolution of the inflammatory bowel disease.

21. The method of claim 12, further comprising administering to said subject a second anti-inflammatory bowel disease therapy.

22. The method of claim 12, wherein said subject is a human.

23. The method of claim 12, wherein said peptide is administered at 0.1-500 mg/kg/d.

24. The method of claim 12, wherein said peptide is administered at 10-100 mg/kg/d.

25. The method of claim 12, wherein said peptide comprises all L amino acids.

26. The method of claim 12, wherein said peptide comprises all D amino acids.

27. The method of claim 12, wherein said peptide comprises a mix of L and D amino acids.

* * * * *

SEQUENCE LISTING

```
<160> NUMBER OF SEQ ID NOS: 66

<210> SEQ ID NO 1
<211> LENGTH: 72
<212> TYPE: PRT
<213> ORGANISM: Artificial Sequence
<220> FEATURE:
<223> OTHER INFORMATION: Synthetic peptide

<400> SEQUENCE: 1

Cys Gln Cys Arg Arg Lys Asn Tyr Gly Gln Leu Asp Ile Phe Pro Ala
1               5                   10                  15

Arg Asp Thr Tyr His Pro Met Ser Glu Tyr Pro Thr Tyr His Thr His
                20                  25                  30

Gly Arg Tyr Val Pro Pro Ser Ser Thr Asp Arg Ser Pro Tyr Glu Lys
            35                  40                  45

Val Ser Ala Gly Asn Gly Gly Ser Ser Leu Ser Tyr Thr Asn Pro Ala
    50                  55                  60

Val Ala Ala Thr Ser Ala Asn Leu
65                  70

<210> SEQ ID NO 2
<211> LENGTH: 159
<212> TYPE: PRT
<213> ORGANISM: Artificial
<220> FEATURE:
<223> OTHER INFORMATION: Synthetic peptide

<400> SEQUENCE: 2

Gly Ser Val Val Val Gln Leu Thr Leu Ala Phe Arg Glu Gly Thr Ile
1               5                   10                  15

Asn Val His Asp Val Glu Thr Gln Phe Asn Gln Tyr Lys Thr Glu Ala
                20                  25                  30

Ala Ser Arg Tyr Asn Leu Thr Ile Ser Asp Val Ser Val Ser Asp Val
            35                  40                  45

Pro Phe Pro Phe Ser Ala Gln Ser Gly Ala Gly Val Pro Gly Trp Gly
    50                  55                  60

Ile Ala Leu Leu Val Leu Val Cys Val Leu Val Ala Leu Ala Ile Val
65                  70                  75                  80

Tyr Leu Ile Ala Leu Ala Val Cys Gln Cys Arg Arg Lys Asn Tyr Gly
                85                  90                  95

Gln Leu Asp Ile Phe Pro Ala Arg Asp Thr Tyr His Pro Met Ser Glu
                100                 105                 110

Tyr Pro Thr Tyr His Thr His Gly Arg Tyr Val Pro Pro Ser Ser Thr
            115                 120                 125

Asp Arg Ser Pro Tyr Glu Lys Val Ser Ala Gly Asn Gly Gly Ser Ser
        130                 135                 140

Leu Ser Tyr Thr Asn Pro Ala Val Ala Ala Thr Ser Ala Asn Leu
145                 150                 155
```

```
<210> SEQ ID NO 3
<211> LENGTH: 15
<212> TYPE: PRT
<213> ORGANISM: Artificial
<220> FEATURE:
<223> OTHER INFORMATION: Synthetic peptide

<400> SEQUENCE: 3

Cys Gln Cys Arg Arg Lys Asn Tyr Gly Gln Leu Asp Ile Phe Pro
1               5                   10                  15

<210> SEQ ID NO 4
<211> LENGTH: 6
<212> TYPE: PRT
<213> ORGANISM: Artificial
<220> FEATURE:
<223> OTHER INFORMATION: Synthetic peptide

<400> SEQUENCE: 4

Cys Gln Cys Arg Arg Lys
1               5

<210> SEQ ID NO 5
<211> LENGTH: 34
<212> TYPE: PRT
<213> ORGANISM: Artificial
<220> FEATURE:
<223> OTHER INFORMATION: Synthetic peptide

<400> SEQUENCE: 5

Gln Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 6
<211> LENGTH: 16
<212> TYPE: PRT
<213> ORGANISM: Artificial
<220> FEATURE:
<223> OTHER INFORMATION: Synthetic peptide

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 7
<212> TYPE: PRT
<213> ORGANISM: Artificial
<220> FEATURE:
<223> OTHER INFORMATION: Synthetic peptide

<400> SEQUENCE: 7

Arg Arg Met Lys Trp Lys Lys
1               5

<210> SEQ ID NO 8
<211> LENGTH: 16
<212> TYPE: PRT
<213> ORGANISM: Artificial
<220> FEATURE:
<223> OTHER INFORMATION: Synthetic peptide

<400> SEQUENCE: 8
```

```
Arg Arg Trp Arg Arg Trp Trp Arg Arg Trp Trp Arg Arg Trp Arg Arg
1               5                   10                  15
```

<210> SEQ ID NO 9
<211> LENGTH: 18
<212> TYPE: PRT
<213> ORGANISM: Artificial
<220> FEATURE:
<223> OTHER INFORMATION: Synthetic peptide

<400> SEQUENCE: 9

```
Arg Gly Gly Arg Leu Ser Tyr Ser Arg Arg Phe Ser Thr Ser Thr
1               5                   10                  15

Gly Arg
```

<210> SEQ ID NO 10
<211> LENGTH: 11
<212> TYPE: PRT
<213> ORGANISM: Artificial
<220> FEATURE:
<223> OTHER INFORMATION: Synthetic peptide

<400> SEQUENCE: 10

```
Tyr Gly Arg Lys Lys Arg Arg Gln Arg Arg Arg
1               5                   10
```

<210> SEQ ID NO 11
<211> LENGTH: 9
<212> TYPE: PRT
<213> ORGANISM: Artificial
<220> FEATURE:
<223> OTHER INFORMATION: Synthetic peptide

<400> SEQUENCE: 11

```
Arg Lys Lys Arg Arg Gln Arg Arg Arg
1               5
```

<210> SEQ ID NO 12
<211> LENGTH: 11
<212> TYPE: PRT
<213> ORGANISM: Artificial
<220> FEATURE:
<223> OTHER INFORMATION: Synthetic peptide

<400> SEQUENCE: 12

```
Tyr Ala Arg Ala Ala Ala Arg Gln Ala Arg Ala
1               5                   10
```

<210> SEQ ID NO 13
<211> LENGTH: 8
<212> TYPE: PRT
<213> ORGANISM: Artificial
<220> FEATURE:
<223> OTHER INFORMATION: Synthetic peptide

<400> SEQUENCE: 13

```
Arg Arg Arg Arg Arg Arg Arg Arg
1               5
```

<210> SEQ ID NO 14
<211> LENGTH: 8
<212> TYPE: PRT
<213> ORGANISM: Artificial
<220> FEATURE:
<223> OTHER INFORMATION: Synthetic peptide

<400> SEQUENCE: 14

```
Lys Lys Lys Lys Lys Lys Lys Lys
1               5

<210> SEQ ID NO 15
<211> LENGTH: 27
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (25)..(25)
<223> OTHER INFORMATION: Xaa can be any naturally occurring amino acid

<400> SEQUENCE: 15

Gly Trp Thr Leu Asn Ser Ala Gly Tyr Leu Leu Gly Lys Ile Asn Leu
1               5                   10                  15

Lys Ala Leu Ala Ala Leu Ala Lys Xaa Ile Leu
            20                  25

<210> SEQ ID NO 16
<211> LENGTH: 18
<212> TYPE: PRT
<213> ORGANISM: Artificial
<220> FEATURE:
<223> OTHER INFORMATION: Synthetic peptide

<400> SEQUENCE: 16

Leu Leu Ile Leu Leu Arg Arg Arg Ile Arg Lys Gln Ala Asn Ala His
1               5                   10                  15

Ser Lys

<210> SEQ ID NO 17
<211> LENGTH: 16
<212> TYPE: PRT
<213> ORGANISM: Artificial
<220> FEATURE:
<223> OTHER INFORMATION: Synthetic peptide

<400> SEQUENCE: 17

Ser Arg Arg His His Cys Arg Ser Lys Ala Lys Arg Ser Arg His His
1               5                   10                  15

<210> SEQ ID NO 18
<211> LENGTH: 11
<212> TYPE: PRT
<213> ORGANISM: Artificial
<220> FEATURE:
<223> OTHER INFORMATION: Synthetic peptide

<400> SEQUENCE: 18

Asn Arg Ala Arg Arg Asn Arg Arg Arg Val Arg
1               5                   10

<210> SEQ ID NO 19
<211> LENGTH: 15
<212> TYPE: PRT
<213> ORGANISM: Artificial
<220> FEATURE:
<223> OTHER INFORMATION: Synthetic peptide

<400> SEQUENCE: 19

Arg Gln Leu Arg Ile Ala Gly Arg Arg Leu Arg Gly Arg Ser Arg
1               5                   10                  15

<210> SEQ ID NO 20
```

```
<211> LENGTH: 13
<212> TYPE: PRT
<213> ORGANISM: Artificial
<220> FEATURE:
<223> OTHER INFORMATION: Synthetic peptide

<400> SEQUENCE: 20

Lys Leu Ile Lys Gly Arg Thr Pro Ile Lys Phe Gly Lys
1               5                   10

<210> SEQ ID NO 21
<211> LENGTH: 10
<212> TYPE: PRT
<213> ORGANISM: Artificial
<220> FEATURE:
<223> OTHER INFORMATION: Synthetic peptide

<400> SEQUENCE: 21

Arg Arg Ile Pro Asn Arg Arg Pro Arg Arg
1               5                   10

<210> SEQ ID NO 22
<211> LENGTH: 18
<212> TYPE: PRT
<213> ORGANISM: Artificial
<220> FEATURE:
<223> OTHER INFORMATION: Synthetic peptide

<400> SEQUENCE: 22

Lys Leu Ala Leu Lys Leu Ala Leu Lys Ala Leu Lys Ala Ala Leu Lys
1               5                   10                  15

Leu Ala

<210> SEQ ID NO 23
<211> LENGTH: 14
<212> TYPE: PRT
<213> ORGANISM: Artificial
<220> FEATURE:
<223> OTHER INFORMATION: Synthetic peptide

<400> SEQUENCE: 23

Lys Leu Ala Lys Leu Ala Lys Lys Leu Ala Lys Leu Ala Lys
1               5                   10

<210> SEQ ID NO 24
<211> LENGTH: 27
<212> TYPE: PRT
<213> ORGANISM: Artificial
<220> FEATURE:
<223> OTHER INFORMATION: Synthetic peptide

<400> SEQUENCE: 24

Gly Ala Leu Phe Leu Gly Phe Leu Gly Ala Ala Gly Ser Thr Asn Gly
1               5                   10                  15

Ala Trp Ser Gln Pro Lys Lys Lys Arg Lys Val
            20                  25

<210> SEQ ID NO 25
<211> LENGTH: 21
<212> TYPE: PRT
<213> ORGANISM: Artificial
<220> FEATURE:
<223> OTHER INFORMATION: Synthetic peptide

<400> SEQUENCE: 25

Lys Glu Thr Trp Trp Glu Thr Trp Trp Thr Glu Trp Ser Gln Pro Lys
1               5                   10                  15
```

```
Lys Lys Arg Lys Val
            20

<210> SEQ ID NO 26
<211> LENGTH: 23
<212> TYPE: PRT
<213> ORGANISM: Artificial
<220> FEATURE:
<223> OTHER INFORMATION: Synthetic peptide

<400> SEQUENCE: 26

Gly Ala Leu Phe Leu Gly Trp Leu Gly Ala Ala Gly Ser Thr Met Gly
1               5                   10                  15

Ala Lys Lys Lys Arg Lys Val
            20

<210> SEQ ID NO 27
<211> LENGTH: 23
<212> TYPE: PRT
<213> ORGANISM: Artificial
<220> FEATURE:
<223> OTHER INFORMATION: Synthetic peptide

<400> SEQUENCE: 27

Met Gly Leu Gly Leu His Leu Leu Val Leu Ala Ala Ala Leu Gln Gly
1               5                   10                  15

Ala Lys Ser Lys Arg Lys Val
            20

<210> SEQ ID NO 28
<211> LENGTH: 26
<212> TYPE: PRT
<213> ORGANISM: Artificial
<220> FEATURE:
<223> OTHER INFORMATION: Synthetic peptide

<400> SEQUENCE: 28

Ala Ala Val Ala Leu Leu Pro Ala Val Leu Leu Ala Leu Leu Ala Pro
1               5                   10                  15

Ala Ala Ala Asn Tyr Lys Lys Pro Lys Leu
            20                  25

<210> SEQ ID NO 29
<211> LENGTH: 28
<212> TYPE: PRT
<213> ORGANISM: Artificial
<220> FEATURE:
<223> OTHER INFORMATION: Synthetic peptide

<400> SEQUENCE: 29

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 30
<211> LENGTH: 24
<212> TYPE: PRT
<213> ORGANISM: Artificial
<220> FEATURE:
<223> OTHER INFORMATION: Synthetic peptide

<400> SEQUENCE: 30

Leu Gly Thr Tyr Thr Gln Asp Phe Asn Lys Phe His Thr Phe Pro Gln
1               5                   10                  15
```

Thr Ala Ile Gly Val Gly Ala Pro
            20

<210> SEQ ID NO 31
<211> LENGTH: 26
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (24)..(24)
<223> OTHER INFORMATION: Xaa can be any naturally occurring amino acid

<400> SEQUENCE: 31

Asp Pro Lys Gly Asp Pro Lys Gly Val Thr Val Thr Val Thr
1               5                   10                  15

Val Thr Gly Lys Gly Asp Pro Xaa Pro Asp
            20                  25

<210> SEQ ID NO 32
<211> LENGTH: 14
<212> TYPE: PRT
<213> ORGANISM: Artificial
<220> FEATURE:
<223> OTHER INFORMATION: Synthetic peptide

<400> SEQUENCE: 32

Pro Pro Pro Pro Pro Pro Pro Pro Pro Pro Pro Pro Pro Pro
1               5                   10

<210> SEQ ID NO 33
<211> LENGTH: 18
<212> TYPE: PRT
<213> ORGANISM: Artificial
<220> FEATURE:
<223> OTHER INFORMATION: Synthetic peptide

<400> SEQUENCE: 33

Val Arg Leu Pro Pro Pro Val Arg Leu Pro Pro Pro Val Arg Leu Pro
1               5                   10                  15

Pro Pro

<210> SEQ ID NO 34
<211> LENGTH: 10
<212> TYPE: PRT
<213> ORGANISM: Artificial
<220> FEATURE:
<223> OTHER INFORMATION: Synthetic peptide

<400> SEQUENCE: 34

Pro Arg Pro Leu Pro Pro Pro Arg Pro Gly
1               5                   10

<210> SEQ ID NO 35
<211> LENGTH: 30
<212> TYPE: PRT
<213> ORGANISM: Artificial
<220> FEATURE:
<223> OTHER INFORMATION: Synthetic peptide

<400> SEQUENCE: 35

Ser Val Arg Arg Arg Pro Arg Pro Pro Tyr Leu Pro Arg Pro Arg Pro
1               5                   10                  15

Pro Pro Phe Phe Pro Pro Arg Leu Pro Pro Arg Ile Pro Pro
            20                  25                  30

```
<210> SEQ ID NO 36
<211> LENGTH: 21
<212> TYPE: PRT
<213> ORGANISM: Artificial
<220> FEATURE:
<223> OTHER INFORMATION: Synthetic peptide

<400> SEQUENCE: 36

Thr Arg Ser Ser Arg Ala Gly Leu Gln Phe Pro Val Gly Arg Val His
1               5                   10                  15

Arg Leu Leu Arg Lys
            20

<210> SEQ ID NO 37
<211> LENGTH: 23
<212> TYPE: PRT
<213> ORGANISM: Artificial
<220> FEATURE:
<223> OTHER INFORMATION: Synthetic peptide

<400> SEQUENCE: 37

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 38
<211> LENGTH: 37
<212> TYPE: PRT
<213> ORGANISM: Artificial
<220> FEATURE:
<223> OTHER INFORMATION: Synthetic peptide

<400> SEQUENCE: 38

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
            35

<210> SEQ ID NO 39
<211> LENGTH: 28
<212> TYPE: PRT
<213> ORGANISM: Artificial
<220> FEATURE:
<223> OTHER INFORMATION: Synthetic peptide

<400> SEQUENCE: 39

Ala Leu Trp Met Thr Leu Leu Lys Lys Val Leu Lys Ala Ala Ala Lys
1               5                   10                  15

Ala Ala Leu Asn Ala Val Leu Val Gly Ala Asn Ala
            20                  25

<210> SEQ ID NO 40
<211> LENGTH: 26
<212> TYPE: PRT
<213> ORGANISM: Artificial
<220> FEATURE:
<223> OTHER INFORMATION: Synthetic peptide

<400> SEQUENCE: 40

Gly Ile Gly Ala Val Leu Lys Val Leu Thr Thr Gly Leu Pro Ala Leu
1               5                   10                  15
```

```
Ile Ser Trp Ile Lys Arg Lys Arg Gln Gln
            20              25

<210> SEQ ID NO 41
<211> LENGTH: 14
<212> TYPE: PRT
<213> ORGANISM: Artificial
<220> FEATURE:
<223> OTHER INFORMATION: Synthetic peptide

<400> SEQUENCE: 41

Ile Asn Leu Lys Ala Leu Ala Ala Leu Ala Lys Lys Ile Leu
1               5                   10

<210> SEQ ID NO 42
<211> LENGTH: 33
<212> TYPE: PRT
<213> ORGANISM: Artificial
<220> FEATURE:
<223> OTHER INFORMATION: Synthetic peptide

<400> SEQUENCE: 42

Gly Phe Phe Ala Leu Ile Pro Lys Ile Ile Ser Ser Pro Leu Pro Lys
1               5                   10                  15

Thr Leu Leu Ser Ala Val Gly Ser Ala Leu Gly Gly Ser Gly Gly Gln
            20                  25                  30

Glu

<210> SEQ ID NO 43
<211> LENGTH: 15
<212> TYPE: PRT
<213> ORGANISM: Artificial
<220> FEATURE:
<223> OTHER INFORMATION: Synthetic peptide

<400> SEQUENCE: 43

Leu Ala Lys Trp Ala Leu Lys Gln Gly Phe Ala Lys Leu Lys Ser
1               5                   10                  15

<210> SEQ ID NO 44
<211> LENGTH: 27
<212> TYPE: PRT
<213> ORGANISM: Artificial
<220> FEATURE:
<223> OTHER INFORMATION: Synthetic peptide
<220> FEATURE:
<221> NAME/KEY: misc_feature
<222> LOCATION: (23)..(23)
<223> OTHER INFORMATION: Xaa can be any naturally occurring amino acid

<400> SEQUENCE: 44

Ser Met Ala Gln Asp Ile Ile Ser Thr Ile Gly Asp Leu Val Lys Trp
1               5                   10                  15

Ile Ile Gln Thr Val Asn Xaa Phe Thr Lys Lys
            20                  25

<210> SEQ ID NO 45
<211> LENGTH: 41
<212> TYPE: PRT
<213> ORGANISM: Artificial
<220> FEATURE:
<223> OTHER INFORMATION: Synthetic peptide

<400> SEQUENCE: 45

Leu Leu Gly Asp Phe Phe Arg Lys Ser Lys Glu Lys Ile Gly Lys Glu
1               5                   10                  15
```

```
Phe Lys Arg Ile Val Gln Arg Ile Lys Gln Arg Ile Lys Asp Phe Leu
            20                  25                  30

Ala Asn Leu Val Pro Arg Thr Glu Ser
        35                  40

<210> SEQ ID NO 46
<211> LENGTH: 20
<212> TYPE: PRT
<213> ORGANISM: Artificial
<220> FEATURE:
<223> OTHER INFORMATION: Synthetic peptide

<400> SEQUENCE: 46

Leu Lys Lys Leu Leu Lys Lys Leu Leu Lys Lys Leu Leu Lys Lys Leu
1               5                   10                  15

Leu Lys Lys Leu
            20

<210> SEQ ID NO 47
<211> LENGTH: 18
<212> TYPE: PRT
<213> ORGANISM: Artificial
<220> FEATURE:
<223> OTHER INFORMATION: Synthetic peptide

<400> SEQUENCE: 47

Lys Leu Lys Leu Lys Leu Lys Leu Lys Leu Lys Leu Lys Leu Lys Leu
1               5                   10                  15

Lys Leu

<210> SEQ ID NO 48
<211> LENGTH: 18
<212> TYPE: PRT
<213> ORGANISM: Artificial
<220> FEATURE:
<223> OTHER INFORMATION: Synthetic peptide

<400> SEQUENCE: 48

Pro Ala Trp Arg Lys Ala Phe Arg Trp Ala Trp Arg Met Leu Lys Lys
1               5                   10                  15

Ala Ala

<210> SEQ ID NO 49
<211> LENGTH: 6
<212> TYPE: PRT
<213> ORGANISM: Artificial
<220> FEATURE:
<223> OTHER INFORMATION: Synthetic peptide

<400> SEQUENCE: 49

Lys Arg Arg Cys Gln Cys
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic peptide

<400> SEQUENCE: 50

Cys Gln Cys Arg Arg
1               5
```

```
<210> SEQ ID NO 51
<211> LENGTH: 6
<212> TYPE: PRT
<213> ORGANISM: Artificial Sequence
<220> FEATURE:
<223> OTHER INFORMATION: Synthetic peptide

<400> SEQUENCE: 51

Cys Gln Cys Arg Arg Arg
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic peptide

<400> SEQUENCE: 52

Cys Gln Cys Arg Arg Arg Arg
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic peptide

<400> SEQUENCE: 53

Cys Gln Cys Arg Arg Lys Asn
1               5

<210> SEQ ID NO 54
<211> LENGTH: 4
<212> TYPE: PRT
<213> ORGANISM: Artificial Sequence
<220> FEATURE:
<223> OTHER INFORMATION: Synthetic peptide

<400> SEQUENCE: 54

Cys Gln Cys Arg
1

<210> SEQ ID NO 55
<211> LENGTH: 21
<212> TYPE: DNA
<213> ORGANISM: Artificial Sequence
<220> FEATURE:
<223> OTHER INFORMATION: Synthetic primer

<400> SEQUENCE: 55
aagttcagtg cccagctcta c                                          21

<210> SEQ ID NO 56
<211> LENGTH: 20
<212> TYPE: DNA
<213> ORGANISM: Artificial Sequence
<220> FEATURE:
<223> OTHER INFORMATION: Synthetic primer

<400> SEQUENCE: 56
cgcttaccga ttcagaatgg                                            20

<210> SEQ ID NO 57
<211> LENGTH: 10
<212> TYPE: DNA
<213> ORGANISM: Artificial Sequence
```

```
<220> FEATURE:
<223> OTHER INFORMATION: Synthetic primer
<220> FEATURE:
<221> NAME/KEY: modified_base
<222> LOCATION: (4)..(4)
<223> OTHER INFORMATION: R = purine
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: modified_base
<222> LOCATION: (6)..(6)
<223> OTHER INFORMATION: W = adenine or thymine
<220> FEATURE:
<221> NAME/KEY: modified_base
<222> LOCATION: (7)..(8)
<223> OTHER INFORMATION: Y = pyrimidine

<400> SEQUENCE: 57 gggrnwyycc                                                            10

<210> SEQ ID NO 58
<211> LENGTH: 22
<212> TYPE: DNA
<213> ORGANISM: Artificial Sequence
<220> FEATURE:
<223> OTHER INFORMATION: Synthetic primer

<400> SEQUENCE: 58
gggctattcc ggggaagtgg tg                                              22

<210> SEQ ID NO 59
<211> LENGTH: 27
<212> TYPE: PRT
<213> ORGANISM: Artificial Sequence
<220> FEATURE:
<223> OTHER INFORMATION: Synthetic primer

<400> SEQUENCE: 59

Tyr Glu Lys Val Ser Ala Gly Asn Gly Gly Ser Ser Leu Ser Tyr Thr
1               5                   10                  15

Asn Pro Ala Val Ala Ala Thr Ser Ala Asn Leu
            20                  25

<210> SEQ ID NO 60
<211> LENGTH: 7
<212> TYPE: PRT
<213> ORGANISM: Artificial Sequence
<220> FEATURE:
<223> OTHER INFORMATION: Synthetic peptide

<400> SEQUENCE: 60

Gly Gly Ser Ser Leu Ser Tyr
1               5

<210> SEQ ID NO 61
<211> LENGTH: 13
<212> TYPE: PRT
<213> ORGANISM: Artificial Sequence
<220> FEATURE:
<223> OTHER INFORMATION: Synthetic primer

<400> SEQUENCE: 61

Tyr Thr Asn Pro Ala Val Ala Ala Thr Ser Ala Asn Leu
1               5                   10

<210> SEQ ID NO 62
<211> LENGTH: 15
```

```
<212> TYPE: PRT
<213> ORGANISM: Artificial Sequence
<220> FEATURE:
<223> OTHER INFORMATION: Synthetic peptide

<400> SEQUENCE: 62

Ala Gln Ala Arg Arg Lys Asn Tyr Gly Gln Leu Asp Ile Phe Pro
1               5                   10                  15

<210> SEQ ID NO 63
<211> LENGTH: 9
<212> TYPE: DNA
<213> ORGANISM: Artificial Sequence
<220> FEATURE:
<223> OTHER INFORMATION: Synthetic primer

<400> SEQUENCE: 63 ggaaagtcc                                                                 9

<210> SEQ ID NO 64
<211> LENGTH: 19
<212> TYPE: PRT
<213> ORGANISM: Artificial Sequence
<220> FEATURE:
<223> OTHER INFORMATION: Synthetic peptide

<400> SEQUENCE: 64

Ala Ile Val Tyr Leu Ile Ala Leu Ala Val Cys Gln Cys Arg Arg Lys
1               5                   10                  15

Asn Tyr Gly

<210> SEQ ID NO 65
<211> LENGTH: 23
<212> TYPE: PRT
<213> ORGANISM: Artificial Sequence
<220> FEATURE:
<223> OTHER INFORMATION: Synthetic peptide
<220> FEATURE:
<221> NAME/KEY: X
<222> LOCATION: (8)..(8)
<223> OTHER INFORMATION: (S)-alpha-(2'- pentenyl)alanine
<220> FEATURE:
<221> NAME/KEY: X
<222> LOCATION: (12)..(12)
<223> OTHER INFORMATION: (S)-alpha-(2'- pentenyl)alanine

<400> SEQUENCE: 65

Ala Cys Ala Ile Val Tyr Leu Xaa Ala Leu Ala Xaa Cys Gln Cys Arg
1               5                   10                  15

Arg Lys Asn Tyr Gly Asn His
            20

<210> SEQ ID NO 66
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: X
<222> LOCATION: (8)..(8)
<223> OTHER INFORMATION: (S)-alpha-(2'- pentenyl)alanine
<220> FEATURE:
<221> NAME/KEY: X
<222> LOCATION: (12)..(12)
<223> OTHER INFORMATION: bis(4'-pentenyl)glycine
<220> FEATURE:
<221> NAME/KEY: X
<222> LOCATION: (16)..(16)
<223> OTHER INFORMATION: (S)-alpha-(2'- pentenyl)alanine
```

-continued

```
<400> SEQUENCE: 66

Ala Cys Ala Lys Lys Tyr Leu Xaa Ala Leu Ala Xaa Cys Gln Cys Xaa
1               5                   10                  15

Arg Lys Asn Tyr Asn His
            20
```